US010961305B2

(12) United States Patent
Junker et al.

(10) Patent No.: US 10,961,305 B2
(45) Date of Patent: *Mar. 30, 2021

(54) USE OF ANTI-SCLEROSTIN ANTIBODIES IN THE TREATMENT OF OSTEOGENESIS IMPERFECTA

(71) Applicant: MEREO BIOPHARMA 3 LIMITED, London (GB)

(72) Inventors: Uwe Junker, Basel (CH); Michaela Kneissel, Basel (CH); Anthony Kent Hall, Oegstgeest (NL); Rena Joy Eudy, West Hartford (CN); Matthew Manning Riggs, Haddam (CN)

(73) Assignee: MEREO BIOPHARMA 3 LIMITED, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/469,920

(22) PCT Filed: Dec. 21, 2017

(86) PCT No.: PCT/GB2017/053849
§ 371 (c)(1),
(2) Date: Jun. 14, 2019

(87) PCT Pub. No.: WO2018/115879
PCT Pub. Date: Jun. 28, 2018

(65) Prior Publication Data
US 2019/0330322 A1 Oct. 31, 2019

Related U.S. Application Data

(60) Provisional application No. 62/437,358, filed on Dec. 21, 2016.

(51) Int. Cl.
| | | |
|---|---|---|
| A61P 19/08 | (2006.01) |
| A61K 39/395 | (2006.01) |
| A61K 39/00 | (2006.01) |
| A61K 38/29 | (2006.01) |
| C07K 16/22 | (2006.01) |
| A61K 9/00 | (2006.01) |
| A61K 9/19 | (2006.01) |
| A61K 31/663 | (2006.01) |
| A61K 38/22 | (2006.01) |

(52) U.S. Cl.
CPC ............ *C07K 16/22* (2013.01); *A61K 9/0019* (2013.01); *A61K 9/19* (2013.01); *A61K 31/663* (2013.01); *A61K 39/3955* (2013.01); *A61P 19/08* (2018.01); *A61K 38/22* (2013.01); *A61K 38/29* (2013.01); *A61K 2039/505* (2013.01); *A61K 2039/54* (2013.01); *A61K 2039/545* (2013.01); *C07K 2317/56* (2013.01); *C07K 2317/565* (2013.01)

(58) Field of Classification Search
None
See application file for complete search history.

(56) References Cited

U.S. PATENT DOCUMENTS

| 5,453,492 | A | 9/1995 | Butzow et al. |
| 5,616,561 | A | 4/1997 | Barcellos-Hoff |
| 7,872,106 | B2 * | 1/2011 | Paszty ................ A61P 1/16 530/388.24 |
| 7,879,322 | B2 * | 2/2011 | Kneissel ............ G01N 33/6854 424/130.1 |
| 8,246,953 | B2 * | 8/2012 | Kniessel ............ A61P 19/08 424/130.1 |
| 9,617,323 | B2 | 4/2017 | Rabbani |
| 2003/0157508 | A1 | 8/2003 | Ebner et al. |
| 2003/0186915 | A1 | 10/2003 | Pan et al. |
| 2009/0074763 | A1 | 3/2009 | Padhi et al. |
| 2010/0226928 | A1 * | 9/2010 | Dani ................ A61K 9/19 424/152.1 |
| 2020/0199209 | A1 | 6/2020 | Fang et al. |

FOREIGN PATENT DOCUMENTS

| WO | WO-90/05522 A1 | 5/1990 |
| WO | WO-91/13152 A1 | 9/1991 |
| WO | WO-92/22319 A1 | 12/1992 |
| WO | WO-94/05800 A1 | 3/1994 |

(Continued)

OTHER PUBLICATIONS

Sinder et al. , 2014, Osteoporos. Int. 25:2097-2107.*
International Search Report issued in PCT/GB2017/053849 dated Feb. 12, 2018 (3 pages).
Written Opinion issued in PCT/GB2017/053849 dated Feb. 12, 20180 (5 pages).
Grafe, et al, "Sclerostin Antibody Treatment Improves the Bone Phenotype of Crtap -/- Mice, a Model of Recessive Osteogenesis Imperfecta," Journal of Bone and Mineral Research, vol. 31, No. 5, May 2016, pp. 1030-1040.
Jacobsen, et al, "Targeting the LRP5 Pathway Improves Bone Properties in a Mouse Model of Osteogenesis Imperfecta," Journal of Bone and Mineral Research, vol. 29, No. 10, Oct. 2014, pp. 2297-2306.

(Continued)

*Primary Examiner* — Elizabeth C. Kemmerer
(74) *Attorney, Agent, or Firm* — Morgan, Lewis & Bockius LLP

(57) ABSTRACT

Disclosed are methods for treating a patient suffering from osteogenesis imperfecta comprising administering to the patient a therapeutically effective amount of an anti-sclerostin antibody. Methods for increasing bone formation and reducing bone resorption in an osteogenesis imperfecta patient by administering to the patient a therapeutically effective amount of an anti-sclerostin antibody are also disclosed. Further disclosed are compositions for increasing bone formation and reducing bone resorption in an osteogenesis imperfecta patient. The compositions comprise a therapeutically effective amount of an anti-sclerostin antibody. The invention also provides an anti-sclerostin antibody for use in the treatment of osteogenesis imperfecta.

19 Claims, 8 Drawing Sheets

Specification includes a Sequence Listing.

(56) References Cited

FOREIGN PATENT DOCUMENTS

| WO | WO-95/30900 A1 | 11/1995 |
| WO | WO-98/49296 A1 | 11/1998 |
| WO | WO-98/55621 A1 | 12/1998 |
| WO | WO-99/01553 A1 | 1/1999 |
| WO | WO-99/61044 A1 | 12/1999 |
| WO | WO-2000/022909 A2 | 4/2000 |
| WO | WO-00/032773 A1 | 6/2000 |
| WO | WO-00/55193 A2 | 9/2000 |
| WO | WO-01/16604 A1 | 3/2001 |
| WO | WO-01/47944 A2 | 7/2001 |
| WO | WO-01/53836 A2 | 7/2001 |
| WO | WO-01/86003 A2 | 11/2001 |
| WO | WO-01/88103 A2 | 11/2001 |
| WO | WO-01/92308 A2 | 12/2001 |
| WO | WO-01/98491 A2 | 12/2001 |
| WO | WO-02/43759 A2 | 6/2002 |
| WO | WO-02/054940 A2 | 7/2002 |
| WO | WO-03/039534 A1 | 5/2003 |
| WO | WO-03/054152 A2 | 7/2003 |
| WO | WO-03/055911 A2 | 7/2003 |
| WO | WO-03/066081 A2 | 8/2003 |
| WO | WO-03/070937 A1 | 8/2003 |
| WO | WO-03/073991 A2 | 9/2003 |
| WO | WO-03/087763 A2 | 10/2003 |
| WO | WO-03/099992 A2 | 12/2003 |
| WO | WO-03/106657 A2 | 12/2003 |
| WO | WO-2004/041277 A1 | 5/2004 |
| WO | WO-2004/047747 A2 | 6/2004 |
| WO | WO-2004/062621 A2 | 7/2004 |
| WO | WO-2004/082608 A2 | 9/2004 |
| WO | WO-2004/100874 A2 | 11/2004 |
| WO | WO-2005/003158 A2 | 1/2005 |
| WO | WO-2005/014650 A2 | 2/2005 |
| WO | WO-2005/023311 A2 | 3/2005 |
| WO | WO-2005/041857 A2 | 5/2005 |
| WO | WO-2005/113012 A2 | 12/2005 |
| WO | WO-2005/118636 A2 | 12/2005 |
| WO | WO-2006/098887 A2 | 9/2006 |
| WO | WO-2006/102070 A2 | 9/2006 |
| WO | WO-2006/119062 A2 | 11/2006 |
| WO | WO-2006/119107 A2 | 11/2006 |
| WO | WO-2006/124708 A1 | 11/2006 |
| WO | WO-2006/135734 A2 | 12/2006 |
| WO | WO-2007/080129 A1 | 7/2007 |
| WO | WO-2008/061013 A2 | 5/2008 |
| WO | WO-2008/133722 A2 | 11/2008 |
| WO | WO-2009/039175 A2 | 3/2009 |
| WO | 2009/047356 A1 | 4/2009 |
| WO | WO-2009/079471 A1 | 6/2009 |
| WO | WO-09/131553 A2 | 10/2009 |
| WO | 2010/115932 A1 | 10/2010 |
| WO | WO-2010/115932 A1 | 10/2010 |
| WO | WO-2011/143307 A1 | 11/2011 |
| WO | WO-2012/058393 A2 | 5/2012 |
| WO | WO-2012/118903 A2 | 9/2012 |
| WO | WO-2012/135035 A1 | 10/2012 |
| WO | WO-2012/145417 A1 | 10/2012 |
| WO | WO-2013/019954 A1 | 2/2013 |
| WO | WO-2013/101451 A1 | 7/2013 |
| WO | 2014/006100 A1 | 1/2014 |
| WO | WO-2014/006100 A1 | 1/2014 |
| WO | WO-2014/081955 A1 | 5/2014 |
| WO | WO-2014/144817 A2 | 9/2014 |
| WO | 2015/087187 A1 | 6/2015 |
| WO | 2016/092101 A1 | 6/2016 |
| WO | WO-2016/092101 A1 | 6/2016 |
| WO | WO-2017/027861 A1 | 2/2017 |
| WO | WO-2017/153541 A1 | 9/2017 |
| WO | WO-2018/031454 A1 | 2/2018 |
| WO | WO-2018/115879 A1 | 6/2018 |
| WO | WO-2018/115880 A1 | 6/2018 |
| WO | WO-2018/170099 A1 | 9/2018 |
| WO | 2019/191150 A1 | 10/2019 |
| WO | 2019/191534 A1 | 10/2019 |
| WO | 2020/033788 A1 | 2/2020 |

OTHER PUBLICATIONS

Roschger, et al, "Effect of Sclerostin Antibody Treatment in a Mouse Model of Severe Osteogenesis Imperfecta," Bone 66 (2014) 182-188.

Sinder, et al, "Rapidly Growing Brtl/+ Moose Model of Osteogenesis Imperfecta Improves Bone Mass and Strength With Sclerostin Antibody Treatment," Bone 71 (2015) 115-123.

MacNabb et al., "Sclerostin Antibody Therapy for the Treatment of Osteoporosis: Clinical Prospects and Challenges", J Osteoporos. 2016;2016:6217286. doi: 10.1155/2016/6217286. Epub May 26, 2016.

Glorieux et al., "BPS804 Anti-Sclerostin Antibody in Adults With Moderate Osteogenesis Imperfecta: Results of a Randomized Phase 2a Trial", J Bone Miner Res. Jul. 2017;32(7):1496-1504. doi: 10.1002/jbmr.3143. Epub Apr. 19, 2017.

Hald et al., Bisphosphonates for the Prevention of Fractures in Osteogenesis Imperfecta: A Meta-Analysis of Placebo Controlled Trials, J. of Bone and Mineral Research, 30(5): 929-933 (2015).

Phillips et al., Chapter 21 "Animal Models of Osteogenesis Imperfecta," in Osteogenesis Imperfecta, A Translation Approach to Brittle Bone Disease, 197-207 (2014).

Yang, Q. et al., A novel variant of osteogenesis of imperfecta type IV and low serum phosphorus level caused by a Val94Asp mutation in COL1A1, Molecular Medicine Reports, 17:4433-4439 (2018).

\* cited by examiner

FIG. 1

| Parameter | | PINP | | PICP | | BSAP | | OC | | BMD | |
|---|---|---|---|---|---|---|---|---|---|---|---|
| | | MOR05813 | Reference | MOR05813 | Reference | MOR05813 | Reference | MOR05813 | Reference | MOR05813 | Reference |
| Baseline | N | 9 | 5 | 9 | 5 | 9 | 5 | 9 | 5 | 9 | 4 |
| | Geometric Mean | 44.89 | 26.99 | 50.02 | 28.41 | 36.48 | 42.80 | 31.31 | 29.24 | 0.77 | 0.82 |
| Day 43 | N | 9 | 5 | 9 | 5 | 9 | 5 | 9 | 5 | | |
| | Geometric Mean | 82.81 | 28.50 | 76.39 | 29.83 | 58.00 | 37.28 | 45.14 | 23.66 | | |
| Day 141 | N | | | | | | | | | 9 | 4 |
| | Geometric Mean | | | | | | | | | 0.80 | 0.82 |
| | Ratio of Geometric Means [90% CI] | 1.84 [1.65, 2.06] | 1.06 [0.83, 1.34] | 1.53 [1.27, 1.84] | 1.05 [0.87, 1.26] | 1.59 [1.36, 1.86] | 0.87 [0.53, 1.42] | 1.44 [1.17, 1.78] | 0.81 [0.48, 1.36] | 1.04 [1.01, 1.07] | 1.01 [1.00, 1.01] |
| | P-value (2-sided) | <.001 | 0.651 | 0.003 | 0.600 | <.001 | 0.582 | 0.012 | 0.436 | 0.038 | 0.138 |

FIG. 2

| Parameter | MOR05813 | | | Reference | | | Ration of geometric means [90% CI] | P-value (1-sided) |
|---|---|---|---|---|---|---|---|---|
| | N | Geometric Mean | | N | Geometric Mean | | | |
| PINP | 9 | 1.84 | | 5 | 1.06 | | 1.75 [1.43, 2.14] | <0.001 |
| PICP | 9 | 1.53 | | 5 | 1.05 | | 1.45 [1.11, 1.90] | 0.014 |
| BSAP | 9 | 1.59 | | 5 | 0.87 | | 1.83 [1.27, 2.62] | 0.006 |
| OC | 9 | 1.44 | | 5 | 0.81 | | 1.78 [1.17, 2.71] | 0.015 |

USE OF ANTI-SCLEROSTIN ANTIBODIES IN THE TREATMENT OF OSTEOGENESIS IMPERFECTA

CROSS-REFERENCE TO RELATED APPLICATIONS

The present invention is filed under 35 U.S.C. § 371 as the U.S. national phase of International Patent Application No. PCT/GB2017/053849, filed Dec. 21, 2017, which designated the United States and which claims priority to U.S. Provisional Application No. 62/437,358 filed Dec. 21, 2016, each of which is hereby incorporated in its entirety including all tables, figures, and claims.

FIELD OF INVENTION

This invention relates to antibodies and their use as pharmaceutical compositions, more specifically to the use of anti-sclerostin antibodies in the treatment of osteogenesis imperfecta.

SEQUENCE LISTING

The instant application contains a Sequence Listing which has been submitted in ASCII format via EFS-Web and is hereby incorporated by reference in its entirety. Said ASCII copy, created on Jun. 13, 2019, is named MERE3-P075833US_SeqListing.txt and is 153 kilobytes in size.

BACKGROUND

Osteogenesis imperfecta (OI) is a rare genetic disorder of the connective tissue characterized by bone fragility and reduced bone mass. OI comprises a group of inherited disorders which primarily, but not always, arise from mutations in the genes encoding type I collagen. About 85% of the cases are linked to mutations in one of the two genes encoding type I collagen (COL1A1 and COL1A2). Clinically, OI is characterized by fragile bones that fracture easily and without any trauma. In addition, patients with OI are often affected by muscle weakness, hearing loss, fatigue, joint laxity, curved bones, scoliosis, blue sclerae, dentinogenesis imperfecta, and short stature.

The clinical classification system divides OI into types I-V. Type I OI patients usually suffer from a mild non-deforming disease that is often associated with a premature stop codon in COL1A1. This defect results in a reduced rate of type I collagen production and quantitatively less collagen in bone. Patients with type II OI usually die during the perinatal period, as a result of respiratory failure from multiple severe fractures that include the rib cage. Types III and IV OI are often associated with glycine substitution in COL1A1 and COL1A2, which is a qualitative defect that prevents the 3 polypeptide chains of type I collagen to intertwine properly to form a normal triple alpha helical structure. Type III OI is the most severe form of OI in those affected children who survive infancy, whereas patients with type IV have mild to moderate bone deformities. Type V is infrequent.

There remains a need for therapeutic methods and agents for the treatment of OI.

BRIEF SUMMARY OF THE INVENTION

The inventors surprisingly found that human patients with osteogenesis imperfecta (OI) can successfully be treated with an anti-sclerostin antibody, as established by the examples, which confirm that the anti-sclerostin antibody BPS804 can both increase bone formation and reduce bone resorption in patients with OI. We disclosed high affinity, neutralizing, fully human anti-sclerostin monoclonal antibodies (collectively "the human anti-sclerostin monoclonal antibody") and their potent in vitro activity and in vivo activity in our U.S. Pat. Nos. 7,879,322, 8,246,953, and 8,486,661, which are hereby incorporated in their entirety by reference thereto.

In one aspect, the present invention is a method for treating osteogenesis imperfecta (OI) in a human patient comprising administering to the human patient a therapeutically effective amount of an anti-sclerostin antibody comprising (a) a heavy chain variable region CDR1 comprising an amino acid sequence set forth in SEQ ID NO:4; (b) a heavy chain variable region CDR2 comprising an amino acid sequence set forth in SEQ ID NO:15; (c) a heavy chain variable region CDR3 comprising an amino acid sequence set forth in SEQ ID NO:26; (d) a light chain variable region CDR1 comprising an amino acid sequence set forth in SEQ ID NO:37; (e) a light chain variable region CDR2 comprising an amino acid sequence set forth in SEQ ID NO:48; and (f) a light chain variable region CDR3 comprising an amino acid sequence set forth in SEQ ID NO:59. This anti-sclerostin antibody is also referred to herein as 'the antibody of the invention' The anti-sclerostin antibody of the invention is administered intravenously at a dose of 1-50 mg per kg body weight of the human patient.

In one embodiment, the present invention is a method for increasing bone formation and reducing bone resorption in an osteogenesis imperfecta patient by administering to the patient a therapeutically effective amount of the anti-sclerostin antibody of the invention. In another aspect, the invention provides an anti-sclerostin antibody of the invention, for use in the treatment of osteogenesis imperfecta. In one embodiment the anti-sclerostin antibody increases bone formation and/or reduces bone resorption.

In another embodiment, the anti-sclerostin antibody comprises an immunoglobulin heavy chain variable domain (VH) having at least 90 (such as at least 95, 98, or 99 or 100) percent identity to the amino acid sequence set forth in SEQ ID NO: 70. In yet another embodiment, the anti-sclerostin antibody comprises an immunoglobulin light chain variable domain (VL) having at least 90 (such as at least 95, 98, or 99 or 100) percent identity to the amino acid sequence set forth in SEQ ID NO: 81. In still another embodiment, the anti-sclerostin antibody comprises a VH having at least 90 (such as at least 95, 98, or 99 or 100) percent identity to the amino acid sequence set forth in SEQ ID NO: 70, and a VL having at least 90 (such as at least 95, 98, or 99 or 100) percent identity to the amino acid sequence set forth in SEQ ID NO: 81. In yet another embodiment, the anti-sclerostin antibody comprises a VH having the amino acid sequence set forth in SEQ ID NO: 70, and a VL having the amino acid sequence set forth in SEQ ID NO: 81. In yet still another embodiment, the anti-sclerostin antibody comprises a heavy chain having at least 90 (such as at least 95, 98, or 99 or 100) percent identity to the amino acid sequence set forth in SEQ ID NO: 114 or 172, and/or at least 90 (such as at least 95, 98, or 99 or 100) percent identity to a light chain having the amino acid sequence set forth in SEQ ID NO: 125 or 173. In one embodiment, the anti-sclerostin antibody comprises a heavy chain having the amino acid sequence set forth in SEQ ID NO: 172 and a light chain having the amino acid sequence set forth in SEQ ID NO: 173.

In some embodiments, the therapeutically effective amount of the anti-sclerostin antibody of the invention is about 1-50 mg of said antibody per kg body weight of the human patient.

Another aspect of the invention is a pharmaceutical composition for increasing bone formation and reducing bone resorption in an osteogenesis imperfecta patient. In some embodiments, the composition contains an anti-sclerostin antibody comprising: a) at least one immunoglobulin heavy chain variable domain (VH) which comprises in sequence hypervariable regions a heavy chain variable region CDR1, a heavy chain variable region CDR2, and a heavy chain variable region CDR3, said heavy chain variable region CDR1 comprising an amino acid sequence set forth in SEQ ID NO: 4, said heavy chain variable region CDR2 comprising an amino acid sequence set forth in SEQ ID NO: 15, and said heavy chain variable region CDR3 comprising an amino acid sequence set forth in SEQ ID NO: 26; and b) at least one immunoglobulin light chain variable domain (VL) which comprises in sequence hypervariable regions a light chain variable region CDR1, a light chain variable region CDR2, and a light chain variable region CDR3, said light chain variable region CDR1 comprising an amino acid sequence set forth in SEQ ID NO: 37, said light chain variable region CDR2 comprising an amino acid sequence set forth in SEQ ID NO: 48, and said light chain variable region CDR3 comprising an amino acid sequence set forth in SEQ ID NO: 59.

In another embodiment, the anti-sclerostin antibody in the pharmaceutical composition comprises a VH having at least 95 percent identity to the amino acid sequence set forth in SEQ ID NO: 70. In yet another embodiment, the anti-sclerostin antibody comprises a VL having at least 95 percent identity to the amino acid sequence set forth in SEQ ID NO: 81.

In still another embodiment, the anti-sclerostin antibody comprises a VH having at least 95 percent identity to the amino acid sequence set forth in SEQ ID NO: 70, and a VL having at least 95 percent identity to the amino acid sequence set forth in SEQ ID NO: 81. In yet another embodiment, the anti-sclerostin antibody comprises a VH having the amino acid sequence set forth in SEQ ID NO: 70, and a VL having the amino acid sequence set forth in SEQ ID NO: 81. In yet still another embodiment, the anti-sclerostin antibody comprises a heavy chain having the amino acid sequence set forth in SEQ ID NO: 114 or 172, and/or a light chain having the amino acid sequence set forth in SEQ ID NO: 125 or 173.

In one aspect the invention provides a pharmaceutical composition comprising an anti-sclerostin antibody as disclosed herein. In one embodiment the pharmaceutical composition can be used in the methods/uses described herein

BRIEF DESCRIPTION OF THE DRAWINGS

FIG. 1 shows a table with results of the one-sample t-test analysis results for the bone metabolism biomarkers.

FIG. 2 shows a table with results of the two-sample t-test analysis of the bone metabolism biomarkers.

DETAILED DESCRIPTION OF THE INVENTION

Figure 3:
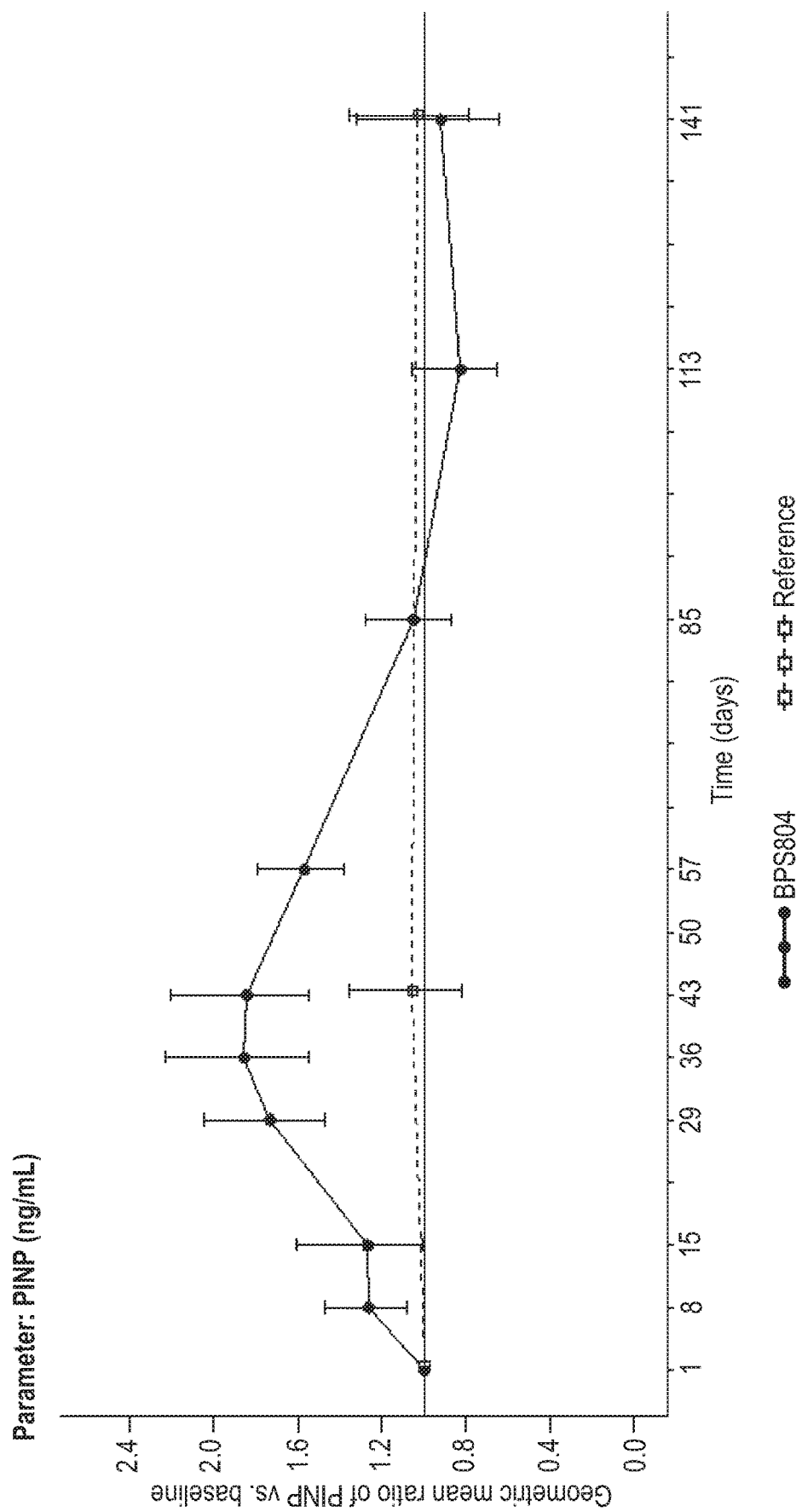
FIG. 3 shows a graph depicting ratios to baseline in geometric means (plus or minus SD) for PINP.
Figure 4:
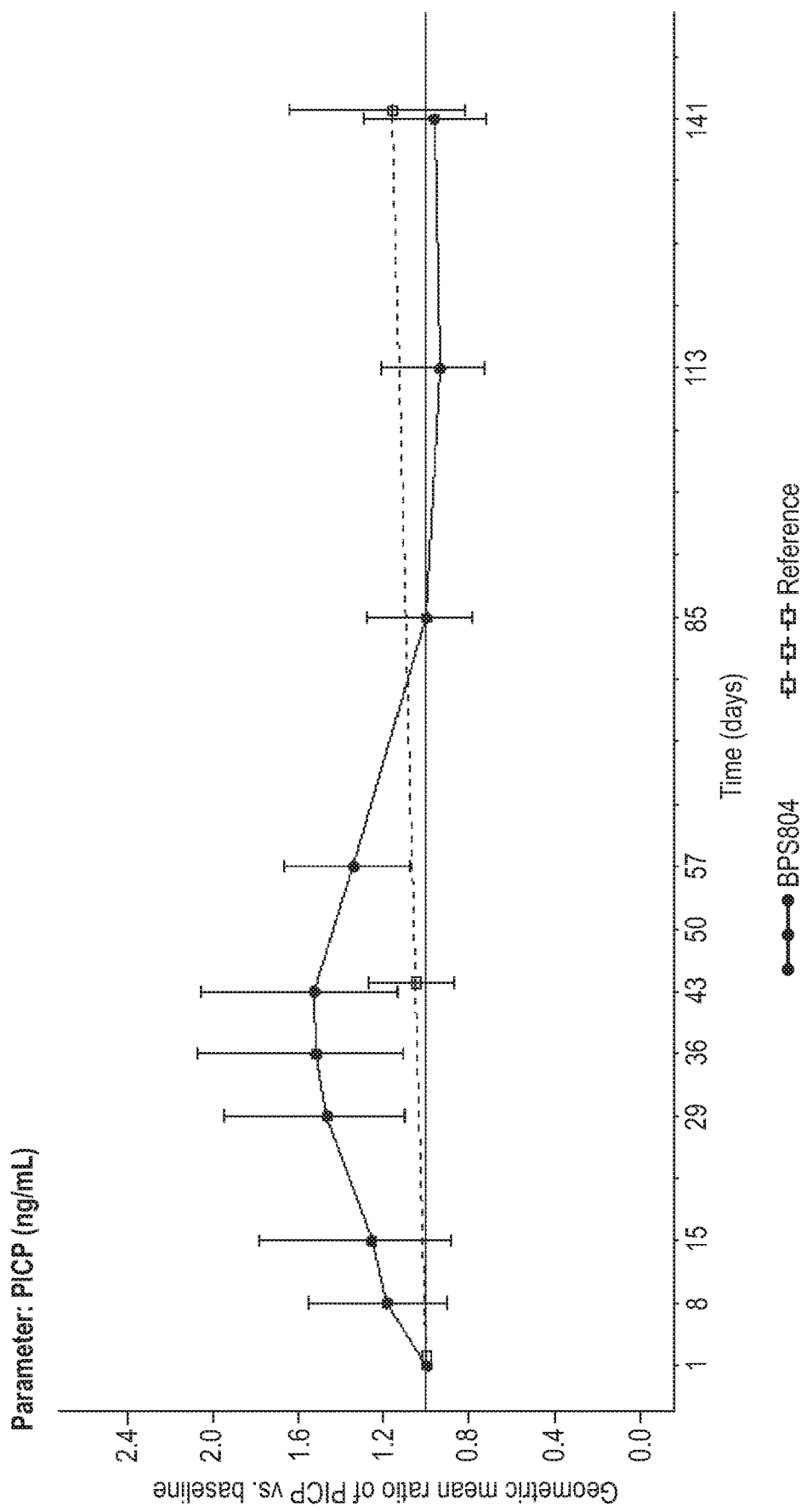
FIG. 4 shows a graph depicting ratios to baseline in geometric means (plus or minus SD) for PICP.
Figure 5:
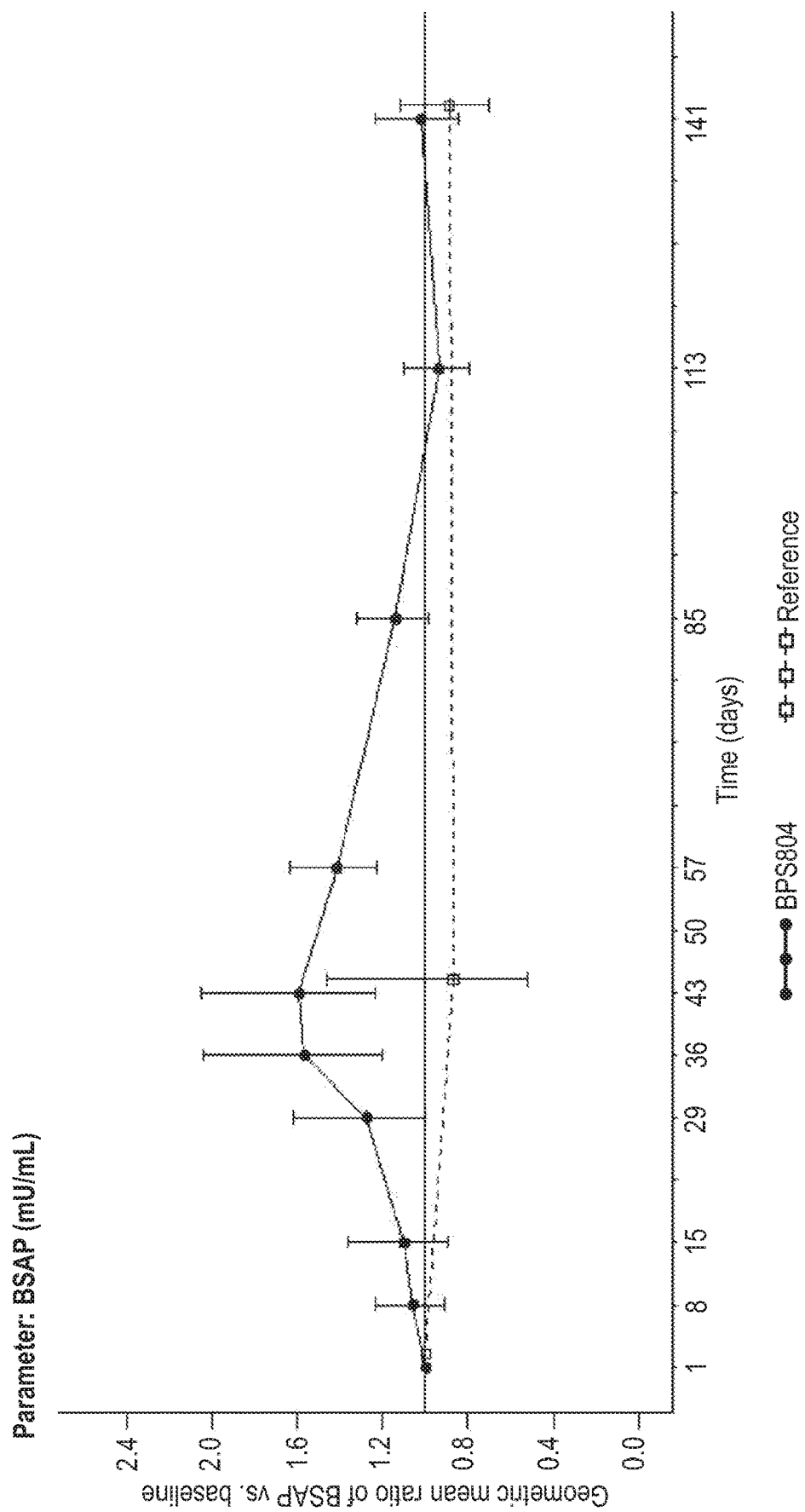
FIG. 5 shows a graph depicting ratios to baseline in geometric means (plus or minus SD) for BSAP.
Figure 6:
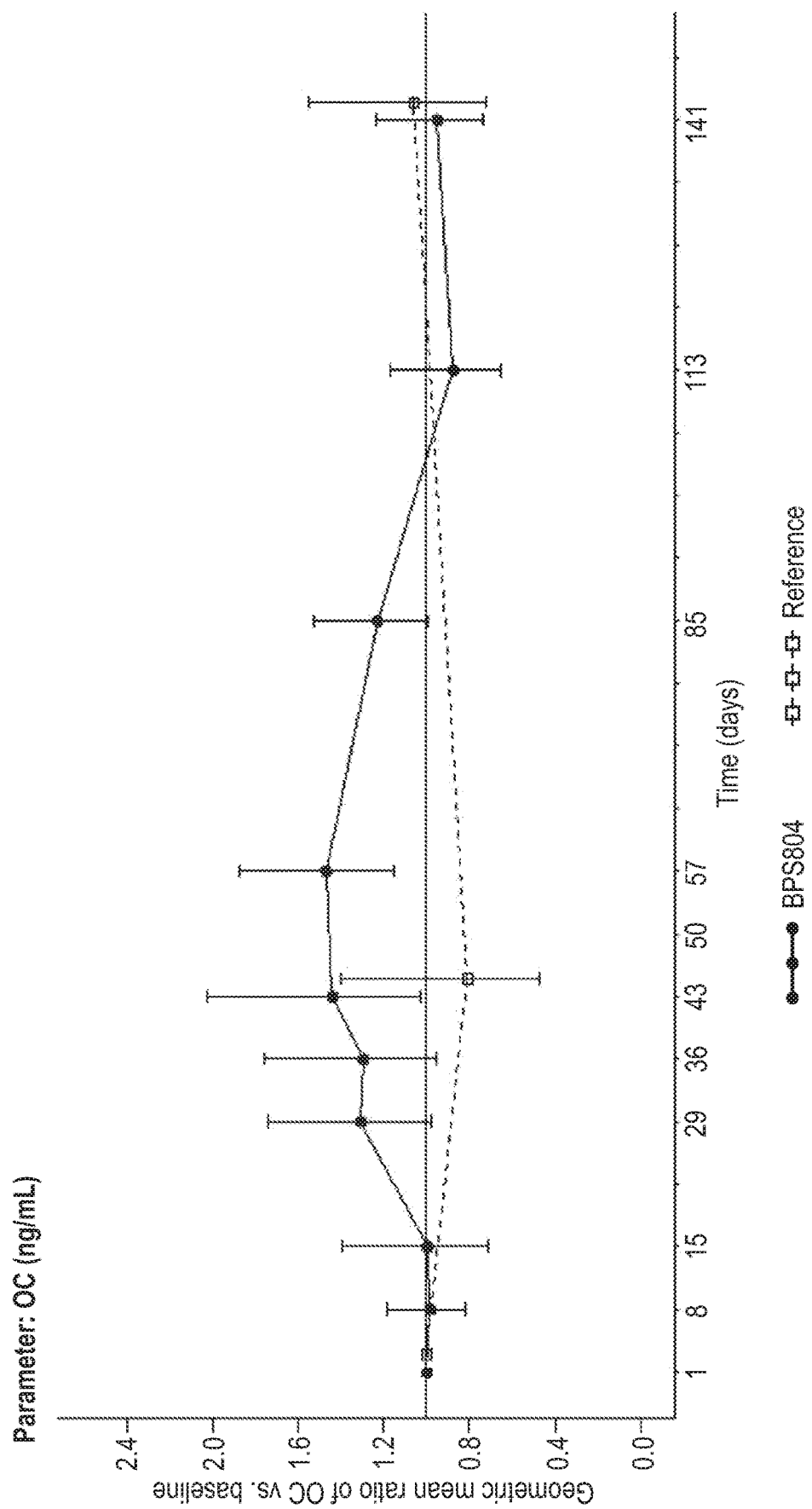
FIG. 6 shows a graph depicting ratios to baseline in geometric means (plus or minus SD) for OC.
Figure 7:
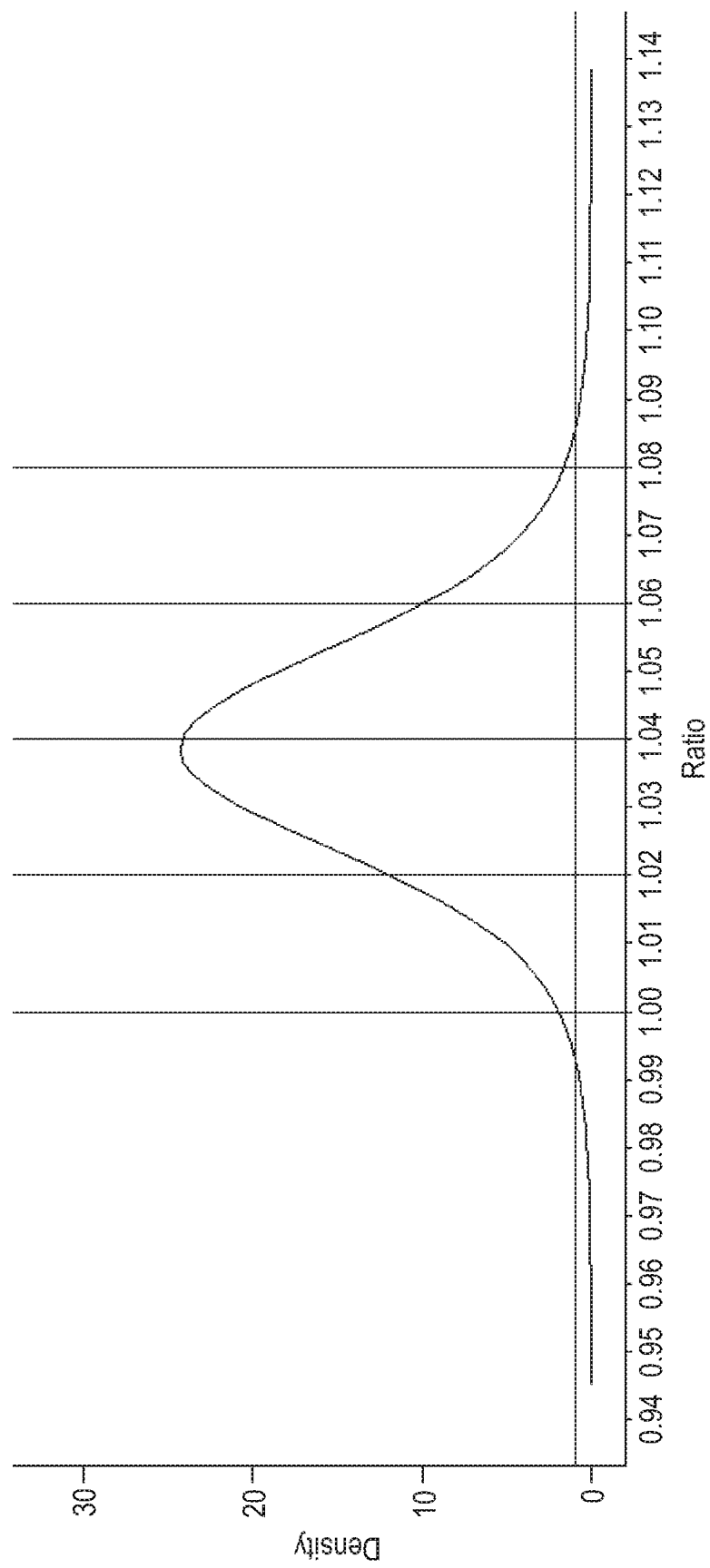
FIG. 7 shows a graph depicting Bayesian posterior probabilities of ratios to baseline for BMD of lumbar spine (measured by DXA) data.

The present invention is based on the unexpected and surprising findings that human patients with osteogenesis imperfecta (OI) can successfully be treated with an anti-sclerostin antibody. Administration of an anti-sclerostin antibody to human OI patients increases bone formation and reduces bone resorption, as shown in the examples.

By way of background, sclerostin is a naturally occurring protein that in humans is encoded by the SOST gene. Sclerostin is a secreted glycoprotein with a C terminal cysteine knot-like (CTCK) domain and sequence similarity to the DAN (differential screening-selected gene aberrative in neuroblastoma) family of bone morphogenetic protein (BMP) antagonists.

As shown for the first time by the present inventors, inhibiting sclerostin with anti-sclerostin antibodies boosts bone formation and density and provides beneficial effects in treating OI in humans. Unlike previous anabolic treatments using GH or PTH which increase bone turnover, a treatment with an anti-sclerostin antibody offers the advantage of stimulating bone formation while inhibiting bone resorption in OI patients. The clinical utility of anti-sclerostin antibodies therefore includes the treatment of osteogenesis imperfecta in humans where bone formation is of therapeutic benefit in a disease characterized by a significant lack of bone matrix.

As such, the invention is directed to methods of using anti-sclerostin antibodies in the treatment of OI, as well as compositions comprising anti-sclerostin antibodies for use in treating OI. In one aspect the invention is concerned with the treatment of osteogenesis imperfecta types I, III or IV. Accordingly, the invention provides anti-sclerostin antibodies and pharmaceutical compositions comprising said antibodies for use in the treatment of OI, preferably OI types I, III or IV. The anti-sclerostin antibody of the invention is a human monoclonal anti-sclerostin antibody.

The methods and uses of the anti-sclerostin antibody in the present invention were unexpected and surprising because the antibody treatment in OI patients results in both an increase of bone formation and a reduction of bone resorption.

In order that the present invention may be more readily understood, certain terms are first defined. Additional definitions are set forth throughout the detailed description.

The term "comprising" encompasses "including" as well as "consisting" e.g. a composition "comprising" X may consist exclusively of X or may include something additional e.g. X+Y.

The term "about" in relation to a numerical value x means, for example, x±10%.

The term sclerostin refers to human sclerostin as defined in SEQ ID NO: 155. Recombinant human sclerostin can be obtained from R&D Systems (Minneapolis, Minn., USA; 2006 cat #1406-ST-025). Additionally, recombinant mouse sclerostin/SOST is commercially available from R&D Systems (Minneapolis, Minn., USA; 2006 cat #1589-ST-025). U.S. Pat. Nos. 6,395,511 and 6,803,453, and U.S. Patent Publications 20040009535 and 20050106683 refer to anti-sclerostin antibodies in general.

The term "antibody" as referred to herein includes whole antibodies and any antigen binding fragment (i.e., "antigen-binding portion") or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. In one embodiment, reference to an antibody herein embraces isolated, monoclonal, human and humanized monoclonal antibodies.

The term "antigen-binding portion" of an antibody (or simply "antigen portion"), as used herein, refers to full length or one or more fragments of an antibody that retain the ability to specifically bind to an antigen (e.g., sclerostin). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the VL, VH, CL and CH1 domains; a F(ab)$_2$ fragment, a bivalent fragment comprising two Fab fragments linked by a disulfide bridge at the hinge region; a Fd fragment consisting of the VH and CH1 domains; a Fv fragment consisting of the VL and VH domains of a single arm of an antibody; a dAb fragment (Ward et al., 1989 Nature 341: 544-546), which consists of a VH domain; and an isolated complementarity determining region (CDR).

Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al., 1988 Science 242:423-426; and Huston et al., 1988 Proc. Natl. Acad. Sci. 85:5879-5883). Such single chain antibodies are also intended to be encompassed within the term "antigen-binding region" of an antibody. These antibody fragments are obtained using conventional techniques known to those of skill in the art, and the fragments are screened for utility in the same manner as are intact antibodies.

An "isolated antibody", as used herein, refers to an antibody that is substantially free of other antibodies having different antigenic specificities (e.g., an isolated antibody that specifically binds sclerostin is substantially free of antibodies that specifically bind antigens other than sclerostin). An isolated antibody that specifically binds sclerostin may, however, have cross-reactivity to other antigens, such as sclerostin molecules from other species. Moreover, an isolated antibody may be substantially free of other cellular material and/or chemicals. In one embodiment, reference to an antibody herein means an isolated antibody.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis as described in Knappik, et al. (2000. J Mol Biol 296, 57-86).

The human antibodies may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

In one embodiment, and as used herein, an antibody that binds sclerostin (e.g. an anti-sclerostin antibody) means that it specifically binds to sclerostin polypeptide. "Specifically binds to sclerostin polypeptide" is intended to refer to an antibody that binds to sclerostin polypeptide with a $K_D$ of $1 \times 10^{-8}$ M or less, $1 \times 10^{-9}$ M or less, or $1 \times 10^{-10}$ M or less. The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a Biacore® system.

Standard assays to evaluate the binding ability of the antibodies toward sclerostin of various species are known in the art, including for example, ELISAs, western blots and RIAs. Suitable assays are described in detail in WO2009/047356. The binding kinetics (e.g., binding affinity) of the antibodies also can be assessed by standard assays known in the art, such as by Biacore analysis. Assays to evaluate the effects of the antibodies on functional properties of sclerostin (e.g., receptor binding, preventing or ameliorating osteolysis) are described in further detail in WO2009/047356.

As used herein, the percent identity between two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the)(BLAST program (version 2.0) of Altschul, et al., 1990 J. Mol. Biol. 215:403-10. BLAST protein searches can be performed with the XBLAST program, score=50, word-length=3 to obtain amino acid sequences homologous to the antibody molecules of the invention. To obtain gapped alignments for comparison purposes, Gapped BLAST can be utilized as described in Altschul et al., 1997 Nucleic Acids Res. 25(17):3389-3402. When utilizing BLAST and Gapped BLAST programs, the default parameters of the respective programs (e.g., XBLAST and NBLAST) can be used. See http:www.ncbi.nhn.nih.gov.

Various aspects of the invention are described in further detail in the following subsections.

Methods of Treatment with and Uses of Anti-Sclerostin Antibodies in OI Treatment In one aspect, the invention is directed to methods of treating OI patients with anti-sclerostin antibodies as described herein or uses of these anti-sclerostin antibodies in OI treatment. The treatment with anti-sclerostin antibodies may both increase bone formation and reduce bone resorption in the OI patients. In one aspect, the invention provides an anti-sclerostin antibody for use in the treatment of OI. Suitable anti-sclerostin antibodies for use in the treatment of OI are disclosed herein.

In some embodiments, the invention is a method for increasing bone formation and reducing bone resorption in an OI patient and the method comprises administering to the patient a therapeutically effective amount of an anti-sclerostin antibody. In one embodiment, treatment of an OI patient with an anti-sclerostin antibody of the invention increases bone formation and/or reduces bone resorption in said OI patient.

The anti-sclerostin antibody of the invention comprises: a heavy chain variable region CDR1 of SEQ ID NO: 4; a heavy chain variable region CDR2 of SEQ ID NO: 15; a heavy chain variable region CDR3 of SEQ ID NO: 26; a light chain variable region CDR1 of SEQ ID NO: 37; a light chain variable region CDR2 of SEQ ID NO: 48; and a light chain variable region CDR3 of SEQ ID NO: 59. In one embodiment, the CDR regions are delineated using the Kabat system (Kabat, E. A., et al., 1991 Sequences of Proteins of Immunological Interest, Fifth Edition, U.S. Department of Health and Human Services, NIH Publication No. 91-3242).

In a certain embodiment, the anti-sclerostin antibody comprises: a VH polypeptide amino acid sequence having at least 95 percent identity to the amino acid sequence set forth as SEQ ID NO: 70.

In a certain embodiment, the anti-sclerostin antibody comprises: a VL polypeptide amino acid sequence having at least 95 percent identity to the amino acid sequence set forth as SEQ ID NO: 81.

In a certain embodiment, the anti-sclerostin antibody comprises: a VH polypeptide amino acid sequence having at least 95 percent identity to the amino acid sequence set forth as SEQ ID NO: 70 and a VL polypeptide amino acid sequence having at least 95 percent identity to the amino acid sequence set forth as SEQ ID NO: 81.

In a certain embodiment, the anti-sclerostin antibody comprises: the VH polypeptide amino acid sequence set forth as SEQ ID NO: 70 and the VL polypeptide amino acid sequence set forth as SEQ ID NO: 81.

In a certain embodiment, the anti-sclerostin antibody comprises: the heavy chain polypeptide amino acid sequence set forth as SEQ ID NO: 114 or 172 and the light chain polypeptide amino acid sequence set forth as SEQ ID NO: 125 or 173.

In a preferred embodiment, the anti-sclerostin antibody is the antibody BPS804, which is a human anti-sclerostin monoclonal antibody. BPS804 comprises the following CDRs: heavy chain variable region CDR1 of SEQ ID NO: 4; heavy chain variable region CDR2 of SEQ ID NO: 15; heavy chain variable region CDR3 of SEQ ID NO: 26; light chain variable region CDR1 of SEQ ID NO: 37; light chain variable region CDR2 of SEQ ID NO: 48; and light chain variable region CDR3 of SEQ ID NO: 59. The VH and VL sequences of BPS804 comprise: the VH polypeptide amino acid sequence set forth as SEQ ID NO: 70 and the VL polypeptide amino acid sequence set forth as SEQ ID NO: 81. The heavy and light chain sequences of BPS804 comprise: the heavy chain polypeptide amino acid sequence set forth as SEQ ID NO: 172 and the light chain polypeptide amino acid sequence set forth as SEQ ID NO: 173.

Additional characteristics of the anti-sclerostin antibodies of the present invention, such as BPS804 are described in WO2009/047356, which disclosure, discussion and data is hereby incorporated by reference thereto. By way of example only, the antibodies of the invention may exhibit at least one of the following functional properties: the antibody blocks the inhibitory effect of sclerostin in a cell based wnt signaling assay, the antibody blocks the inhibitory effect of sclerostin in a cell based mineralization assay, the antibody blocks the inhibitory effect of sclerostin in Smad1 phosphorylation assay, the antibody inhibits binding of sclerostin to the LRP-6, and the antibody increases bone formation and mass and density. As noted above, these properties are described in detail in WO2009/047356.

In relation to an antibody that "blocks the inhibitory effect of sclerostin in a cell based wnt signaling assay", this is intended to refer to an antibody that restores wnt induced signaling in the presence of sclerostin in a cell-based super top flash (STF) assay with an IC50 less than 1 mM, 100 nM, 20 nM, 10 nM or less. WO2009/047356 describes said wnt STF assay.

In relation to an antibody that "blocks the inhibitory effect of sclerostin in a cell based mineralization assay", this is intended to refer to an antibody that restores BMP2 induced mineralisation in the presence of sclerostin in a cell-based assay with an IC50 less than 1 mM, 500 nM, 100 nM, 10 nM, 1 nM or less.

In relation to an antibody that "blocks the inhibitory effect of sclerostin in Smad1 phosphorylation assay", this is intended to refer to an antibody that restores BMP6 induced Smad1 phosphorylation in the presence of sclerostin in a cell based assay with an IC50 less than 1 mM, 500 nM, 100 nM, 10 nM, 1 nM or less.

In relation to an antibody that "inhibits binding of sclerostin to the LRP-6", this is intended to refer to an antibody that inhibits sclerostin binding to LRP-6 with a IC50 of 1 mM, 500 nM, 100 nM, 10 nM, 5 nM, 3 nM, 1 nM or less.

In relation to an antibody that "increases bone formation and mass and density", this is intended to refer to an antibody that is capable of reaching bone formation, mass and density at the level of daily intermittent treatment with high anabolic dose of PTH, such as a daily intermittent treatment with 100 µg/kg of hPTH.

In one embodiment, the anti-sclerostin antibody of the invention increases bone formation and/or reduces bone resorption.

Dosage Regimen

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals. In one embodiment, the dosage unit form of the invention comprises 10-5000 mg of anti-sclerostin antibody, or 10-4000 mg, 10-3000 mg, 10-2000 mg, 10-1000 mg, 10-500 mg, 10-400 mg, 10-300 mg, 10-200 mg, 10-150 mg, 10-100 mg, 10-80 mg, 10-60 mg, 10-50 mg, 10-40 mg, 10-35 mg, 10-30 mg, 10-25 mg, 10-20 mg, or 10-15 mg. In one embodiment, the dosage unit form comprises 150 mg of anti-sclerostin antibody.

In one embodiment, the anti-sclerostin antibody of the dosage unit form is in a lyophilized state which may be in powder form. In another embodiment, the anti-sclerostin antibody of the dosage unit form is in solution. In one embodiment the dosage unit form of the invention is contained within a container such as a vial. In another embodiment, the container is a syringe.

In addition to the active substance (i.e. the anti-sclerostin antibody), the dosage unit form may comprise one or more additional substances and/or excipients. In one embodiment, the dosage unit form comprises one or more of the following: sucrose, arginine hydrochloride, L-histidine, polysorbate 80, hydrochloric acid and water for injection (wfi).

In one aspect, the invention provides a kit comprising an anti-sclerostin antibody of the invention or a pharmaceutical composition of the invention, or a lyophilizate of the invention, or a dosage unit form of the invention. Optionally the kit may further comprise instructions in the form of e.g. a patient information leaflet, instructions for reconstitution of the lyophilizate, and/or administration instructions. In one embodiment, the kit includes a syringe comprising one or more therapeutically effective doses of the anti-sclerostin antibody. The anti-sclerostin antibody in the syringe can be present in liquid or lyophilized form. The kit may further comprise a solution for reconstitution of the lyophilizate, and/or an infusion solution (e.g. dextrose 5% in sterile water).

For administration of the anti-sclerostin antibody, the dosage ranges from about 1 milligram of said antibody per kilogram body weight of the patient (herein referred to as "mg/kg" throughout this application) to 50 mg/kg, more usually about 1 to 30 mg/kg, and still more usually about 1 to 20 mg/kg. For example dosages can be about 5 mg/kg body weight, about 10 mg/kg body weight, about 20 mg/kg body weight, or within the range of about 5-20 mg/kg.

In another aspect of the invention, the anti-sclerostin antibody is administered at a dose of 1-50 mg per kg body weight of a patient, such as at 2-50, 3-50, 5-50, 8-50 mg/kg.

In one embodiment, the anti-sclerostin antibody is administered at a dose of 2-50 mg per kg body weight of a patient, such as at 2-45, 2-40, 2-35, 2-30 mg/kg.

In one embodiment, the anti-sclerostin antibody is administered at a dose of 3-50 mg per kg body weight of a patient, such as at 3-45, 3-40, 3-35, 3-30 mg/kg.

In one embodiment, the anti-sclerostin antibody is administered at a dose of 5-50 mg per kg body weight of a patient, such as at 5-45, 5-40, 5-35, 5-30 mg/kg.

In one embodiment, the anti-sclerostin antibody is administered at a dose of 8-50 mg per kg body weight of a patient, such as at 8-45, 8-40, 8-35, 8-30 mg/kg.

In one embodiment, the anti-sclerostin antibody is administered at a dose of 10-50 mg per kg body weight of a patient, such as at 10-45, 10-40, 10-35, 10-30 mg/kg.

In one embodiment, the anti-sclerostin antibody is administered at a dose of 11-50 mg per kg body weight of a patient, such as at 11-45, 11-40, 11-35, 11-30 mg/kg.

In one embodiment, the anti-sclerostin antibody is administered at a dose of 12-50 mg per kg body weight of a patient, such as at 12-45, 12-40, 12-35, 12-30 mg/kg.

In one embodiment, the anti-sclerostin antibody is administered at a dose of 15-50 mg per kg body weight of a patient, such as at 15-45, 15-40, 15-35, 15-30 mg/kg.

In one embodiment, the anti-sclerostin antibody is administered at a dose of 18-50 mg per kg body weight of a patient, such as at 18-45, 18-40, 18-35, 18-30 mg/kg.

In one embodiment, the anti-sclerostin antibody is administered at a dose of 20-50 mg per kg body weight of a patient, such as at 20-45, 20-40, 20-35, 20-30 mg/kg.

In one embodiment, the anti-sclerostin antibody is administered at a dose of 5-20 mg per kg body weight of a patient, such as at 8-20, 10-20, 12-20, 15-20 mg/kg.

In one embodiment, the anti-sclerostin antibody is administered at a dose of 10 mg per kg body weight of a patient, or at 1, 2, 3, 4, 5, 6, 7, 8, 9 mg/kg.

In one embodiment, the anti-sclerostin antibody is administered at a dose of 20 mg per kg body weight of a patient, or at 11, 12, 13, 14, 15, 17, 18, 19 mg/kg.

In one embodiment, the anti-sclerostin antibody is administered at a dose of 30 mg per kg body weight of a patient, or at 21, 22, 23, 24, 25, 26, 27, 28, 29 mg/kg.

In one embodiment, the anti-sclerostin antibody is administered at a dose of 10 mg per kg body weight of a patient. In a related embodiment, the anti-sclerostin antibody is administered at a dose of 8-12 mg/kg, or at 8-15 mg/kg.

In one embodiment, the anti-sclerostin antibody is administered at a dose of or 20 mg per kg body weight of a patient. In a related embodiment, the anti-sclerostin antibody is administered at a dose of 18-22 mg/kg, or at 15-25 mg/kg.

In another aspect of the invention, the anti-sclerostin antibody is administered at a dose of 10-5000 mg. In one embodiment, the anti-sclerostin antibody is administered at a dose of 10-4000 mg, 10-3000 mg, 10-2000 mg, 10-1000 mg, 10-500 mg, 10-400 mg, 10-300 mg, 10-200 mg, 10-150 mg, 10-100 mg, 10-80 mg, 10-60 mg, 10-50 mg, 10-40 mg, 10-35 mg, 10-30 mg, 10-25 mg, 10-20 mg, or 10-15 mg. In one embodiment, the anti-sclerostin antibody is administered at a dose of 10-3500 mg. In one embodiment, the anti-sclerostin antibody is administered at a dose of 10-3000 mg. In one embodiment, the anti-sclerostin antibody is administered at a dose of 10-2000 mg. In one embodiment, the anti-sclerostin antibody is administered at a dose of 10-1500 mg. In one embodiment, the anti-sclerostin antibody is administered at a dose of 10-1000 mg.

An exemplary treatment regime entails administration of multiple doses, which may be of the same dosage or different dosages ranging from, e.g., about 5-20 mg/kg, under a dosing schedule of once per week, once every two weeks, once every three weeks, once every four weeks, once a month or monthly, once every five weeks, once every six weeks, once every seven weeks, once every eight weeks, once every two months (i.e. bi-monthly), once every three months (i.e. quarterly), once every three to six months, semi-annually, or annually. In some embodiments, the multiple doses can be 2-20 doses, more usually 2-10 doses, and still more usually 3-5 doses, and still further more usually 3 doses under a dosing schedule of once per week, once every two weeks, once every three weeks, once every four weeks, once a month or monthly, once every five weeks, once every six weeks, once every seven weeks, once every eight weeks, once every two months (i.e. bi-monthly), once every three months, once every three to six months, semi-annually, or annually.

In another aspect of the invention, the anti-sclerostin antibody may be administered to a patient on a daily, weekly, bi-weekly, monthly, bi-monthly, quarterly or annual basis.

In one embodiment, the anti-sclerostin antibody is administered to a patient on a weekly basis. In another embodiment, administration occurs every 2, 3, 4, 5, 6, or 7 weeks.

In one embodiment, the anti-sclerostin antibody is administered to a patient on a monthly basis. In another embodiment, administration occurs every 2, 3, 4, 5 or 6 months.

In one embodiment, the anti-sclerostin antibody is administered to a patient every three months (i.e. on a quarterly basis). In the event of more frequent administration regimens, such as weekly or daily administration, an administration route that allows patients to self-administer is preferred. By way of example, a subcutaneous, topical or oral administration route may facilitate self-administration of the anti-sclerostin antibody and preclude visits to a doctor/hospital in order to receive treatment.

Another exemplary treatment regime entails administration of multiple doses, which may be of the same dosage or different dosages ranging from, e.g., about 5-20 mg/kg, until a treatment target is achieved or reached in the patient. The treatment target is achieved or reached after a certain number of doses are administered. The treatment target may be a complete normalization of bone mineral density, a partial normalization of bone mineral density, or a reduced frequency of bone fracture incidence, an increased level of bone formation markers, or a decreased level of bone resorption markers. Thus, in one embodiment, the invention provides an anti-sclerostin antibody for use in the treatment of OI, wherein the anti-sclerostin antibody reduces the fracture rate in a patient/patient population compared to a control patient/patient population. Preferably, the anti-sclerostin antibody reduces the fracture rate by at least 10, 20, 30, 35, 40, 50, 60, 70, 80, or 90 percent. In one embodiment the anti-sclerostin antibody reduces the fracture rate by at least 30 percent. In one embodiment, fractures are defined as peripheral or vertebral fractures (including all major, minor, and vertebral clinical fractures; fractures only detected by means of investigations without clinical symptoms are not included), confirmed by radiologic investigation(s). In one embodiment the fracture rate pertains to a population of patients. The patient population and control patient populations are preferably of a size that allow a statistically significant comparison to be made.

In one aspect of the invention, a treatment regimen entails a first dosing regimen optionally followed by a second dosing regimen. A dosing regimen includes the dose administered and the frequency of administration. These can be selected from any of the aforementioned doses and administration frequencies and can be varied according to the clinical requirements of a patient. The doses and administration frequencies disclosed above are hereby explicitly embraced in this aspect of the invention.

By way of example, in one embodiment, the first dosing regimen is 1-50 mg per kg body weight of a patient, or 2-50 mg/kg, or 3-50 mg/kg, or 5-50 mg/kg, or 8-50 mg/kg, or 3-30 mg/kg, 5-30 mg/kg, or 8-30 mg/kg, or 10-30 mg/kg, or 12-30 mg/kg, or 15-30 mg/kg, or 12-25 mg/kg, or 15-25 mg/kg administered on a monthly basis. In another exemplary embodiment, the first dosing regimen is 10-5000 mg administered on a monthly basis.

In one embodiment, the first dosing regimen is 1-50 mg per kg body weight of a patient administered on a monthly basis.

In one embodiment, the first dosing regimen is 2-50 mg per kg body weight of a patient administered on a monthly basis.

In one embodiment, the first dosing regimen is 2-30 mg per kg body weight of a patient administered on a monthly basis.

In one embodiment, the first dosing regimen is 3-50 mg per kg body weight of a patient administered on a monthly basis.

In one embodiment, the first dosing regimen is 3-30 mg per kg body weight of a patient administered on a monthly basis.

In one embodiment, the first dosing regimen is 5-30 mg per kg body weight of a patient administered on a monthly basis.

In one embodiment, the first dosing regimen is 5-25 mg per kg body weight of a patient administered on a monthly basis.

In one embodiment, the first dosing regimen is 12-25 mg per kg body weight of a patient administered on a monthly basis.

In one embodiment, the first dosing regimen is 20 mg per kg body weight of a patient administered on a monthly basis.

In another exemplary embodiment, the first dosing regimen is 1-50 mg per kg body weight of a patient, or 2-50 mg/kg, or 3-50 mg/kg, or 5-50 mg/kg, or 8-50 mg/kg, or 8-30 mg/kg, or 10-30 mg/kg, or 12-30 mg/kg, or 15-30 mg/kg, or 12-25 mg/kg, or 15-25 mg/kg administered on a quarterly basis. In another exemplary embodiment, the first dosing regimen is 10-5000 mg administered on a quarterly basis.

In one embodiment, the first dosing regimen is 2-30 mg per kg body weight of a patient administered on a quarterly basis.

In one embodiment, the first dosing regimen is 3-30 mg per kg body weight of a patient administered on a quarterly basis.

In one embodiment, the first dosing regimen is 5-30 mg per kg body weight of a patient administered on a quarterly basis.

In one embodiment, the first dosing regimen is 5-25 mg per kg body weight of a patient administered on a quarterly basis.

In one embodiment, the first dosing regimen is 12-25 mg per kg body weight of a patient administered on a quarterly basis.

In one embodiment, the first dosing regimen is 20 mg per kg body weight of a patient administered on a quarterly basis.

In one embodiment and by way of example only, the second dosing regimen 1-50 mg per kg body weight of a patient, or 2-50 mg/kg, or 3-50 mg/kg, or 5-50 mg/kg, or 8-50 mg/kg, or 3-30 mg/kg, 5-30 mg/kg, or 8-30 mg/kg, or 10-30 mg/kg, or 12-30 mg/kg, or 12-25 mg/kg, or 15-30 mg/kg, or 15-25 mg/kg administered on a monthly basis. In another exemplary embodiment, the second dosing regimen is 10-5000 mg administered on a monthly basis In one embodiment, the second dosing regimen is 1-50 mg per kg body weight of a patient administered on a monthly basis.

In one embodiment, the second dosing regimen is 2-50 mg per kg body weight of a patient administered on a monthly basis.

In one embodiment, the second dosing regimen is 2-30 mg per kg body weight of a patient administered on a monthly basis.

In one embodiment, the second dosing regimen is 3-50 mg per kg body weight of a patient administered on a monthly basis.

In one embodiment, the second dosing regimen is 3-30 mg per kg body weight of a patient administered on a monthly basis.

In one embodiment, the second dosing regimen is 5-30 mg per kg body weight of a patient administered on a monthly basis.

In one embodiment, the second dosing regimen is 5-25 mg per kg body weight of a patient administered on a monthly basis.

In one embodiment, the second dosing regimen is 12-25 mg per kg body weight of a patient administered on a monthly basis.

In one embodiment, the second dosing regimen is 20 mg per kg body weight of a patient administered on a monthly basis.

In another embodiment, the second dosing regimen 1-50 mg per kg body weight of a patient, or 2-50 mg/kg, or 3-50 mg/kg, or 5-50 mg/kg, or 8-50 mg/kg, or 3-30 mg/kg, 5-30 mg/kg, or 8-30 mg/kg, or 10-30 mg/kg, or 12-30 mg/kg, or 12-25 mg/kg, or 15-30 mg/kg, or 15-25 mg/kg administered on a bi-monthly basis. In another exemplary embodiment, the second dosing regimen is 10-5000 mg administered on a bi-monthly basis.

In one embodiment, the second dosing regimen is 1-50 mg per kg body weight of a patient administered on a bi-monthly basis.

In one embodiment, the second dosing regimen is 2-50 mg per kg body weight of a patient administered on a bi-monthly basis.

In one embodiment, the second dosing regimen is 2-30 mg per kg body weight of a patient administered on a bi-monthly basis.

In one embodiment, the second dosing regimen is 3-50 mg per kg body weight of a patient administered on a bi-monthly basis.

In one embodiment, the second dosing regimen is 3-30 mg per kg body weight of a patient administered on a bi-monthly basis.

In one embodiment, the second dosing regimen is 5-30 mg per kg body weight of a patient administered on a bi-monthly basis.

In one embodiment, the second dosing regimen is 5-25 mg per kg body weight of a patient administered on a bi-monthly basis.

In one embodiment, the second dosing regimen is 12-25 mg per kg body weight of a patient administered on a bi-monthly basis.

In one embodiment, the second dosing regimen is 20 mg per kg body weight of a patient administered on a bi-monthly basis.

In another exemplary embodiment, the second dosing regimen is 1-50 mg per kg body weight of a patient, or 2-50 mg/kg 3-50 mg/kg, or 5-50 mg/kg, or 8-50 mg/kg, or 8-30 mg/kg, or 10-30 mg/kg, or 12-30 mg/kg, or 12-25 mg/kg, or 15-30 mg/kg, or 15-25 mg/kg administered on a quarterly basis. In another exemplary embodiment, the second dosing regimen is 10-5000 mg administered on a quarterly basis.

In one embodiment, the second dosing regimen is 2-30 mg per kg body weight of a patient administered on a quarterly basis.

In one embodiment, the second dosing regimen is 3-30 mg per kg body weight of a patient administered on a quarterly basis.

In one embodiment, the second dosing regimen is 5-30 mg per kg body weight of a patient administered on a quarterly basis.

In one embodiment, the second dosing regimen is 5-25 mg per kg body weight of a patient administered on a quarterly basis.

In one embodiment, the second dosing regimen is 12-25 mg per kg body weight of a patient administered on a quarterly basis.

In one embodiment, the second dosing regimen is 20 mg per kg body weight of a patient administered on a quarterly basis.

In a related embodiment, the first dosing regimen is 20 mg per kg body weight of a patient administered on a monthly basis and the second dosing regimen is 20 mg per kg body weight of a patient administered on a bi-monthly or quarterly basis.

The time period of administration of the first and second dosing regimens can be varied according to the clinical requirements of a patient. Thus, the first dosing regimen is administered for a first time period and the second dosing regimen is administered for a second time period.

Thus, and by way of example, the first and second time periods can be 1 month, 6 months, 12 months or any other time period.

In one embodiment, an anti-sclerostin antibody can be initially administered to a patient on a monthly basis for a period of 1 year, followed by administration on a bi-monthly or quarterly basis for a period of at least 1 year (such as 2 or more years).

Thus, in one embodiment, the first dosing regimen can be 20 mg per kg body weight of a human patient administered on a monthly basis for a period of 1 year, and the second dosing regimen can be 20 mg per kg body weight of a human patient administered on a bi-monthly or quarterly basis for a period of at least 1 year (such as 2 or more years).

Off-drug periods i.e. periods in which the anti-sclerostin antibody is not administered are also contemplated by the present invention, depending on the clinical requirements of the patient. Thus, in one embodiment the treatment with the anti-sclerostin antibody is discontinued for one or more (such as 2, 3, 4, 5, 6, 8, 10, 12 or more) months or even one or more years.

Measurements of the targets are known in the art. For example, bone mineral density may be measured by dual-energy x-ray absorptiometry (DXA), single-energy x-ray absorptiometry (SXA), quantitative computed tomography (CT), and ultrasound. DXA is an x-ray technique that has become the standard for measuring bone density in the art. Though it can be used for measurements of any skeletal site, clinical determinations are usually made of the lumbar spine and hip. Portable DXA machines have been developed that measure the heel (calcaneus), forearm (radius and ulna), or finger (phalanges), and DXA can also be used to measure body composition. Consequently, it has become standard practice to relate the results to "normal" values using T-scores, which compare individual results to those in a young population that is matched for race and gender. Alternatively, Z-scores compare individual results to those of an age-matched population that is also matched for race and gender. Thus, for example, a 60-year-old woman with a Z-score of −1 (1 SD below mean for age) could have a T-score of −2.5 (2.5 SD below mean for a young control group).

Yet another exemplary treatment regime entails administration of multiple doses, which may be of the same dosage or different dosages ranging from, e.g., about 5-20 mg/kg, for a long term use without a specific timeline to stop the administration. This may be the treatment regime to follow when a dose is needed to maintain an improved symptom in a continuous basis.

In other embodiments, dosage regimens for the anti-sclerostin antibody include three doses at the same dosage, e.g., at 5 mg/kg body weight, 10 mg/kg body weight, or 20 mg/kg body weight by intravenous administration sequentially with an interval of 1-3 weeks, preferably 2 weeks between two consecutive doses. In other embodiments, dosage regimens for the anti-sclerostin antibody include three doses at the three different dosages, e.g., first at 5 mg/kg body weight, then 10 mg/kg body weight, and finally 20 mg/kg body weight by intravenous administration sequentially with an interval of 1-3 weeks, preferably 2 weeks between two consecutive doses. In still other embodiments, dosage regimens for the anti-sclerostin antibody include three doses at the three different dosages, e.g., first at 20 mg/kg body weight, then 10 mg/kg body weight, and finally 5 mg/kg body weight by intravenous administration sequentially with an interval of 1-3 weeks, preferably 2 weeks between two consecutive doses.

In some embodiments, the anti-sclerostin antibody of the invention and one or more monoclonal antibodies with different binding specificities are administered simultaneously or sequentially, in which case the dosage of each antibody administered falls within the ranges indicated. In one embodiment the one or more additional monoclonal antibodies are also anti-sclerostin antibodies. Antibody is usually administered on multiple occasions. Intervals between single dosages can be, for example, weekly, monthly, every two months (i.e. bi-monthly) every three months (i.e. quarterly) or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml. In one embodiment, dosage of anti-sclerostin antibody of the invention is adjusted to achieve a plasma antibody concentration of about 1-1000 µg/ml or about 25-300 µg/ml.

Alternatively, in some embodiments, the anti-sclerostin antibody of the invention can be administered to OI patients as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated or until the patient shows partial or complete amelioration of symptoms of disease. Thereafter, the patient can be administered a prophylactic regime.

In some embodiments, actual dosage levels of the anti-sclerostin antibody may be varied so as to obtain an amount of the anti-sclerostin antibody which is effective to achieve the desired therapeutic response for a particular OI patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular anti-sclerostin antibody being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective amount" of the anti-sclerostin antibody may result in a decrease in severity of disease symptoms, an increase in frequency and duration of disease symptom-free periods, or a prevention of impairment or disability due to the disease affliction.

A composition of the anti-sclerostin antibody can be administered intravenously using one or more of a variety of methods known in the art. Administration for antibodies of the invention occurs via the intravenous route. In one embodiment, administration occurs intravenously by way of an infusion.

The anti-sclerostin antibody can be prepared with carriers that may protect the compound against rapid release, such as a controlled release formulation. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Patient Group

In one embodiment, the methods and uses described herein are for treating osteogenesis imperfecta using anti-sclerostin antibodies described herein. OI is classified by the genetics and severity of disease, and can be classified as type I OI, type II OI, type III OI, type IV OI, or type V OI according to the classification of Van Dijk and Sillence (2014, Am J Med Genet Part A 164A:1470-1481 and Van Dijk and Sillence, 2014, Am J Med Genet Part A 167A:1178; which are incorporated in their entirety by reference thereto). Classification relies on a combination of clinical evaluation/diagnosis, biochemical analysis as well as molecular genetic testing, and is routine for those skilled in the art. The OI nomenclature as used herein is as proposed by Van Dijk and Sillence, as referenced in the publications above.

In 80%-90% of people with OI, OI is caused by mutations in the COL1A1 and COL1A2 genes (17q21.33 and 7q22.3, respectively) encoding the alpha 1 and alpha 2 chains of type-I collagen. A comprehensive database of over 1000 known mutations has been published along with a genotype-phenotype correlation (https://oi.gene.le.ac.uk/home.php; accessed 12 Dec. 2016). Mutations in other genes, such as CRTAP, LEPRE1 or PPIB, are also known. Molecular genetic tests for mutations in i.a. the COL1A1 and COL1A2 genes are known and routine for those skilled in the art. By way of example, Korkko et al. (1998) describe PCR amplification of the COL1A1 gene and the COL1A2 genes followed by mutation scanning by conformation-sensitive gel electrophoresis (CSGE) (Am. J. Hum. Genet. 62:98-110, 1998). van Dijk et al. (2010) describe COL1A1 mutation detection by a multiplex ligation-dependent probe amplification (MLPA) technique (Genet Med 12(11):736-741). More recently, Árvai, K. et al. (2016) describe next-generation sequencing methods (Sci. Rep. 6, 28417). These references are hereby incorporated by reference thereto.

In one embodiment, the methods and uses described herein are for treating patients who exhibit a deficiency of type-I collagen, e.g. OI types I-IV. As a result, the normal architecture of bone, consisting of collagen fibrils and hydroxyapatite crystals, is altered and causes brittleness. In one embodiment, the methods and uses herein are for treating human OI patients characterized by one or more mutations in COL1A1 and/or COL1A2.

In one embodiment, the methods and uses described herein are for treating OI type I, III and/or IV. In one embodiment, OI type I, III and IV are confirmed by DNA testing i.e. detection of COL1A1/COL1A2 mutations. Thus, in one embodiment the methods and uses herein are for treating OI type I, III and/or IV characterized by one or more mutations in COL1A1 and/or COL1A2.

In some embodiments, the methods and uses of the anti-sclerostin antibody of the invention are for treating a mild to moderate form of OI. In other embodiments of the methods and uses of the anti-sclerostin antibody, the patient under treatment has a type I OI, a type II OI, a type III OI, or a type IV OI. In still other embodiments of the methods and uses of the anti-sclerostin antibody, the OI patients are adult patients aged 18 and above. In yet still other embodiments of the methods and uses of the anti-sclerostin antibody, the OI patients are pediatric patients. Pediatric patients as defined herein embraces children aged 0-17 such as those aged 2-17, 3-17, 4-17 or 5-17. The term patients, as used herein, means human patients.

Pharmaceutical Compositions

In another aspect, the present invention provides a pharmaceutical composition for increasing bone formation and reducing bone resorption in a patient suffering from osteogenesis imperfecta, which composition contains the anti-sclerostin antibody as described above. The pharmaceutical composition may be formulated with a pharmaceutically acceptable carrier. In one aspect, the invention provides a pharmaceutical composition comprising an anti-sclerostin antibody as disclosed herein. In one embodiment, the pharmaceutical composition comprising the anti-sclerostin antibody is for use in treating OI.

As used herein, "pharmaceutically acceptable carrier" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g., by injection or infusion). Depending on the route of administration, the anti-sclerostin antibody, may be coated in a material to protect the compound from the action of acids and other natural conditions that may inactivate the compound.

These compositions may also contain adjuvants such as preservatives, wetting agents, emulsifying agents and dispersing agents. Prevention of presence of microorganisms may be ensured both by sterilization procedures, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as, aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the methods of preparation are vacuum drying and freeze-drying (lyophilization) that yield a powder of the active ingredient plus any additional desired ingredient from a previously sterile-filtered solution thereof. Thus, in one embodiment, the anti-sclerostin antibody of the invention/pharmaceutical composition of the invention is formulated as a lyophilizate powder. In a related embodiment, the lyophilizate is reconstituted prior to administration. Suitable liquids for reconstitution include water for injection (wfi).

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, from about 0.1 percent to about 70 percent, or from about 1 percent to about 30 percent of active ingredient in combination with a pharmaceutically acceptable carrier.

Pharmaceutical compositions of the invention and antibodies of the invention may also be administered in a combination therapy, i.e., combined with other active agents. For example, the combination therapy can include an anti-sclerostin antibody of the present invention combined with at least one other anti-inflammatory or anti-osteoporotic agent. Examples of therapeutic agents that can be used in combination therapy include bisphosphonates (such as alendronate, risedronate sodium, ibandronic acid, zoledronic acid, olpadronate, neridronate, skelid, bonefos), parathyroid hormone (e.g. teriparatide (rdna origin) injection), calcilytics, calcimimetics (e.g., cinacalcet), statins, anabolic steroids, lanthanum and strontium salts, and sodium fluoride. Thus, in one embodiment the anti-sclerostin antibodies of the invention can be administered in combination with one or more agents selected from: a calcitonin or an analogue or derivative thereof, e.g. salmon, eel or human calcitonin, calcilytics, calcimimetics (e.g., cinacalcet), a steroid hormone, e.g. an estrogen, a partial estrogen agonist or estrogen-gestagen combination, a SERM (Selective Estrogen Receptor Modulator) e.g. raloxifene, lasofoxifene, bazedoxifene, arzoxifene, FC1271, Tibolone (Livial®), a SARNI (Selective Androgen Receptor Modulator), a RANKL antibody (such as denosumab), a cathepsin K inhibitor, vitamin D or an analogue thereof or PTH, a PTH fragment or a PTH derivative e.g. PTH (1-84) (such as Preos™ (parathyroid hormone 1-84)), PTH (1-34) (such as Forteo™ (teriparatide (rdna origin) injection)), PTH (1-36), PTH (1-38), PTH (1-31)NH2 or PTS 893. According to another embodiment, the antibodies of the invention may be employed in combination with other current osteoporosis therapy approaches, including bisphosphonates (e.g., Fosamax™ (alendronate), Actonel™ (risedronate sodium), Bonviva™ (ibandronic acid), Zometa™ (zoledronic acid), Aclasta™/Reclast™ (zoledronic acid), olpadronate, neridronate, skelid, bonefos), statins, anabolic steroids, lanthanum and strontium salts, and sodium fluoride.

In one embodiment, the antibodies of the invention may be administered in combination with an LRP4 modulating agent, i.e., an agent modulating the expression or activity of LRP4, e.g., an LRP4 neutralizing antibody.

In one embodiment, the antibodies of the invention may be administered in combination with an LRP5 modulating agent, i.e., an agent modulating the expression or activity of LRP5, e.g, an LRP5 neutralizing antibody.

In another embodiment, the antibodies of the invention may be administered in combination with a DKK1 modulating agent, i.e., an agent that interfere or neutralize Dkk-1 mediated antagonism of Wnt signaling, e.g., a DKK1 neutralizing antibody.

In one embodiment, the antibodies of the invention may be administered in combination with a bisphosphonate e.g. alendronate, risedronate sodium, ibandronic acid, zoledronic acid, zoledronic acid, olpadronate, neridronate, skelid, bonefos.

In one embodiment, the antibodies of the invention may be administered in combination with (i) zoledronic acid, (ii) an anti-DKK1 antibody, (iii) alendronate, (iv) an anti-LRP4 antibody, (v) hPTH and/or (vi) parathyroid hormone releasing agents (calcilytics).

Other agents which can be administered in combination with the anti-sclerostin antibodies of the invention include vitamin D and/or calcium. In one embodiment the vitamin D and/or calcium is administered if the patient has a vitamin D and/or calcium deficiency.

In one embodiment, the antibodies of the invention are administered together with another agent (e.g. the above mentioned agents), in a sequential manner (i.e. one after the other) or simultaneously. In one embodiment, the anti-sclerostin antibody is administered according to the aforementioned doses and frequencies of administration. Suitable doses for the combination therapy agent can be varied according to the clinical requirements of the patient.

The compositions are preferably formulated at physiological pH.

Therapeutic compositions can be administered with medical devices known in the art. For example, in one embodiment, a therapeutic composition of the invention can be administered with a needleless hypodermic injection device, such as the devices shown in U.S. Pat. Nos. 5,399,163; 5,383,851; 5,312,335; 5,064,413; 4,941,880; 4,790,824 or 4,596,556. Examples of well-known implants and modules useful in the present invention include: U.S. Pat. No. 4,487,603, which shows an implantable micro-infusion pump for dispensing medication at a controlled rate; U.S. Pat. No. 4,486,194, which shows a therapeutic device for administering medicaments through the skin; U.S. Pat. No. 4,447,233, which shows a medication infusion pump for delivering medication at a precise infusion rate; U.S. Pat. No. 4,447,224, which shows a variable flow implantable infusion apparatus for continuous drug delivery; U.S. Pat. No. 4,439,196, which shows an osmotic drug delivery system having multi-chamber compartments; and U.S. Pat. No. 4,475,196, which shows an osmotic drug delivery system. These patents are incorporated herein by reference. Many other such implants, delivery systems, and modules are known to those skilled in the art. In one embodiment, the therapeutic composition of the invention can be administered with a syringe.

In certain embodiments, the antibodies of the invention can be formulated to ensure proper distribution in vivo.

In one aspect the invention provides use of an anti-sclerostin antibody for the manufacture of a medicament for the treatment of osteogenesis imperfecta. All of the other aspects/embodiments described herein apply equally to this particular aspect of the invention.

In another aspect the invention provides an anti-sclerostin antibody for use in the treatment of osteogenesis imperfecta. All of the other aspects/embodiments described herein apply equally to this particular aspect of the invention.

In one aspect, the invention provides an anti-sclerostin antibody for use in a clinical trial for osteogenesis imperfecta comprising comparing the number of fractures that have occurred in the clinical trial population at an interim time point during the clinical trial period with the number of fractures expected at said interim time point for said clinical trial population.

In a related aspect, the invention provides a method of conducting a clinical trial for osteogenesis imperfecta with an anti-sclerostin antibody comprising comparing the number of fractures that have occurred in a clinical trial population at an interim time point during the clinical trial period with the number of fractures expected at said interim time point for said clinical trial population. In one embodiment of the aforementioned aspects, the aspect may further comprise recruiting additional patients to the clinical trial population if the number of fractures in the clinical trial population at the interim time point is lower than the expected number of fractures for said clinical trial population. In one embodiment, the clinical trial period is extended if the number of fractures in the clinical trial population at the interim time point is lower than the expected number of fractures for said clinical trial population. In another embodiment, the clinical trial period is shortened if the number of fractures in the clinical trial population at the interim time point is higher than the expected number of fractures for said clinical trial population. The clinical trial population is made up of patients receiving the anti-sclerostin antibody and a control group of patients receiving a placebo. An advantage of these aspects/embodiments is that it allows the clinical trial period to be varied in response to developments in the clinic, which ultimately leads to a more efficient and cost-effective clinical trial which also benefits the patients. The expected number of fractures can be calculated from a baseline fracture rate which can be derived from historical data and/or from data from the clinical trial population prior to commencement of the clinical trial period. In one embodiment, the anti-sclerostin antibody is an anti-sclerostin antibody as defined herein. The interim time point can be varied and selected according to when a statistically significant comparison can be made. The clinical trial period begins with the administration of the anti-sclerostin antibody or placebo and ends once the final dose of anti-sclerostin antibody/placebo has been administered and the relevant data collected.

```
Sequence of BPS804 H-chain (SEQ ID NO: 172):
QVQLVESGGGLVQPGGSLRLSCAASGFTFRSHWLSWVRQAPGKGLEWVS

NINYDGSSTYYADSVKGRFTISRDNSKNTLYLQMNSLRAEDTAVYYCARD

TYLHFDYWGQGTLVTVSSASTKGPSVFPLAPCSRSTSESTAALGCLVKDY

FPEPVTVSWNSGALTSGVHTEPAVLQSSGLYSLSSVVTVPSSNFGTQTYT

CNVDHKPSNTKVDKTVERKCCVECPPCPAPPVAGPSVFLFPPKPKDTLM

ISRTPEVTCVVVDVSHEDPEVQFNWYVDGVEVHNAKTKPREEQFNSTFR

VVSVLTVVHQDWLNGKEYKCKVSNKGLPAPIEKTISKTKGQPREPQVYTL

PPSREEMTKNQVSLTCLVKGFYPSDIAVEWESNGQPENNYKTTPPMLDSD

GSFELYSKLTVDKSRWQQGNVFSCSVMHEALHNHYTQKSLSLSPGK

Sequence of BPS804 L-chain (SEQ ID NO: 173):
DIALTQPASVSGSPGQSITISCTGTSSDVGDINDVSWYQQHPGKAPKLMI

YDVNNRPSGVSNRFSGSKSGNTASLTISGLQAEDEADYYCQSYAGSYLSE

VFGGGTKLTVLGQPKAAPSVTLFPPSSEELQANKATLVCLISDFYPGAVT

VAWKADSSPVKAGVETTTPSKQSNNKYAASSYLSLTPEQWKSHRSYSCQV

THEGSTVEKTVAPTECS
```

MODES FOR CARRYING OUT THE INVENTION

Example 1

This example describes a clinical trial to assess the use of an anti-sclerostin antibody in the treatment of adult patients with OI. The patients were treated with three sequential intra-patient escalating doses of anti-sclerostin antibody BPS804, given as intravenous infusions separated by 2 weeks from each dose. An untreated reference group was enrolled as well for monitoring and observation of the natural OI disease progression with regard to changes in bone biomarker profiles. This trial was a randomized, open-label, intra-patient dose escalating study with an untreated reference group in 14 adult patients with moderate OI. Patients were randomized to the treatment group or the reference group at a ratio of 2:1.

Patients were administered every two weeks with escalating doses of the anti-sclerostin antibody: Week 1: 5 mg/kg, Week 3: 10 mg/kg and Week 5: 20 mg/kg. The treatment period was followed by an about 3.6 month follow-up period. Patients who were randomized to the untreated reference group at screening were only admitted to the study site at week 7, study Day 43 and at the end of the study.

A description of the study drug BPS804 is presented in Table 1. BPS804 solution for infusion was administered as an infusion at a flow rate of about 2 mL/min until the desired dose has been delivered.

Biomarkers of bone metabolism including procollagen I N-terminal propeptide (PINP), procollagen I C-terminal propeptide (PICP), bone-specific alkaline phosphatase (BSAP), osteocalcin (OC), and bone mineral density (BMD) (measured by DXA) were assayed at baseline, day 43 and day 141.

TABLE 1

| Study Drug BPS804 | |
| --- | --- |
| Name | BPS804 |
| Formulation | Powder for solution for infusion (lyophilizate in vial) |
| Appearance before reconstitution | White lyophilizate cake |
| Appearance after reconstitution | Opalescent to clear, colorless solution |
| Unit dose | 150 mg per vial * |
| Packaging | 6 mL Type I glass vials |
| Diluent for iv administration | Dextrose 5% in water (USP or equivalent) in 250 mL |

* The vials contain a 20% overfill to allow a complete withdrawal of the labeled amount of BPS804.

Of the 14 patients enrolled in the study, nine patients were exposed to anti-sclerostin antibody treatment. The overall mean age of the patients was marginally higher in the anti-sclerostin antibody group (30.7 years) when compared to the reference group (27.4 years). The overall mean weight and height between the two groups were very similar. Summary of patient demographics is presented in Table 2. The overall median scores of the lumbar spine z-score were comparatively lower in the anti-sclerostin antibody group. The overall years on bisphosphonates cannot be compared between the groups considering the relative size of the number of the patients in each group. See Table 3.

TABLE 2

Demographic Summary By Treatment Group

|  | BPS804 N = 9 | Reference N = 5 | Total N = 14 |
|---|---|---|---|
| Age (years) |  |  |  |
| Mean (SD) | 30.7 (13.47) | 27.4 (15.47) | 29.5 (13.71) |
| Median | 25.0 | 21.0 | 21.5 |
| Range | 19, 57 | 19, 55 | 19, 57 |
| Sex - n (%) |  |  |  |
| Male | 7 (77.8) | 3 (60.0) | 10 (71.4) |
| Female | 2 (22.2) | 2 (40.0) | 4 (28.6) |
| Predominant Race - n (%) |  |  |  |
| Caucasian | 9 (100) | 5 (100) | 14 (100) |
| Ethnicity - n (%) |  |  |  |
| Mixed ethnicity | 1 (11.1) | 1 (20.0) | 2 (14.3) |
| Other | 8 (88.9) | 4 (80.0) | 12 (85.7) |
| Weight (kg)* |  |  |  |
| Mean (SD) | 61.84 (14.378) | 58.20 (13.034) | 60.54 (13.519) |
| Median | 63.90 | 54.00 | 59.45 |
| Range | 43.5, 80.1 | 44.0, 75.0 | 43.5, 80.1 |
| Height (cm)* |  |  |  |
| Mean (SD) | 161.6 (12.19) | 162.8 (13.85) | 162.0 (12.28) |
| Median | 162.0 | 161.0 | 162.0 |
| Range | 142, 178 | 142, 176 | 142, 178 |

*Weight and height are taken from Screening vital signs evaluations.

TABLE 3

Disease Characteristics By Treatment Group At Study Entry

|  | BPS804 N = 9 | Reference N = 5 | Total N = 14 |
|---|---|---|---|
| Lumbar spine z-score* |  |  |  |
| Mean (SD) | −2.59 (1.191) | −2.18 (0.514) | −2.44 (0.997) |
| Median | −2.30 | −2.07 | −2.19 |
| Range | −4.9, −1.1 | −2.9, −1.5 | −4.9, −1.1 |
| Yrs. on bisphosphonates# |  |  |  |
| N | 2 | 1 | 3 |
| Mean (SD) | 8.53 (4.882) | 15.46 (—) | 10.84 (5.283) |
| Median | 8.53 | 15.46 | 11.99 |
| Range | 5.1, 12.0 | 15.5, 15.5 | 5.1, 15.5 |
| Subjects with D43 Biomarker data - n (%) | 9 (100) | 5 (100) | 14 (100) |
| Subjects with D141 BMD data - n (%) | 9 (100) | 4 (80.0) | 13 (92.9) |

*Lumbar spine z-score is taken at screening.
Years on bisphosphonates is calculated from the medical history page, by taking the difference between the earliest start date of bisphosphonates medication and date of screening.

The assay results of the bone metabolism biomarkers for the study are presented in FIG. 1. The ratios of geometric means for PINP, PICP, BSAP, and OC at Day 43 were 1.84, 1.53, 1.59 and 1.44 with P-values of <0.001, 0.003, <0.001, and 0.012 in the BPS804 group. The ratio of geometric means for BMD at Day 141 was 1.04 with P-value of 0.038.

The Bayesian analysis of change from baseline for PINP, PICP, and BSAP showed a posterior probability of around 90% or higher for an increase of at least 70% (PINP) or 30% (PICP, BSAP). The Bayesian analysis for BMD showed a posterior probably of 98% for an increase in BMD, and 87% for an increase of at least 2%. See FIG. 3, FIG. 4, FIG. 5, FIG. 6 and FIG. 7 for details on the PINP, PICP, B SAP, OC and BMD results, respectively.

Figure 8:
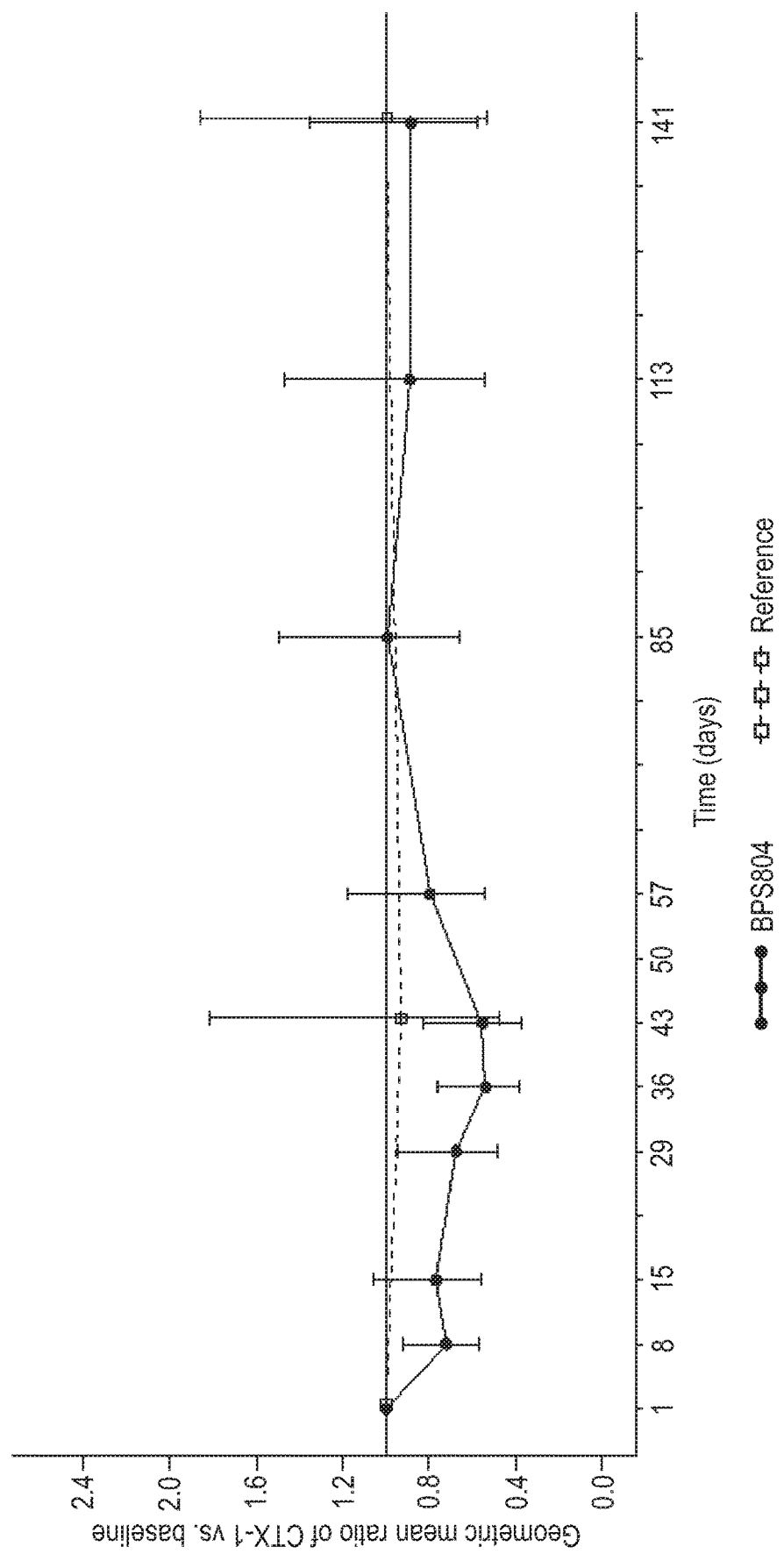
FIG. 8 shows a graph depicting ratios of baseline in geometric means (plus or minus SD) for CTX-1.

The geometric mean results on CTX-1 from Day 8 through Day 43 showed a decrease in CTX-1 concentration levels which together with bone formation biomarker results supports bone anabolic effects. FIG. 8 presents the details of the values since Baseline. On Day 43, the ratio from baseline in the BPS804 group was 56% of baseline, thus a reduction by 44%. The concentration levels steadily increased from Day 50 through Day 85 with a marginal decrease on Days 113 and 141.

The comparison of ratios with the matching ratios in the reference group were performed as per the planned two sample t-tests (1-sided) and a P-value of below 0.1 in this comparison was considered supportive evidence for efficacy. Based on the two sample t-tests analysis, the P-values were <0.001, 0.014, 0.006, and 0.015 for PINP, PICP, BSAP, and OC, respectively, which supported the evidence for efficacy. The p-value for treatment group comparison of BMD was 0.1, also supporting the evidence that increase was larger under the anti-sclerostin antibody than in the reference group. See FIG. 2. These analyses confirmed the evidence of higher increase in the anti-sclerostin antibody group than in the reference group, for all three biomarker data and for the BMD data.

After administration of the anti-sclerostin antibody, median PINP, PICP, BSAP activity, and OC levels were increased at Day 43 by 84%, 53%, 59%, and 44%, respectively, while corresponding biomarkers remained unchanged or declined moderately in the untreated reference group. Further, after administration of the anti-sclerostin antibody, CTX-1 level was decreased by 44% at Day 43 from baseline. The increase of bone formation biomarker (PINP, PICP, BSAP and OC) levels and the reduction of bone resorption biomarker (CTX-1) level were in line with the observed increase by ~4% in lumbar spine BMD at Day 141 in the anti-sclerostin antibody treatment group, thus confirming the first clinical evidence of bone anabolic effects of an anti-sclerostin antibody in patients with osteogenesis imperfecta.

In addition, the study showed that the anti-sclerostin antibody was safe and well-tolerated in the adult patients with OI. The most commonly reported AEs were headache, influenza, arthralgia, and fatigue. None of the reported AEs were considered related to the study drug. There was one SAE (Goiter) of mild intensity reported in one patient in the reference group. This AE was considered serious because of hospitalization. The SAE resolved prior to end-of-study. The AEs gave no indication of target organ toxicity. Three fractures were reported during the study (subject 5103—Day 47, subject 5109—Day 4, Subject 5113—Day 4). There were also no clinically significant abnormalities of hematological, clinical chemistry, urinalysis, ECG or vital sign data compromising the patients' safety.

According to the clinical study results, with an osteoanabolic treatment like BPS804, bone formation or bone anabolic activity can be stimulated in patients with OI. The increase in BMD results in improved bone quality thereby leading to a reduction in the fracture rate and risk. Geno-

Example 2

A pharmacokinetic (PK) model was developed for BPS804 along with a pharmacokinetic (PK) and pharmacodynamics (PD) (PK-PD) model for circulating sclerostin effects after BPS804 administration based on a combination of clinical trial data and publically available data on other anti-sclerostin antibodies. The PK-PD model was linked to an existing systems pharmacology model to evaluate proposed dosing regimens for BPS804. Model simulations were used to provide guidance for dose selection and dosing interval over 1-2 years of treatment for typical OI patients. These included scenarios with different dosing considerations for the first year (e.g., comparison of dosage amount and QM (i.e. monthly) vs. Q3M (i.e. quarterly) dosing) as well as considerations for subsequent years (e.g., switching from QM to Q3M dosing).

Results:

The data demonstrated that BPS804 dosing regimens nearing maximal (>75%) inhibition of sclerostin provide near maximal responses in circulating sclerostin, bone turnover markers (BTM), and lumbar spine bone mineral density (BMD). To demonstrate this, a range of doses from 0.1 mg/kg to 20 mg/kg were simulated using QM (i.e. monthly) and Q3M (i.e. quarterly) intervals for a two-year timecourse. Results were evaluated assuming full BPS804 exposure effects on sclerostin and relative to maximal inhibition. Overall, the 20 mg/kg QM dose approached the maximal sclerostin response. The maximum level of inhibition was reached by both monthly and quarterly dosing regimens, alike, and both the QM and Q3M 20 mg/kg dosing regimens reached the maximum inhibition level.

The modeling results further indicated that a BPS804 20 mg/kg QM dose would provide similar or a slightly greater 12-month BMD increase compared with Q3M dosing due to the longer sustained inhibition of sclerostin with BPS804.

Following one-year of treatment with BPS804 20 mg/kg QM, nearly the same peak maximum sclerostin response can also achieved with a 20 mg/kg dose administered quarterly. This potential change in dosing regimen after one-year of dosing could reflect the attainment of an apparent new steady-state in the bone remodeling system after one year of sclerostin inhibition therapy. Therefore, less frequent dosing after the first year of dosing may allow for maintenance of BMD increases from the first year of dosing.

In summary, the modelling data show that BPS804 20 mg/kg QM dosing is expected to provide near maximal inhibition of sclerostin that would translate into maximal BMD response. In addition, extending dosing intervals for longer-term dosing (e.g., switching to dosing every two months (Q2M) or Q3M following one-year of QM dosing) may be advantageous given the observed changes in bone turnover markers following the first year of treatment.

The patents and publications listed herein describe the general skill in the art. In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

---

The invention claimed is:

1. A method for treating osteogenesis imperfecta (OI) in a human patient comprising administering to the human patient in need thereof a therapeutically effective amount of an anti-sclerostin antibody, wherein the OI is type I OI, type III OI or type IV OI, wherein the human patient has one or more mutations in the COL1A1 and/or COL1A2 genes, and wherein the anti-sclerostin antibody comprises:
   (a) a heavy chain variable region CDR1 comprising the amino acid sequence set forth in SEQ ID NO:4;
   (b) a heavy chain variable region CDR2 comprising the amino acid sequence set forth in SEQ ID NO:15;
   (c) a heavy chain variable region CDR3 comprising the amino acid sequence set forth in SEQ ID NO:26;
   (d) a light chain variable region CDR1 comprising the amino acid sequence set forth in SEQ ID NO:37;
   (e) a light chain variable region CDR2 comprising the amino acid sequence set forth in SEQ ID NO:48; and
   (f) a light chain variable region CDR3 comprising the amino acid sequence set forth in SEQ ID NO:59;
   and wherein the anti-sclerostin antibody is administered by injection at a dose of 8-25 mg per kg body weight of the human patient, and wherein the antibody is administered monthly, bi-monthly, or quarterly.

2. The method according to claim 1, wherein the anti-sclerostin antibody comprises:
   a) a VH polypeptide sequence having at least 90 percent sequence identity to the amino acid sequences set forth as SEQ ID NO:70; and/or
   b) a VL polypeptide sequence having at least 90 percent sequence identity to the amino acid sequences set forth as SEQ ID NO:81.

3. The method according to claim 1, wherein the anti-sclerostin antibody comprises a VL polypeptide sequence comprising the amino acid sequence set forth as SEQ ID NO:81 and a VH polypeptide sequence comprising the amino acid sequence set forth as SEQ ID NO:70.

4. The method according to claim 1, wherein the anti-sclerostin antibody comprises:
   a) a full length heavy chain amino acid sequence having at least 90 percent sequence identity to the amino acid sequence set forth as SEQ ID NO:172; and/or
   b) a full length light chain amino acid sequence having at least 90 percent sequence identity to the amino acid sequence set forth as SEQ ID NO:173.

5. The method of claim 3, wherein the anti-sclerostin antibody comprises the full length light chain amino acid sequence comprising the amino acid sequence set forth as SEQ ID NO: 173 and the full length heavy chain amino acid sequence comprising the amino acid sequence set forth as SEQ ID NO: 172.

6. The method of claim 1, wherein the anti-sclerostin antibody is administered at a dose of 10-20 mg per kg body weight of the human patient.

7. The method of claim 6, wherein the anti-sclerostin antibody is administered at a dose of 20 mg per kg body weight of the human patient.

8. The method of claim 1, wherein the anti-sclerostin antibody is administered to the human patient on a monthly basis.

9. The method of claim 1, wherein the anti-sclerostin antibody is administered to the human patient on a quarterly basis.

10. The method of claim 6, wherein the anti-sclerostin antibody is administered to the patient on a monthly basis for a period of 1 year, followed by administration on a bi-monthly or quarterly basis.

11. The method of claim 5 wherein the anti-sclerostin antibody is administered intravenously at a dose of 10 20 mg per kg body weight of the human patient on a monthly basis.

12. The method of claim 5, wherein the dose is 10 20 mg per kg body weight of the human patient on a quarterly basis.

13. The method of claim 11, wherein the dose is 20 mg per kg body weight of the human patient.

14. The method of claim 8, wherein the dose is 20 mg per kg body weight of a patient.

15. The method of claim 1, comprising administering a further therapeutic agent, selected from the group consisting of bisphosphonate, parathyroid hormone, calcilytics, calcimimetics such as cinacalcet, statins, anabolic steroids, lanthanum and strontium salts, sodium fluoride, and combinations thereof.

16. A method for treating osteogenesis imperfecta (OI) in a human patient comprising administering to the human patient in need thereof a therapeutically effective amount of an anti-sclerostin antibody, wherein the OI is type I OI, type III OI or type IV OI, wherein the human patient has one or more mutations in the COL1A1 and/or COL1A2 genes, and wherein the anti-sclerostin antibody comprises:

(a) a heavy chain variable region CDR1 comprising the amino acid sequence set forth in SEQ ID NO:4;
(b) a heavy chain variable region CDR2 comprising the amino acid sequence set forth in SEQ ID NO:15;
(c) a heavy chain variable region CDR3 comprising the amino acid sequence set forth in SEQ ID NO:26;
(d) a light chain variable region CDR1 comprising the amino acid sequence set forth in SEQ ID NO:37;
(e) a light chain variable region CDR2 comprising the amino acid sequence set forth in SEQ ID NO:48; and
(f) a light chain variable region CDR3 comprising the amino acid sequence set forth in SEQ ID NO:59;

and wherein the anti-sclerostin antibody is administered by injection at a dose of 10-30 mg per kg body weight of the human patient, and wherein the antibody is administered monthly, bi-monthly, or quarterly.

17. The method of claim 16 wherein the anti-sclerostin antibody is administered to the human patient on a monthly basis.

18. The method of claim 17 wherein the anti-sclerostin antibody is administered intravenously.

19. The method of claim 1 wherein the anti-sclerostin antibody is administered intravenously.

* * * * *

UNITED STATES PATENT AND TRADEMARK OFFICE
CERTIFICATE OF CORRECTION

PATENT NO. : 10,961,305 B2  
APPLICATION NO. : 16/469920  
DATED : March 30, 2021  
INVENTOR(S) : Uwe Junker et al.

Page 1 of 1

It is certified that error appears in the above-identified patent and that said Letters Patent is hereby corrected as shown below:

In the Claims

In Claim 11, Column 153, Line 6, change "10 20 ;" should be --10-20--;

In Claim 12, Column 153, Line 8, change "10 20 ;" should be --10-20--.

Signed and Sealed this  
Eleventh Day of May, 2021

Drew Hirshfeld  
*Performing the Functions and Duties of the*  
*Under Secretary of Commerce for Intellectual Property and*  
*Director of the United States Patent and Trademark Office*

SEQUENCE LISTING

```
<160> NUMBER OF SEQ ID NOS: 177

<210> SEQ ID NO 1
<211> LENGTH: 10
<212> TYPE: PRT
<213> ORGANISM: Homo sapiens

<400> SEQUENCE: 1

Gly Phe Thr Phe Ser Ser Tyr Val Met Asn
1               5                   10

<210> SEQ ID NO 2
<211> LENGTH: 10
<212> TYPE: PRT
<213> ORGANISM: Homo sapiens

<400> SEQUENCE: 2

Gly Phe Thr Phe Arg Ser His Trp Leu Ser
1               5                   10

<210> SEQ ID NO 3
<211> LENGTH: 10
<212> TYPE: PRT
<213> ORGANISM: Homo sapiens

<400> SEQUENCE: 3
```

```
Gly Phe Thr Phe Ser Ser Tyr Val Met Asn
1               5                   10

<210> SEQ ID NO 4
<211> LENGTH: 10
<212> TYPE: PRT
<213> ORGANISM: Homo sapiens

<400> SEQUENCE: 4

Gly Phe Thr Phe Arg Ser His Trp Leu Ser
1               5                   10

<210> SEQ ID NO 5
<211> LENGTH: 10
<212> TYPE: PRT
<213> ORGANISM: Homo sapiens

<400> SEQUENCE: 5

Gly Phe Thr Phe Arg Ser His Trp Leu Ser
1               5                   10

<210> SEQ ID NO 6
<211> LENGTH: 10
<212> TYPE: PRT
<213> ORGANISM: Homo sapiens

<400> SEQUENCE: 6

Gly Phe Thr Phe Arg Ser His Trp Leu Ser
1               5                   10

<210> SEQ ID NO 7
<211> LENGTH: 10
<212> TYPE: PRT
<213> ORGANISM: Homo sapiens

<400> SEQUENCE: 7

Gly Phe Thr Phe Arg Ser His Trp Leu Ser
1               5                   10

<210> SEQ ID NO 8
<211> LENGTH: 10
<212> TYPE: PRT
<213> ORGANISM: Homo sapiens

<400> SEQUENCE: 8

Gly Phe Thr Phe Arg Ser His Trp Leu Ser
1               5                   10

<210> SEQ ID NO 9
<211> LENGTH: 10
<212> TYPE: PRT
<213> ORGANISM: Homo sapiens

<400> SEQUENCE: 9

Gly Phe Thr Phe Arg Ser His Trp Leu Ser
1               5                   10

<210> SEQ ID NO 10
<211> LENGTH: 10
<212> TYPE: PRT
<213> ORGANISM: Homo sapiens

<400> SEQUENCE: 10

Gly Phe Thr Phe Arg Ser His Trp Leu Ser
1               5                   10
```

<210> SEQ ID NO 11
<211> LENGTH: 10
<212> TYPE: PRT
<213> ORGANISM: Homo sapiens

<400> SEQUENCE: 11

Gly Phe Thr Phe Arg Ser His Trp Leu Ser
1               5                   10

<210> SEQ ID NO 12
<211> LENGTH: 20
<212> TYPE: PRT
<213> ORGANISM: Homo sapiens

<400> SEQUENCE: 12

Trp Val Ser Phe Ile Ser Gly Asp Ser Ser Asn Thr Tyr Tyr Ala Asp
1               5                   10                  15

Ser Val Lys Gly
            20

<210> SEQ ID NO 13
<211> LENGTH: 20
<212> TYPE: PRT
<213> ORGANISM: Homo sapiens

<400> SEQUENCE: 13

Trp Val Ser Asn Ile Asn Tyr Asp Gly Ser Ser Thr Tyr Tyr Ala Asp
1               5                   10                  15

Ser Val Lys Gly
            20

<210> SEQ ID NO 14
<211> LENGTH: 20
<212> TYPE: PRT
<213> ORGANISM: Homo sapiens

<400> SEQUENCE: 14

Trp Val Ser Phe Ile Ser Gly Asp Ser Ser Asn Thr Tyr Tyr Ala Asp
1               5                   10                  15

Ser Val Lys Gly
            20

<210> SEQ ID NO 15
<211> LENGTH: 20
<212> TYPE: PRT
<213> ORGANISM: Homo sapiens

<400> SEQUENCE: 15

Trp Val Ser Asn Ile Asn Tyr Asp Gly Ser Ser Thr Tyr Tyr Ala Asp
1               5                   10                  15

Ser Val Lys Gly
            20

<210> SEQ ID NO 16
<211> LENGTH: 19
<212> TYPE: PRT
<213> ORGANISM: Homo sapiens

<400> SEQUENCE: 16

Trp Val Ser Val Thr Gly Val His Gly Asp Thr Tyr Tyr Ala Asp Ser
1               5                   10                  15

Val Lys Gly

<210> SEQ ID NO 17
<211> LENGTH: 19
<212> TYPE: PRT
<213> ORGANISM: Homo sapiens

<400> SEQUENCE: 17

Trp Val Ser Val Ile Gly Asn Trp Gly Asp Thr Tyr Tyr Ala Asp Ser
1               5                   10                  15

Val Lys Gly

<210> SEQ ID NO 18
<211> LENGTH: 19
<212> TYPE: PRT
<213> ORGANISM: Homo sapiens

<400> SEQUENCE: 18

Trp Val Ser Val Thr Thr His Gln Gly Tyr Thr Tyr Tyr Ala Asp Ser
1               5                   10                  15

Val Lys Gly

<210> SEQ ID NO 19
<211> LENGTH: 19
<212> TYPE: PRT
<213> ORGANISM: Homo sapiens

<400> SEQUENCE: 19

Trp Val Ser Ala Thr Asn Arg Tyr Gly Tyr Thr Tyr Tyr Ala Asp Ser
1               5                   10                  15

Val Lys Gly

<210> SEQ ID NO 20
<211> LENGTH: 20
<212> TYPE: PRT
<213> ORGANISM: Homo sapiens

<400> SEQUENCE: 20

Trp Val Ser Asn Ile Asn Tyr Asp Gly Ser Ser Thr Tyr Tyr Ala Asp
1               5                   10                  15

Ser Val Lys Gly
            20

<210> SEQ ID NO 21
<211> LENGTH: 19
<212> TYPE: PRT
<213> ORGANISM: Homo sapiens

<400> SEQUENCE: 21

Trp Val Ser Val Ile Thr Pro Tyr Gly Asp Thr Tyr Tyr Ala Asp Ser
1               5                   10                  15

Val Lys Gly

<210> SEQ ID NO 22
<211> LENGTH: 19
<212> TYPE: PRT
<213> ORGANISM: Homo sapiens

<400> SEQUENCE: 22

Trp Val Ser Val Ile Thr Pro Tyr Gly Asp Thr Tyr Tyr Ala Asp Ser
1               5                   10                  15

Val Lys Gly

<210> SEQ ID NO 23
<211> LENGTH: 15
<212> TYPE: PRT
<213> ORGANISM: Homo sapiens

<400> SEQUENCE: 23

Thr Phe Met His Gly His Leu Gly Gly Gly Leu Ser Met Asp Phe
1               5                   10                  15

<210> SEQ ID NO 24
<211> LENGTH: 8
<212> TYPE: PRT
<213> ORGANISM: Homo sapiens

<400> SEQUENCE: 24

Asp Thr Tyr Leu His Phe Asp Tyr
1               5

<210> SEQ ID NO 25
<211> LENGTH: 15
<212> TYPE: PRT
<213> ORGANISM: Homo sapiens

<400> SEQUENCE: 25

Thr Phe Met His Gly His Leu Gly Gly Gly Leu Ser Met Asp Phe
1               5                   10                  15

<210> SEQ ID NO 26
<211> LENGTH: 8
<212> TYPE: PRT
<213> ORGANISM: Homo sapiens

<400> SEQUENCE: 26

Asp Thr Tyr Leu His Phe Asp Tyr
1               5

<210> SEQ ID NO 27
<211> LENGTH: 8
<212> TYPE: PRT
<213> ORGANISM: Homo sapiens

<400> SEQUENCE: 27

Asp Thr Tyr Leu His Phe Asp Tyr
1               5

<210> SEQ ID NO 28
<211> LENGTH: 8
<212> TYPE: PRT
<213> ORGANISM: Homo sapiens

<400> SEQUENCE: 28

Asp Thr Tyr Leu His Phe Asp Tyr
1               5

<210> SEQ ID NO 29
<211> LENGTH: 8
<212> TYPE: PRT
<213> ORGANISM: Homo sapiens

<400> SEQUENCE: 29

Asp Thr Tyr Leu His Phe Asp Tyr
1               5

```
<210> SEQ ID NO 30
<211> LENGTH: 8
<212> TYPE: PRT
<213> ORGANISM: Homo sapiens

<400> SEQUENCE: 30

Asp Thr Tyr Leu His Phe Asp Tyr
1               5

<210> SEQ ID NO 31
<211> LENGTH: 8
<212> TYPE: PRT
<213> ORGANISM: Homo sapiens

<400> SEQUENCE: 31

Asp Thr Tyr Leu His Phe Asp Tyr
1               5

<210> SEQ ID NO 32
<211> LENGTH: 8
<212> TYPE: PRT
<213> ORGANISM: Homo sapiens

<400> SEQUENCE: 32

Asp Thr Tyr Leu His Phe Asp Tyr
1               5

<210> SEQ ID NO 33
<211> LENGTH: 8
<212> TYPE: PRT
<213> ORGANISM: Homo sapiens

<400> SEQUENCE: 33

Asp Thr Tyr Leu His Phe Asp Tyr
1               5

<210> SEQ ID NO 34
<211> LENGTH: 11
<212> TYPE: PRT
<213> ORGANISM: Homo sapiens

<400> SEQUENCE: 34

Ser Gly Asp Asn Ile Gly Ser Phe Tyr Val His
1               5                   10

<210> SEQ ID NO 35
<211> LENGTH: 20
<212> TYPE: PRT
<213> ORGANISM: Homo sapiens

<400> SEQUENCE: 35

Trp Val Ser Asn Ile Asn Tyr Asp Gly Ser Ser Thr Tyr Tyr Ala Asp
1               5                   10                  15

Ser Val Lys Gly
            20

<210> SEQ ID NO 36
<211> LENGTH: 11
<212> TYPE: PRT
<213> ORGANISM: Homo sapiens

<400> SEQUENCE: 36

Ser Gly Asp Asn Ile Gly Ser Phe Tyr Val His
1               5                   10
```

```
<210> SEQ ID NO 37
<211> LENGTH: 14
<212> TYPE: PRT
<213> ORGANISM: Homo sapiens

<400> SEQUENCE: 37

Thr Gly Thr Ser Ser Asp Val Gly Asp Ile Asn Asp Val Ser
1               5                   10

<210> SEQ ID NO 38
<211> LENGTH: 14
<212> TYPE: PRT
<213> ORGANISM: Homo sapiens

<400> SEQUENCE: 38

Thr Gly Thr Ser Ser Asp Val Gly Asp Ile Asn Asp Val Ser
1               5                   10

<210> SEQ ID NO 39
<211> LENGTH: 14
<212> TYPE: PRT
<213> ORGANISM: Homo sapiens

<400> SEQUENCE: 39

Thr Gly Thr Ser Ser Asp Val Gly Asp Ile Asn Asp Val Ser
1               5                   10

<210> SEQ ID NO 40
<211> LENGTH: 14
<212> TYPE: PRT
<213> ORGANISM: Homo sapiens

<400> SEQUENCE: 40

Thr Gly Thr Ser Ser Asp Val Gly Asp Ile Asn Asp Val Ser
1               5                   10

<210> SEQ ID NO 41
<211> LENGTH: 14
<212> TYPE: PRT
<213> ORGANISM: Homo sapiens

<400> SEQUENCE: 41

Thr Gly Thr Ser Ser Asp Val Gly Asp Ile Asn Asp Val Ser
1               5                   10

<210> SEQ ID NO 42
<211> LENGTH: 14
<212> TYPE: PRT
<213> ORGANISM: Homo sapiens

<400> SEQUENCE: 42

Thr Gly Thr Ser Ser Asp Val Gly Asp Ile Asn Asp Val Ser
1               5                   10

<210> SEQ ID NO 43
<211> LENGTH: 14
<212> TYPE: PRT
<213> ORGANISM: Homo sapiens

<400> SEQUENCE: 43

Thr Gly Thr Ser Ser Asp Val Gly Asp Ile Asn Asp Val Ser
1               5                   10
```

```
<210> SEQ ID NO 44
<211> LENGTH: 14
<212> TYPE: PRT
<213> ORGANISM: Homo sapiens

<400> SEQUENCE: 44

Thr Gly Thr Ser Ser Asp Val Gly Asp Ile Asn Asp Val Ser
1               5                   10

<210> SEQ ID NO 45
<211> LENGTH: 11
<212> TYPE: PRT
<213> ORGANISM: Homo sapiens

<400> SEQUENCE: 45

Leu Val Ile Tyr Asp Asp Asn Asn Arg Pro Ser
1               5                   10

<210> SEQ ID NO 46
<211> LENGTH: 11
<212> TYPE: PRT
<213> ORGANISM: Homo sapiens

<400> SEQUENCE: 46

Leu Met Ile Tyr Asp Val Asn Asn Arg Pro Ser
1               5                   10

<210> SEQ ID NO 47
<211> LENGTH: 11
<212> TYPE: PRT
<213> ORGANISM: Homo sapiens

<400> SEQUENCE: 47

Leu Val Ile Tyr Asp Asp Asn Asn Arg Pro Ser
1               5                   10

<210> SEQ ID NO 48
<211> LENGTH: 11
<212> TYPE: PRT
<213> ORGANISM: Homo sapiens

<400> SEQUENCE: 48

Leu Met Ile Tyr Asp Val Asn Asn Arg Pro Ser
1               5                   10

<210> SEQ ID NO 49
<211> LENGTH: 11
<212> TYPE: PRT
<213> ORGANISM: Homo sapiens

<400> SEQUENCE: 49

Leu Met Ile Tyr Asp Val Asn Asn Arg Pro Ser
1               5                   10

<210> SEQ ID NO 50
<211> LENGTH: 11
<212> TYPE: PRT
<213> ORGANISM: Homo sapiens

<400> SEQUENCE: 50

Leu Met Ile Tyr Asp Val Asn Asn Arg Pro Ser
1               5                   10

<210> SEQ ID NO 51
<211> LENGTH: 11
```

```
<212> TYPE: PRT
<213> ORGANISM: Homo sapiens

<400> SEQUENCE: 51

Leu Met Ile Tyr Asp Val Asn Asn Arg Pro Ser
1               5                   10

<210> SEQ ID NO 52
<211> LENGTH: 11
<212> TYPE: PRT
<213> ORGANISM: Homo sapiens

<400> SEQUENCE: 52

Leu Met Ile Tyr Asp Val Asn Asn Arg Pro Ser
1               5                   10

<210> SEQ ID NO 53
<211> LENGTH: 11
<212> TYPE: PRT
<213> ORGANISM: Homo sapiens

<400> SEQUENCE: 53

Leu Met Ile Tyr Asp Val Asn Asn Arg Pro Ser
1               5                   10

<210> SEQ ID NO 54
<211> LENGTH: 11
<212> TYPE: PRT
<213> ORGANISM: Homo sapiens

<400> SEQUENCE: 54

Leu Met Ile Tyr Asp Val Asn Asn Arg Pro Ser
1               5                   10

<210> SEQ ID NO 55
<211> LENGTH: 11
<212> TYPE: PRT
<213> ORGANISM: Homo sapiens

<400> SEQUENCE: 55

Leu Met Ile Tyr Asp Val Asn Asn Arg Pro Ser
1               5                   10

<210> SEQ ID NO 56
<211> LENGTH: 10
<212> TYPE: PRT
<213> ORGANISM: Homo sapiens

<400> SEQUENCE: 56

Gly Ser Trp Ala Gly Ser Ser Gly Ser Tyr
1               5                   10

<210> SEQ ID NO 57
<211> LENGTH: 10
<212> TYPE: PRT
<213> ORGANISM: Homo sapiens

<400> SEQUENCE: 57

Ser Ser Tyr Gly Glu Ser Leu Thr Ser Tyr
1               5                   10

<210> SEQ ID NO 58
<211> LENGTH: 10
<212> TYPE: PRT
<213> ORGANISM: Homo sapiens
```

<400> SEQUENCE: 58

Ala Ser Trp Thr Gly Val Glu Pro Asp Tyr
1               5                   10

<210> SEQ ID NO 59
<211> LENGTH: 10
<212> TYPE: PRT
<213> ORGANISM: Homo sapiens

<400> SEQUENCE: 59

Gln Ser Tyr Ala Gly Ser Tyr Leu Ser Glu
1               5                   10

<210> SEQ ID NO 60
<211> LENGTH: 10
<212> TYPE: PRT
<213> ORGANISM: Homo sapiens

<400> SEQUENCE: 60

Ser Ser Tyr Gly Glu Ser Leu Thr Ser Tyr
1               5                   10

<210> SEQ ID NO 61
<211> LENGTH: 10
<212> TYPE: PRT
<213> ORGANISM: Homo sapiens

<400> SEQUENCE: 61

Ser Ser Tyr Gly Glu Ser Leu Thr Ser Tyr
1               5                   10

<210> SEQ ID NO 62
<211> LENGTH: 10
<212> TYPE: PRT
<213> ORGANISM: Homo sapiens

<400> SEQUENCE: 62

Ser Ser Tyr Gly Glu Ser Leu Thr Ser Tyr
1               5                   10

<210> SEQ ID NO 63
<211> LENGTH: 10
<212> TYPE: PRT
<213> ORGANISM: Homo sapiens

<400> SEQUENCE: 63

Ser Ser Tyr Gly Glu Ser Leu Thr Ser Tyr
1               5                   10

<210> SEQ ID NO 64
<211> LENGTH: 10
<212> TYPE: PRT
<213> ORGANISM: Homo sapiens

<400> SEQUENCE: 64

Ser Thr Tyr Asp Gly Pro Gly Leu Ser Glu
1               5                   10

<210> SEQ ID NO 65
<211> LENGTH: 10
<212> TYPE: PRT
<213> ORGANISM: Homo sapiens

<400> SEQUENCE: 65

```
Ser Ser Tyr Gly Glu Ser Leu Thr Ser Tyr
1               5                   10

<210> SEQ ID NO 66
<211> LENGTH: 10
<212> TYPE: PRT
<213> ORGANISM: Homo sapiens

<400> SEQUENCE: 66

Ser Ser Tyr Gly Glu Ser Leu Thr Ser Tyr
1               5                   10

<210> SEQ ID NO 67
<211> LENGTH: 124
<212> TYPE: PRT
<213> ORGANISM: Homo sapiens

<400> SEQUENCE: 67

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Asn Trp Val Arg Gln Ala Pro Gly Lys Gly Leu Glu Trp Val
        35                  40                  45

Ser Phe Ile Ser Gly Asp Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Phe Met His Gly His Leu Gly Gly Gly Leu Ser Met Asp
            100                 105                 110

Phe Trp Gly Gln Gly Thr Leu Val Thr Val Ser Ser
        115                 120

<210> SEQ ID NO 68
<211> LENGTH: 117
<212> TYPE: PRT
<213> ORGANISM: Homo sapiens

<400> SEQUENCE: 68

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser His
            20                  25                  30

Trp Leu Ser Trp Val Arg Gln Ala Pro Gly Lys Gly Leu Glu Trp Val
        35                  40                  45

Ser Asn Ile Asn Tyr Asp Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Tyr Leu His Phe Asp Tyr Trp Gly Gln Gly Thr Leu
            100                 105                 110

Val Thr Val Ser Ser
        115
```

<210> SEQ ID NO 69
<211> LENGTH: 124
<212> TYPE: PRT
<213> ORGANISM: Homo sapiens

<400> SEQUENCE: 69

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Asn Trp Val Arg Gln Ala Pro Gly Lys Gly Leu Glu Trp Val
        35                  40                  45

Ser Phe Ile Ser Gly Asp Ser Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Thr Phe Met His Gly His Leu Gly Gly Leu Ser Met Asp
            100                 105                 110

Phe Trp Gly Gln Gly Thr Leu Val Thr Val Ser Ser
        115                 120

<210> SEQ ID NO 70
<211> LENGTH: 117
<212> TYPE: PRT
<213> ORGANISM: Homo sapiens

<400> SEQUENCE: 70

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser His
            20                  25                  30

Trp Leu Ser Trp Val Arg Gln Ala Pro Gly Lys Gly Leu Glu Trp Val
        35                  40                  45

Ser Asn Ile Asn Tyr Asp Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Tyr Leu His Phe Asp Tyr Trp Gly Gln Gly Thr Leu
            100                 105                 110

Val Thr Val Ser Ser
        115

<210> SEQ ID NO 71
<211> LENGTH: 116
<212> TYPE: PRT
<213> ORGANISM: Homo sapiens

<400> SEQUENCE: 71

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser His
            20                  25                  30

Trp Leu Ser Trp Val Arg Gln Ala Pro Gly Lys Gly Leu Glu Trp Val

```
                35                  40                  45
Ser Val Thr Gly Val His Gly Asp Thr Tyr Tyr Ala Asp Ser Val Lys
 50                  55                  60
Gly Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Ala
                 85                  90                  95
Arg Asp Thr Tyr Leu His Phe Asp Tyr Trp Gly Gln Gly Thr Leu Val
                100                 105                 110
Thr Val Ser Ser
        115
```

<210> SEQ ID NO 72
<211> LENGTH: 116
<212> TYPE: PRT
<213> ORGANISM: Homo sapiens

<400> SEQUENCE: 72

```
Gln Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Arg Ser His
                20                  25                  30
Trp Leu Ser Trp Val Arg Gln Ala Pro Gly Lys Gly Leu Glu Trp Val
                35                  40                  45
Ser Val Ile Gly Asn Trp Gly Asp Thr Tyr Tyr Ala Asp Ser Val Lys
 50                  55                  60
Gly Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Ala
                 85                  90                  95
Arg Asp Thr Tyr Leu His Phe Asp Tyr Trp Gly Gln Gly Thr Leu Val
                100                 105                 110
Thr Val Ser Ser
        115
```

<210> SEQ ID NO 73
<211> LENGTH: 116
<212> TYPE: PRT
<213> ORGANISM: Homo sapiens

<400> SEQUENCE: 73

```
Gln Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Arg Ser His
                20                  25                  30
Trp Leu Ser Trp Val Arg Gln Ala Pro Gly Lys Gly Leu Glu Trp Val
                35                  40                  45
Ser Val Thr His Gln Gly Tyr Thr Tyr Tyr Ala Asp Ser Val Lys
 50                  55                  60
Gly Arg Phe Thr Ile Ser Arg Asp Asn Ser Lys Asn Thr Leu Tyr Leu
 65                  70                  75                  80
Gln Met Asn Ser Leu Arg Ala Glu Asp Thr Ala Val Tyr Tyr Cys Ala
                 85                  90                  95
Arg Asp Thr Tyr Leu His Phe Asp Tyr Trp Gly Gln Gly Thr Leu Val
                100                 105                 110
Thr Val Ser Ser
```

<210> SEQ ID NO 74
<211> LENGTH: 116
<212> TYPE: PRT
<213> ORGANISM: Homo sapiens

<400> SEQUENCE: 74

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser His
            20                  25                  30

Trp Leu Ser Trp Val Arg Gln Ala Pro Gly Lys Gly Leu Glu Trp Val
        35                  40                  45

Ser Ala Thr Asn Arg Tyr Gly Tyr Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Thr Tyr Leu His Phe Asp Tyr Trp Gly Gln Gly Thr Leu Val
            100                 105                 110

Thr Val Ser Ser
        115

<210> SEQ ID NO 75
<211> LENGTH: 117
<212> TYPE: PRT
<213> ORGANISM: Homo sapiens

<400> SEQUENCE: 75

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser His
            20                  25                  30

Trp Leu Ser Trp Val Arg Gln Ala Pro Gly Lys Gly Leu Glu Trp Val
        35                  40                  45

Ser Asn Ile Asn Tyr Asp Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Tyr Leu His Phe Asp Tyr Trp Gly Gln Gly Thr Leu
            100                 105                 110

Val Thr Val Ser Ser
        115

<210> SEQ ID NO 76
<211> LENGTH: 116
<212> TYPE: PRT
<213> ORGANISM: Homo sapiens

<400> SEQUENCE: 76

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser His
            20                  25                  30

```
Trp Leu Ser Trp Val Arg Gln Ala Pro Gly Lys Gly Leu Glu Trp Val
            35                  40                  45

Ser Val Ile Thr Pro Tyr Gly Asp Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Asp Thr Tyr Leu His Phe Asp Tyr Trp Gly Gln Gly Thr Leu Val
                100                 105                 110

Thr Val Ser Ser
            115

<210> SEQ ID NO 77
<211> LENGTH: 116
<212> TYPE: PRT
<213> ORGANISM: Homo sapiens

<400> SEQUENCE: 77

Gln Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Arg Ser His
             20                  25                  30

Trp Leu Ser Trp Val Arg Gln Ala Pro Gly Lys Gly Leu Glu Trp Val
            35                  40                  45

Ser Val Ile Thr Pro Tyr Gly Asp Thr Tyr Tyr Ala Asp Ser Val Lys
 50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Asp Thr Tyr Leu His Phe Asp Tyr Trp Gly Gln Gly Thr Leu Val
                100                 105                 110

Thr Val Ser Ser
            115

<210> SEQ ID NO 78
<211> LENGTH: 110
<212> TYPE: PRT
<213> ORGANISM: Homo sapiens

<400> SEQUENCE: 78

Asp Ile Glu Leu Thr Gln Pro Pro Ser Val Ser Val Ala Pro Gly Gln
 1               5                  10                  15

Thr Ala Arg Ile Ser Cys Ser Gly Asp Asn Ile Gly Ser Phe Tyr Val
             20                  25                  30

His Trp Tyr Gln Gln Lys Pro Gly Gln Ala Pro Val Leu Val Ile Tyr
            35                  40                  45

Asp Asp Asn Asn Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gly Ser Trp Ala Gly Ser Ser Gly Ser
                 85                  90                  95

Tyr Val Phe Gly Gly Arg Thr Lys Leu Thr Val Leu Gly Gln
                100                 105                 110
```

<210> SEQ ID NO 79
<211> LENGTH: 113
<212> TYPE: PRT
<213> ORGANISM: Homo sapiens

<400> SEQUENCE: 79

```
Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asp Ile
            20                  25                  30

Asn Asp Val Ser Trp Tyr Gln Gln His Pro Gly Lys Ala Pro Lys Leu
        35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Gly Glu Ser
                85                  90                  95

Leu Thr Ser Tyr Val Phe Gly Gly Gly Thr Lys Leu Thr Val Leu Gly
            100                 105                 110

Gln
```

<210> SEQ ID NO 80
<211> LENGTH: 110
<212> TYPE: PRT
<213> ORGANISM: Homo sapiens

<400> SEQUENCE: 80

```
Asp Ile Glu Leu Thr Gln Pro Pro Ser Val Ser Val Ala Pro Gly Gln
1               5                   10                  15

Thr Ala Arg Ile Ser Cys Ser Gly Asp Asn Ile Gly Ser Phe Tyr Val
            20                  25                  30

His Trp Tyr Gln Gln Lys Pro Gly Gln Ala Pro Val Leu Val Ile Tyr
        35                  40                  45

Asp Asp Asn Asn Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ala Ser Trp Thr Gly Val Glu Pro Asp
                85                  90                  95

Tyr Val Phe Gly Gly Gly Thr Lys Leu Thr Val Leu Gly Gln
            100                 105                 110
```

<210> SEQ ID NO 81
<211> LENGTH: 113
<212> TYPE: PRT
<213> ORGANISM: Homo sapiens

<400> SEQUENCE: 81

```
Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asp Ile
            20                  25                  30

Asn Asp Val Ser Trp Tyr Gln Gln His Pro Gly Lys Ala Pro Lys Leu
        35                  40                  45

Met Ile Tyr Asp Val Asn Asn Arg Pro Ser Gly Val Ser Asn Arg Phe
```

```
            50                  55                  60
Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Ser Tyr Ala Gly Ser
                 85                  90                  95

Tyr Leu Ser Glu Val Phe Gly Gly Gly Thr Lys Leu Thr Val Leu Gly
                100                 105                 110

Gln

<210> SEQ ID NO 82
<211> LENGTH: 113
<212> TYPE: PRT
<213> ORGANISM: Homo sapiens

<400> SEQUENCE: 82

Asp Ile Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Asp Ile
                 20                  25                  30

Asn Asp Val Ser Trp Tyr Gln Gln His Pro Gly Lys Ala Pro Lys Leu
             35                  40                  45

Met Ile Tyr Asp Val Asn Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Gly Glu Ser
                 85                  90                  95

Leu Thr Ser Tyr Val Phe Gly Gly Gly Thr Lys Leu Thr Val Leu Gly
                100                 105                 110

Gln

<210> SEQ ID NO 83
<211> LENGTH: 113
<212> TYPE: PRT
<213> ORGANISM: Homo sapiens

<400> SEQUENCE: 83

Asp Ile Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Asp Ile
                 20                  25                  30

Asn Asp Val Ser Trp Tyr Gln Gln His Pro Gly Lys Ala Pro Lys Leu
             35                  40                  45

Met Ile Tyr Asp Val Asn Asn Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Gly Glu Ser
                 85                  90                  95

Leu Thr Ser Tyr Val Phe Gly Gly Gly Thr Lys Leu Thr Val Leu Gly
                100                 105                 110

Gln

<210> SEQ ID NO 84
<211> LENGTH: 113
<212> TYPE: PRT
```

<213> ORGANISM: Homo sapiens

<400> SEQUENCE: 84

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asp Ile
            20                  25                  30

Asn Asp Val Ser Trp Tyr Gln Gln His Pro Gly Lys Ala Pro Lys Leu
        35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Gly Glu Ser
                85                  90                  95

Leu Thr Ser Tyr Val Phe Gly Gly Gly Thr Lys Leu Thr Val Leu Gly
            100                 105                 110

Gln

<210> SEQ ID NO 85
<211> LENGTH: 113
<212> TYPE: PRT
<213> ORGANISM: Homo sapiens

<400> SEQUENCE: 85

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asp Ile
            20                  25                  30

Asn Asp Val Ser Trp Tyr Gln Gln His Pro Gly Lys Ala Pro Lys Leu
        35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Gly Glu Ser
                85                  90                  95

Leu Thr Ser Tyr Val Phe Gly Gly Gly Thr Lys Leu Thr Val Leu Gly
            100                 105                 110

Gln

<210> SEQ ID NO 86
<211> LENGTH: 113
<212> TYPE: PRT
<213> ORGANISM: Homo sapiens

<400> SEQUENCE: 86

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asp Ile
            20                  25                  30

Asn Asp Val Ser Trp Tyr Gln Gln His Pro Gly Lys Ala Pro Lys Leu
        35                  40                  45

Met Ile Tyr Asp Val Asn Asn Arg Pro Ser Gly Val Ser Asn Arg Phe
    50                  55                  60

Ser Gly Ser Lys Ser Gly Asn Thr Ala Ser Leu Thr Ile Ser Gly Leu

```
                65                  70                  75                  80
Gln Ala Glu Asp Glu Ala Asp Tyr Tyr Cys Ser Thr Tyr Asp Gly Pro
                    85                  90                  95

Gly Leu Ser Glu Val Phe Gly Gly Gly Thr Lys Leu Thr Val Leu Gly
                100                 105                 110

Gln
```

<210> SEQ ID NO 87
<211> LENGTH: 113
<212> TYPE: PRT
<213> ORGANISM: Homo sapiens

<400> SEQUENCE: 87

```
Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asp Ile
                20                  25                  30

Asn Asp Val Ser Trp Tyr Gln Gln His Pro Gly Lys Ala Pro Lys Leu
                35                  40                  45

Met Ile Tyr Asp Val Asn Asn Arg Pro Ser Gly Val Ser Asn Arg Phe
            50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Gly Glu Ser
                    85                  90                  95

Leu Thr Ser Tyr Val Phe Gly Gly Gly Thr Lys Leu Thr Val Leu Gly
                100                 105                 110

Gln
```

<210> SEQ ID NO 88
<211> LENGTH: 113
<212> TYPE: PRT
<213> ORGANISM: Homo sapiens

<400> SEQUENCE: 88

```
Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Asp Ile
                20                  25                  30

Asn Asp Val Ser Trp Tyr Gln Gln His Pro Gly Lys Ala Pro Lys Leu
                35                  40                  45

Met Ile Tyr Asp Val Asn Asn Arg Pro Ser Gly Val Ser Asn Arg Phe
            50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Thr Tyr Asp Gly Pro
                    85                  90                  95

Gly Leu Ser Glu Val Phe Gly Gly Gly Thr Lys Leu Thr Val Leu Gly
                100                 105                 110

Gln
```

<210> SEQ ID NO 89
<211> LENGTH: 372
<212> TYPE: DNA
<213> ORGANISM: Homo sapiens

<400> SEQUENCE: 89

```
caggtgcaat tggtggaaag cggcggcggc ctggtgcaac cgggcggcag cctgcgtctg    60
agctgcgcgg cctccggatt tacctttttct tcttatgtta tgaattgggt gcgccaagcc   120
cctgggaagg gtctcgagtg ggtgagcttt atctctggtg attctagcaa tacctattat   180
gcggatagcg tgaaaggccg ttttaccatt tcacgtgata attcgaaaaa cacccctgtat  240 ctgcaaatga acagcctgcg tgcggaagat acggccgtgt attattgcgc gcgtactttt   300
atgcatggtc atcttggtgg tggtctttct atggattttt ggggccaagg caccctggtg   360
acggttagct ca                                                        372

<210> SEQ ID NO 90
<211> LENGTH: 351
<212> TYPE: DNA
<213> ORGANISM: Homo sapiens

<400> SEQUENCE: 90
caggtgcaat tggtggaaag cggcggcggc ctggtgcaac cgggcggcag cctgcgtctg    60
agctgcgcgg cctccggatt tacctttcgt tctcattggc tttcttgggt gcgccaagcc   120
cctgggaagg gtctcgagtg ggtgagcaat atcaattatg atggtagctc tacctattat   180
gcggatagcg tgaaaggccg ttttaccatt tcacgtgata attcgaaaaa cacccctgtat  240 ctgcaaatga acagcctgcg tgcggaagat acggccgtgt attattgcgc gcgtgatact   300
tatcttcatt ttgattattg gggccaaggc accctggtga cggttagctc a            351

<210> SEQ ID NO 91
<211> LENGTH: 372
<212> TYPE: DNA
<213> ORGANISM: Homo sapiens

<400> SEQUENCE: 91
caggtgcaat tggtggaaag cggcggcggc ctggtgcaac cgggcggcag cctgcgtctg    60
agctgcgcgg cctccggatt tacctttttct tcttatgtta tgaattgggt gcgccaagcc   120
cctgggaagg gtctcgagtg ggtgagcttt atctctggtg attctagcaa tacctattat   180
gcggatagcg tgaaaggccg ttttaccatt tcacgtgata attcgaaaaa cacccctgtat  240 ctgcaaatga acagcctgcg tgcggaagat acggccgtgt attattgcgc gcgtactttt   300
atgcatggtc atcttggtgg tggtctttct atggattttt ggggccaagg caccctggtg   360
acggttagct ca                                                        372

<210> SEQ ID NO 92
<211> LENGTH: 351
<212> TYPE: DNA
<213> ORGANISM: Homo sapiens

<400> SEQUENCE: 92
caggtgcaat tggtggaaag cggcggcggc ctggtgcaac cgggcggcag cctgcgtctg    60
agctgcgcgg cctccggatt tacctttcgt tctcattggc tttcttgggt gcgccaagcc   120
cctgggaagg gtctcgagtg ggtgagcaat atcaattatg atggtagctc tacctattat   180
gcggatagcg tgaaaggccg ttttaccatt tcacgtgata attcgaaaaa cacccctgtat  240 ctgcaaatga acagcctgcg tgcggaagat acggccgtgt attattgcgc gcgtgatact   300
tatcttcatt ttgattattg gggccaaggc accctggtga cggttagctc a            351

<210> SEQ ID NO 93
```

```
<211> LENGTH: 348
<212> TYPE: DNA
<213> ORGANISM: Homo sapiens

<400> SEQUENCE: 93
caggtgcaat tggtggaaag cggcggcggc ctggtgcaac cgggcggcag cctgcgtctg      60
agctgcgcgg cctccggatt tacctttcgt tctcattggc tttcttgggt gcgccaagcc     120
cctgggaagg gtctcgagtg ggtgagcgtt actggtgttc atggtgatac ttattatgct     180
gattctgtta agggtcgttt taccatttca cgtgataatt cgaaaaacac cctgtatctg     240
caaatgaaca gcctgcgtgc ggaagatacg gccgtgtatt attgcgcgcg tgatacttat     300
cttcattttg attattgggg ccaaggcacc ctggtgacgg ttagctca                   348

<210> SEQ ID NO 94
<211> LENGTH: 348
<212> TYPE: DNA
<213> ORGANISM: Homo sapiens

<400> SEQUENCE: 94
caggtgcaat tggtggaaag cggcggcggc ctggtgcaac cgggcggcag cctgcgtctg      60
agctgcgcgg cctccggatt tacctttcgt tctcattggc tttcttgggt gcgccaagcc     120
cctgggaagg gtctcgagtg ggtgagcgtt attggtaatt ggggtgatac ttattatgct     180
gattctgtta agggtcgttt taccatttca cgtgataatt cgaaaaacac cctgtatctg     240
caaatgaaca gcctgcgtgc ggaagatacg gccgtgtatt attgcgcgcg tgatacttat     300
cttcattttg attattgggg ccaaggcacc ctggtgacgg ttagctca                   348

<210> SEQ ID NO 95
<211> LENGTH: 348
<212> TYPE: DNA
<213> ORGANISM: Homo sapiens

<400> SEQUENCE: 95
caggtgcaat tggtggaaag cggcggcggc ctggtgcaac cgggcggcag cctgcgtctg      60
agctgcgcgg cctccggatt tacctttcgt tctcattggc tttcttgggt gcgccaagcc     120
cctgggaagg gtctcgagtg ggtgagcgtt actactcatc agggttatac ttattatgct     180
gattctgtta agggtcgttt taccatttca cgtgataatt cgaaaaacac cctgtatctg     240
caaatgaaca gcctgcgtgc ggaagatacg gccgtgtatt attgcgcgcg tgatacttat     300
cttcattttg attattgggg ccaaggcacc ctggtgacgg ttagctca                   348

<210> SEQ ID NO 96
<211> LENGTH: 348
<212> TYPE: DNA
<213> ORGANISM: Homo sapiens

<400> SEQUENCE: 96
caggtgcaat tggtggaaag cggcggcggc ctggtgcaac cgggcggcag cctgcgtctg      60
agctgcgcgg cctccggatt tacctttcgt tctcattggc tttcttgggt gcgccaagcc     120
cctgggaagg gtctcgagtg ggtgagcgct actaatcgtt atggttatac ttattatgct     180
gattctgtta agggtcgttt taccatttca cgtgataatt cgaaaaacac cctgtatctg     240
caaatgaaca gcctgcgtgc ggaagatacg gccgtgtatt attgcgcgcg tgatacttat     300
cttcattttg attattgggg ccaaggcacc ctggtgacgg ttagctca                   348
```

<210> SEQ ID NO 97
<211> LENGTH: 351
<212> TYPE: DNA
<213> ORGANISM: Homo sapiens

<400> SEQUENCE: 97

```
caggtgcaat tggtggaaag cggcggcggc ctggtgcaac cgggcggcag cctgcgtctg      60
agctgcgcgg cctccggatt tacctttcgt tctcattggc tttcttgggt gcgccaagcc     120
cctgggaagg gtctcgagtg ggtgagcaat atcaattatg atggtagctc tacctattat     180
gcggatagcg tgaaaggccg ttttaccatt tcacgtgata attcgaaaaa caccctgtat     240
ctgcaaatga acagcctgcg tgcggaagat acggccgtgt attattgcgc gcgtgatact     300
tatcttcatt ttgattattg gggccaaggc accctggtga cggttagctc a              351
```

<210> SEQ ID NO 98
<211> LENGTH: 348
<212> TYPE: DNA
<213> ORGANISM: Homo sapiens

<400> SEQUENCE: 98

```
caggtgcaat tggtggaaag cggcggcggc ctggtgcaac cgggcggcag cctgcgtctg      60
agctgcgcgg cctccggatt tacctttcgt tctcattggc tttcttgggt gcgccaagcc     120
cctgggaagg gtctcgagtg ggtgagcgtt attactcctt atggtgatac ttattatgct     180
gattctgtta agggtcgttt taccatttca cgtgataatt cgaaaaacac cctgtatctg     240
caaatgaaca gcctgcgtgc ggaagatacg gccgtgtatt attgcgcgcg tgatacttat     300
cttcattttg attattgggg ccaaggcacc ctggtgacgg ttagctca                  348
```

<210> SEQ ID NO 99
<211> LENGTH: 348
<212> TYPE: DNA
<213> ORGANISM: Homo sapiens

<400> SEQUENCE: 99

```
caggtgcaat tggtggaaag cggcggcggc ctggtgcaac cgggcggcag cctgcgtctg      60
agctgcgcgg cctccggatt tacctttcgt tctcattggc tttcttgggt gcgccaagcc     120
cctgggaagg gtctcgagtg ggtgagcgtt attactcctt atggtgatac ttattatgct     180
gattctgtta agggtcgttt taccatttca cgtgataatt cgaaaaacac cctgtatctg     240
caaatgaaca gcctgcgtgc ggaagatacg gccgtgtatt attgcgcgcg tgatacttat     300
cttcattttg attattgggg ccaaggcacc ctggtgacgg ttagctca                  348
```

<210> SEQ ID NO 100
<211> LENGTH: 330
<212> TYPE: DNA
<213> ORGANISM: Homo sapiens

<400> SEQUENCE: 100

```
gatatcgaac tgacccagcc gccttcagtg agcgttgcac aggtcagac cgcgcgtatc       60
tcgtgtagcg gcgataatat tggttctttt tatgttcatt ggtaccagca gaaacccggg     120
caggcgccag ttcttgtgat ttatgatgat aataatcgtc cctcaggcat cccggaacgc     180
tttagcggat ccaacagcgg caacaccgcg accctgacca ttagcggcac tcaggcggaa     240
gacgaagcgg attattattg cggttcttgg gctggttctt ctggttctta tgtgtttggc     300
ggccgcacga agttaaccgt tcttggccag                                      330
```

<210> SEQ ID NO 101
<211> LENGTH: 339
<212> TYPE: DNA
<213> ORGANISM: Homo sapiens

<400> SEQUENCE: 101

```
gatatcgcac tgacccagcc agcttcagtg agcggctcac caggtcagag cattaccatc      60
tcgtgtacgg gtactagcag cgatgttggt gatattaatg atgtgtcttg gtaccagcag     120
catcccggga aggcgccgaa acttatgatt tatgatgtta ataatcgtcc ctcaggcgtg     180
agcaaccgtt ttagcggatc caaaagcggc aacaccgcga gcctgaccat tagcggcctg     240
caagcggaag acgaagcgga ttattattgc tcttcttatg gtgagtctct tacttcttat     300
gtgtttggcg gcggcacgaa gttaaccgtt cttggccag                            339
```

<210> SEQ ID NO 102
<211> LENGTH: 330
<212> TYPE: DNA
<213> ORGANISM: Homo sapiens

<400> SEQUENCE: 102

```
gatatcgaac tgacccagcc gccttcagtg agcgttgcac caggtcagac cgcgcgtatc      60
tcgtgtagcg gcgataatat tggttctttt tatgttcatt ggtaccagca gaaacccggg     120
caggcgccat tcttgtgat ttatgatgat aataatcgtc cctcaggcat cccggaacgc      180
tttagcggat ccaacagcgg caacaccgcg accctgacca ttagcggcac tcaggcggaa     240
gacgaagcgg attattattg cgcttcttgg actggtgttg agcctgatta tgtgtttggc     300
ggcggcacga agttaaccgt tcttggccag                                       330
```

<210> SEQ ID NO 103
<211> LENGTH: 339
<212> TYPE: DNA
<213> ORGANISM: Homo sapiens

<400> SEQUENCE: 103

```
gatatcgcac tgacccagcc agcttcagtg agcggctcac caggtcagag cattaccatc      60
tcgtgtacgg gtactagcag cgatgttggt gatattaatg atgtgtcttg gtaccagcag     120
catcccggga aggcgccgaa acttatgatt tatgatgtta ataatcgtcc ctcaggcgtg     180
agcaaccgtt ttagcggatc caaaagcggc aacaccgcga gcctgaccat tagcggcctg     240
caagcggaag acgaagcgga ttattattgc cagtcttatg ctggttctta tctttctgag     300
gtgtttggcg gcggcacgaa gttaaccgtt cttggccag                            339
```

<210> SEQ ID NO 104
<211> LENGTH: 339
<212> TYPE: DNA
<213> ORGANISM: Homo sapiens

<400> SEQUENCE: 104

```
gatatcgcac tgacccagcc agcttcagtg agcggctcac caggtcagag cattaccatc      60
tcgtgtacgg gtactagcag cgatgttggt gatattaatg atgtgtcttg gtaccagcag     120
catcccggga aggcgccgaa acttatgatt tatgatgtta ataatcgtcc ctcaggcgtg     180
agcaaccgtt ttagcggatc caaaagcggc aacaccgcga gcctgaccat tagcggcctg     240
caagcggaag acgaagcgga ttattattgc tcttcttatg gtgagtctct tacttcttat     300
gtgtttggcg gcggcacgaa gttaaccgtt cttggccag                            339
```

<210> SEQ ID NO 105
<211> LENGTH: 339
<212> TYPE: DNA
<213> ORGANISM: Homo sapiens

<400> SEQUENCE: 105

| | | | | | |
|---|---|---|---|---|---|
| gatatcgcac | tgacccagcc | agcttcagtg | agcggctcac | caggtcagag | cattaccatc | 60 |
| tcgtgtacgg | gtactagcag | cgatgttggt | gatattaatg | atgtgtcttg | gtaccagcag | 120 |
| catcccggga | aggcgccgaa | acttatgatt | tatgatgtta | ataatcgtcc | ctcaggcgtg | 180 |
| agcaaccgtt | ttagcggatc | caaaagcggc | aacaccgcga | gcctgaccat | tagcggcctg | 240 |
| caagcggaag | acgaagcgga | ttattattgc | tcttcttatg | gtgagtctct | tacttcttat | 300 |
| gtgtttggcg | gcggcacgaa | gttaaccgtt | cttggccag | | | 339 |

<210> SEQ ID NO 106
<211> LENGTH: 339
<212> TYPE: DNA
<213> ORGANISM: Homo sapiens

<400> SEQUENCE: 106

| | | | | | |
|---|---|---|---|---|---|
| gatatcgcac | tgacccagcc | agcttcagtg | agcggctcac | caggtcagag | cattaccatc | 60 |
| tcgtgtacgg | gtactagcag | cgatgttggt | gatattaatg | atgtgtcttg | gtaccagcag | 120 |
| catcccggga | aggcgccgaa | acttatgatt | tatgatgtta | ataatcgtcc | ctcaggcgtg | 180 |
| agcaaccgtt | ttagcggatc | caaaagcggc | aacaccgcga | gcctgaccat | tagcggcctg | 240 |
| caagcggaag | acgaagcgga | ttattattgc | tcttcttatg | gtgagtctct | tacttcttat | 300 |
| gtgtttggcg | gcggcacgaa | gttaaccgtt | cttggccag | | | 339 |

<210> SEQ ID NO 107
<211> LENGTH: 339
<212> TYPE: DNA
<213> ORGANISM: Homo sapiens

<400> SEQUENCE: 107

| | | | | | |
|---|---|---|---|---|---|
| gatatcgcac | tgacccagcc | agcttcagtg | agcggctcac | caggtcagag | cattaccatc | 60 |
| tcgtgtacgg | gtactagcag | cgatgttggt | gatattaatg | atgtgtcttg | gtaccagcag | 120 |
| catcccggga | aggcgccgaa | acttatgatt | tatgatgtta | ataatcgtcc | ctcaggcgtg | 180 |
| agcaaccgtt | ttagcggatc | caaaagcggc | aacaccgcga | gcctgaccat | tagcggcctg | 240 |
| caagcggaag | acgaagcgga | ttattattgc | tcttcttatg | gtgagtctct | tacttcttat | 300 |
| gtgtttggcg | gcggcacgaa | gttaaccgtt | cttggccag | | | 339 |

<210> SEQ ID NO 108
<211> LENGTH: 339
<212> TYPE: DNA
<213> ORGANISM: Homo sapiens

<400> SEQUENCE: 108

| | | | | | |
|---|---|---|---|---|---|
| gatatcgcac | tgacccagcc | agcttcagtg | agcggctcac | caggtcagag | cattaccatc | 60 |
| tcgtgtacgg | gtactagcag | cgatgttggt | gatattaatg | atgtgtcttg | gtaccagcag | 120 |
| catcccggga | aggcgccgaa | acttatgatt | tatgatgtta | ataatcgtcc | ctcaggcgtg | 180 |
| agcaaccgtt | ttagcggatc | caaaagcggc | aacaccgcga | gcctgaccat | tagcggcctg | 240 |
| caagcggaag | acgaagcgga | ttattattgc | tctacttatg | atggtcctgg | tctttctgag | 300 |

```
gtgtttggcg gcggcacgaa gttaaccgtt cttggccag                          339
```

<210> SEQ ID NO 109
<211> LENGTH: 339
<212> TYPE: DNA
<213> ORGANISM: Homo sapiens

<400> SEQUENCE: 109

```
gatatcgcac tgacccagcc agcttcagtg agcggctcac caggtcagag cattaccatc    60
tcgtgtacgg gtactagcag cgatgttggt gatattaatg atgtgtcttg gtaccagcag   120
catcccggga aggcgccgaa acttatgatt tatgatgtta ataatcgtcc ctcaggcgtg   180
agcaaccgtt ttagcggatc caaaagcggc aacaccgcga gcctgaccat tagcggcctg   240
caagcggaag acgaagcgga ttattattgc tcttcttatg gtgagtctct tacttcttat   300
gtgtttggcg gcggcacgaa gttaaccgtt cttggccag                          339
```

<210> SEQ ID NO 110
<211> LENGTH: 339
<212> TYPE: DNA
<213> ORGANISM: Homo sapiens

<400> SEQUENCE: 110

```
gatatcgcac tgacccagcc agcttcagtg agcggctcac caggtcagag cattaccatc    60
tcgtgtacgg gtactagcag cgatgttggt gatattaatg atgtgtcttg gtaccagcag   120
catcccggga aggcgccgaa acttatgatt tatgatgtta ataatcgtcc ctcaggcgtg   180
agcaaccgtt ttagcggatc caaaagcggc aacaccgcga gcctgaccat tagcggcctg   240
caagcggaag acgaagcgga ttattattgc tctacttatg atggtcctgg tctttctgag   300
gtgtttggcg gcggcacgaa gttaaccgtt cttggccag                          339
```

<210> SEQ ID NO 111
<211> LENGTH: 469
<212> TYPE: PRT
<213> ORGANISM: Homo sapiens

<400> SEQUENCE: 111

```
Met Ala Trp Val Trp Thr Leu Pro Phe Leu Met Ala Ala Ala Gln Ser
1               5                   10                  15

Val Gln Ala Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Val Met Asn Trp Val Arg Gln Ala Pro Gly Lys Gly Leu
    50                  55                  60

Glu Trp Val Ser Phe Ile Ser Gly Asp Ser Asn Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Thr Phe Met His Gly His Leu Gly Gly Leu
        115                 120                 125

Ser Met Asp Phe Trp Gly Gln Gly Thr Leu Val Thr Val Ser Ser Ala
    130                 135                 140

Ser Thr Lys Gly Pro Ser Val Phe Pro Leu Ala Pro Cys Ser Arg Ser
145                 150                 155                 160
```

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Asn Phe Gly Thr Gln Thr Tyr
    210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Pro
                245                 250                 255

Val Ala Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Gln Phe Asn Trp Tyr Val Asp Gly Val
    290                 295                 300

Glu Val His Asn Ala Lys Thr Lys Pro Arg Glu Glu Gln Phe Asn Ser
305                 310                 315                 320

Thr Phe Arg Val Val Ser Val Leu Thr Val Val His Gln Asp Trp Leu
                325                 330                 335

Asn Gly Lys Glu Tyr Lys Cys Lys Val Ser Asn Lys Gly Leu Pro Ala
            340                 345                 350

Pro Ile Glu Lys Thr Ile Ser Lys Thr Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Met Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly Lys
465

<210> SEQ ID NO 112
<211> LENGTH: 462
<212> TYPE: PRT
<213> ORGANISM: Homo sapiens

<400> SEQUENCE: 112

Met Ala Trp Val Trp Thr Leu Pro Phe Leu Met Ala Ala Ala Gln Ser
1               5                   10                  15

Val Gln Ala Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Arg Ser His Trp Leu Ser Trp Val Arg Gln Ala Pro Gly Lys Gly Leu

```
                50                  55                  60
Glu Trp Val Ser Asn Ile Asn Tyr Asp Gly Ser Ser Thr Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Ala Glu Asp Thr Ala Val
                100                 105                 110

Tyr Tyr Cys Ala Arg Asp Thr Tyr Leu His Phe Asp Tyr Trp Gly Gln
                115                 120                 125

Gly Thr Leu Val Thr Val Ser Ser Ala Ser Thr Lys Gly Pro Ser Val
                130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
                180                 185                 190

Leu Gln Ser Ser Gly Leu Tyr Ser Leu Ser Ser Val Val Thr Val Pro
                195                 200                 205

Ser Ser Asn Phe Gly Thr Gln Thr Tyr Thr Cys Asn Val Asp His Lys
                210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
                275                 280                 285

Gln Phe Asn Trp Tyr Val Asp Gly Val Glu Val His Asn Ala Lys Thr
                290                 295                 300

Lys Pro Arg Glu Glu Gln Phe Asn Ser Thr Phe Arg Val Val Ser Val
305                 310                 315                 320

Leu Thr Val Val His Gln Asp Trp Leu Asn Gly Lys Glu Tyr Lys Cys
                325                 330                 335

Lys Val Ser Asn Lys Gly Leu Pro Ala Pro Ile Glu Lys Thr Ile Ser
                340                 345                 350

Lys Thr Lys Gly Gln Pro Arg Glu Pro Gln Val Tyr Thr Leu Pro Pro
                355                 360                 365

Ser Arg Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Met Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
                435                 440                 445

Asn His Tyr Thr Gln Lys Ser Leu Ser Leu Ser Pro Gly Lys
450                 455                 460

<210> SEQ ID NO 113
```

```
<211> LENGTH: 469
<212> TYPE: PRT
<213> ORGANISM: Homo sapiens

<400> SEQUENCE: 113

Met Ala Trp Val Trp Thr Leu Pro Phe Leu Met Ala Ala Ala Gln Ser
1               5                   10                  15

Val Gln Ala Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Tyr Val Met Asn Trp Val Arg Gln Ala Pro Gly Lys Gly Leu
    50                  55                  60

Glu Trp Val Ser Phe Ile Ser Gly Asp Ser Ser Asn Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Thr Phe Met His Gly His Leu Gly Gly Gly Leu
        115                 120                 125

Ser Met Asp Phe Trp Gly Gln Gly Thr Leu Val Thr Val Ser Ser Ala
    130                 135                 140

Ser Thr Lys Gly Pro Ser Val Phe Pro Leu Ala Pro Cys Ser Arg Ser
145                 150                 155                 160

Thr Ser Glu Ser Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Asn Phe Gly Thr Gln Thr Tyr
    210                 215                 220

Thr Cys Asn Val Asp His Lys Pro Ser Asn Thr Lys Val Asp Lys Thr
225                 230                 235                 240

Val Glu Arg Lys Cys Cys Val Glu Cys Pro Pro Cys Pro Ala Pro Pro
                245                 250                 255

Val Ala Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Gln Phe Asn Trp Tyr Val Asp Gly Val
    290                 295                 300

Glu Val His Asn Ala Lys Thr Lys Pro Arg Glu Glu Gln Phe Asn Ser
305                 310                 315                 320

Thr Phe Arg Val Val Ser Val Leu Thr Val Val His Gln Asp Trp Leu
                325                 330                 335

Asn Gly Lys Glu Tyr Lys Cys Lys Val Ser Asn Lys Gly Leu Pro Ala
            340                 345                 350

Pro Ile Glu Lys Thr Ile Ser Lys Thr Lys Gly Gln Pro Arg Glu Pro
        355                 360                 365

Gln Val Tyr Thr Leu Pro Pro Ser Arg Glu Glu Met Thr Lys Asn Gln
    370                 375                 380

Val Ser Leu Thr Cys Leu Val Lys Gly Phe Tyr Pro Ser Asp Ile Ala
```

```
385                 390                 395                 400
Val Glu Trp Glu Ser Asn Gly Gln Pro Glu Asn Asn Tyr Lys Thr Thr
                405                 410                 415

Pro Pro Met Leu Asp Ser Asp Gly Ser Phe Phe Leu Tyr Ser Lys Leu
                420                 425                 430

Thr Val Asp Lys Ser Arg Trp Gln Gln Gly Asn Val Phe Ser Cys Ser
                435                 440                 445

Val Met His Glu Ala Leu His Asn His Tyr Thr Gln Lys Ser Leu Ser
                450                 455                 460

Leu Ser Pro Gly Lys
465

<210> SEQ ID NO 114
<211> LENGTH: 462
<212> TYPE: PRT
<213> ORGANISM: Homo sapiens

<400> SEQUENCE: 114

Met Ala Trp Val Trp Thr Leu Pro Phe Leu Met Ala Ala Ala Gln Ser
1               5                   10                  15

Val Gln Ala Gln Val Gln Leu Val Glu Ser Gly Gly Gly Leu Val Gln
                20                  25                  30

Pro Gly Gly Ser Leu Arg Leu Ser Cys Ala Ala Ser Gly Phe Thr Phe
                35                  40                  45

Arg Ser His Trp Leu Ser Trp Val Arg Gln Ala Pro Gly Lys Gly Leu
                50                  55                  60

Glu Trp Val Ser Asn Ile Asn Tyr Asp Gly Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
                100                 105                 110

Tyr Tyr Cys Ala Arg Asp Thr Tyr Leu His Phe Asp Tyr Trp Gly Gln
                115                 120                 125

Gly Thr Leu Val Thr Val Ser Ser Ala Ser Thr Lys Gly Pro Ser Val
                130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
                180                 185                 190

Leu Gln Ser Ser Gly Leu Tyr Ser Leu Ser Ser Val Val Thr Val Pro
                195                 200                 205

Ser Ser Asn Phe Gly Thr Gln Thr Tyr Thr Cys Asn Val Asp His Lys
                210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser His Glu Asp Pro Glu Val
                275                 280                 285
```

-continued

```
Gln Phe Asn Trp Tyr Val Asp Gly Val Glu Val His Asn Ala Lys Thr
290                 295                 300
Lys Pro Arg Glu Glu Gln Phe Asn Ser Thr Phe Arg Val Val Ser Val
305                 310                 315                 320
Leu Thr Val Val His Gln Asp Trp Leu Asn Gly Lys Glu Tyr Lys Cys
            325                 330                 335
Lys Val Ser Asn Lys Gly Leu Pro Ala Pro Ile Glu Lys Thr Ile Ser
            340                 345                 350
Lys Thr Lys Gly Gln Pro Arg Glu Pro Gln Val Tyr Thr Leu Pro Pro
            355                 360                 365
Ser Arg Glu Glu Met Thr Lys Asn Gln Val Ser Leu Thr Cys Leu Val
370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Met Leu Asp Ser Asp
            405                 410                 415
Gly Ser Phe Phe Leu Tyr Ser Lys Leu Thr Val Asp Lys Ser Arg Trp
            420                 425                 430
Gln Gln Gly Asn Val Phe Ser Cys Ser Val Met His Glu Ala Leu His
            435                 440                 445
Asn His Tyr Thr Gln Lys Ser Leu Ser Leu Ser Pro Gly Lys
450                 455                 460

<210> SEQ ID NO 115
<211> LENGTH: 461
<212> TYPE: PRT
<213> ORGANISM: Homo sapiens

<400> SEQUENCE: 115

Met Ala Trp Val Trp Thr Leu Pro Phe Leu Met Ala Ala Ala Gln Ser
1               5                   10                  15
Val Gln Ala Gln Val Gln Leu Val Glu Ser Gly Gly Gly Leu Val Gln
            20                  25                  30
Pro Gly Gly Ser Leu Arg Leu Ser Cys Ala Ala Ser Gly Phe Thr Phe
        35                  40                  45
Arg Ser His Trp Leu Ser Trp Val Arg Gln Ala Pro Gly Lys Gly Leu
50                  55                  60
Glu Trp Val Ser Val Thr Gly Val His Gly Asp Thr Tyr Tyr Ala Asp
65                  70                  75                  80
Ser Val Lys Gly Arg Phe Thr Ile Ser Arg Asp Asn Ser Lys Asn Thr
                85                  90                  95
Leu Tyr Leu Gln Met Asn Ser Leu Arg Ala Glu Asp Thr Ala Val Tyr
            100                 105                 110
Tyr Cys Ala Arg Asp Thr Tyr Leu His Phe Asp Tyr Trp Gly Gln Gly
        115                 120                 125
Thr Leu Val Thr Val Ser Ser Ala Ser Thr Lys Gly Pro Ser Val Phe
    130                 135                 140
Pro Leu Ala Pro Cys Ser Arg Ser Thr Ser Glu Ser Thr Ala Ala Leu
145                 150                 155                 160
Gly Cys Leu Val Lys Asp Tyr Phe Pro Glu Pro Val Thr Val Ser Trp
                165                 170                 175
Asn Ser Gly Ala Leu Thr Ser Gly Val His Thr Phe Pro Ala Val Leu
            180                 185                 190
Gln Ser Ser Gly Leu Tyr Ser Leu Ser Ser Val Val Thr Val Pro Ser
        195                 200                 205
```

Ser Asn Phe Gly Thr Gln Thr Tyr Thr Cys Asn Val Asp His Lys Pro
210                 215                 220

Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
            245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Gln
        275                 280                 285

Phe Asn Trp Tyr Val Asp Gly Val Glu Val His Asn Ala Lys Thr Lys
290                 295                 300

Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
                325                 330                 335

Val Ser Asn Lys Gly Leu Pro Ala Pro Ile Glu Lys Thr Ile Ser Lys
            340                 345                 350

Thr Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Met Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
450                 455                 460

<210> SEQ ID NO 116
<211> LENGTH: 461
<212> TYPE: PRT
<213> ORGANISM: Homo sapiens

<400> SEQUENCE: 116

Met Ala Trp Val Trp Thr Leu Pro Phe Leu Met Ala Ala Ala Gln Ser
1               5                   10                  15

Val Gln Ala Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Arg Ser His Trp Leu Ser Trp Val Arg Gln Ala Pro Gly Lys Gly Leu
    50                  55                  60

Glu Trp Val Ser Val Ile Gly Asn Trp Gly Asp Thr Tyr Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Asp Thr Tyr Leu His Phe Asp Tyr Trp Gly Gln Gly

```
            115                 120                 125
Thr Leu Val Thr Val Ser Ser Ala Ser Thr Lys Gly Pro Ser Val Phe
            130                 135                 140
Pro Leu Ala Pro Cys Ser Arg Ser Thr Ser Glu Ser Thr Ala Ala Leu
145                 150                 155                 160
Gly Cys Leu Val Lys Asp Tyr Phe Pro Glu Pro Val Thr Val Ser Trp
                165                 170                 175
Asn Ser Gly Ala Leu Thr Ser Gly Val His Thr Phe Pro Ala Val Leu
            180                 185                 190
Gln Ser Ser Gly Leu Tyr Ser Leu Ser Ser Val Val Thr Val Pro Ser
        195                 200                 205
Ser Asn Phe Gly Thr Gln Thr Tyr Thr Cys Asn Val Asp His Lys Pro
210                 215                 220
Ser Asn Thr Lys Val Asp Lys Thr Val Glu Arg Lys Cys Cys Val Glu
225                 230                 235                 240
Cys Pro Pro Cys Pro Ala Pro Pro Val Ala Gly Pro Ser Val Phe Leu
                245                 250                 255
Phe Pro Pro Lys Pro Lys Asp Thr Leu Met Ile Ser Arg Thr Pro Glu
            260                 265                 270
Val Thr Cys Val Val Asp Val Ser His Glu Asp Pro Glu Val Gln
        275                 280                 285
Phe Asn Trp Tyr Val Asp Gly Val Glu Val His Asn Ala Lys Thr Lys
    290                 295                 300
Pro Arg Glu Glu Gln Phe Asn Ser Thr Phe Arg Val Val Ser Val Leu
305                 310                 315                 320
Thr Val Val His Gln Asp Trp Leu Asn Gly Lys Glu Tyr Lys Cys Lys
                325                 330                 335
Val Ser Asn Lys Gly Leu Pro Ala Pro Ile Glu Lys Thr Ile Ser Lys
            340                 345                 350
Thr Lys Gly Gln Pro Arg Glu Pro Gln Val Tyr Thr Leu Pro Pro Ser
        355                 360                 365
Arg Glu Glu Met Thr Lys Asn Gln Val Ser Leu Thr Cys Leu Val Lys
370                 375                 380
Gly Phe Tyr Pro Ser Asp Ile Ala Val Glu Trp Glu Ser Asn Gly Gln
385                 390                 395                 400
Pro Glu Asn Asn Tyr Lys Thr Thr Pro Pro Met Leu Asp Ser Asp Gly
                405                 410                 415
Ser Phe Phe Leu Tyr Ser Lys Leu Thr Val Asp Lys Ser Arg Trp Gln
            420                 425                 430
Gln Gly Asn Val Phe Ser Cys Ser Val Met His Glu Ala Leu His Asn
        435                 440                 445
His Tyr Thr Gln Lys Ser Leu Ser Leu Ser Pro Gly Lys
450                 455                 460

<210> SEQ ID NO 117
<211> LENGTH: 461
<212> TYPE: PRT
<213> ORGANISM: Homo sapiens

<400> SEQUENCE: 117

Met Ala Trp Val Trp Thr Leu Pro Phe Leu Met Ala Ala Ala Gln Ser
1               5                   10                  15
Val Gln Ala Gln Val Gln Leu Val Glu Ser Gly Gly Gly Leu Val Gln
            20                  25                  30
```

-continued

```
Pro Gly Gly Ser Leu Arg Leu Ser Cys Ala Ala Ser Gly Phe Thr Phe
             35                  40                  45
Arg Ser His Trp Leu Ser Trp Val Arg Gln Ala Pro Gly Lys Gly Leu
 50                  55                  60
Glu Trp Val Ser Val Thr Thr His Gln Gly Tyr Thr Tyr Tyr Ala Asp
 65                  70                  75                  80
Ser Val Lys Gly Arg Phe Thr Ile Ser Arg Asp Asn Ser Lys Asn Thr
                 85                  90                  95
Leu Tyr Leu Gln Met Asn Ser Leu Arg Ala Glu Asp Thr Ala Val Tyr
                100                 105                 110
Tyr Cys Ala Arg Asp Thr Tyr Leu His Phe Asp Tyr Trp Gly Gln Gly
            115                 120                 125
Thr Leu Val Thr Val Ser Ser Ala Ser Thr Lys Gly Pro Ser Val Phe
130                 135                 140
Pro Leu Ala Pro Cys Ser Arg Ser Thr Ser Glu Ser Thr Ala Ala Leu
145                 150                 155                 160
Gly Cys Leu Val Lys Asp Tyr Phe Pro Glu Pro Val Thr Val Ser Trp
                165                 170                 175
Asn Ser Gly Ala Leu Thr Ser Gly Val His Thr Phe Pro Ala Val Leu
            180                 185                 190
Gln Ser Ser Gly Leu Tyr Ser Leu Ser Ser Val Val Thr Val Pro Ser
        195                 200                 205
Ser Asn Phe Gly Thr Gln Thr Tyr Thr Cys Asn Val Asp His Lys Pro
    210                 215                 220
Ser Asn Thr Lys Val Asp Lys Thr Val Glu Arg Lys Cys Cys Val Glu
225                 230                 235                 240
Cys Pro Pro Cys Pro Ala Pro Pro Val Ala Gly Pro Ser Val Phe Leu
                245                 250                 255
Phe Pro Pro Lys Pro Lys Asp Thr Leu Met Ile Ser Arg Thr Pro Glu
            260                 265                 270
Val Thr Cys Val Val Val Asp Val Ser His Glu Asp Pro Glu Val Gln
        275                 280                 285
Phe Asn Trp Tyr Val Asp Gly Val Glu Val His Asn Ala Lys Thr Lys
    290                 295                 300
Pro Arg Glu Glu Gln Phe Asn Ser Thr Phe Arg Val Val Ser Val Leu
305                 310                 315                 320
Thr Val Val His Gln Asp Trp Leu Asn Gly Lys Glu Tyr Lys Cys Lys
                325                 330                 335
Val Ser Asn Lys Gly Leu Pro Ala Pro Ile Glu Lys Thr Ile Ser Lys
            340                 345                 350
Thr Lys Gly Gln Pro Arg Glu Pro Gln Val Tyr Thr Leu Pro Pro Ser
        355                 360                 365
Arg Glu Glu Met Thr Lys Asn Gln Val Ser Leu Thr Cys Leu Val Lys
    370                 375                 380
Gly Phe Tyr Pro Ser Asp Ile Ala Val Glu Trp Glu Ser Asn Gly Gln
385                 390                 395                 400
Pro Glu Asn Asn Tyr Lys Thr Thr Pro Pro Met Leu Asp Ser Asp Gly
                405                 410                 415
Ser Phe Phe Leu Tyr Ser Lys Leu Thr Val Asp Lys Ser Arg Trp Gln
            420                 425                 430
Gln Gly Asn Val Phe Ser Cys Ser Val Met His Glu Ala Leu His Asn
        435                 440                 445
His Tyr Thr Gln Lys Ser Leu Ser Leu Ser Pro Gly Lys
```

```
                   450                 455                 460

<210> SEQ ID NO 118
<211> LENGTH: 465
<212> TYPE: PRT
<213> ORGANISM: Homo sapiens

<400> SEQUENCE: 118

Met Lys His Leu Trp Phe Phe Leu Leu Leu Val Ala Ala Pro Arg Trp
1               5                   10                  15

Val Leu Ser Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Arg Ser His Trp Leu Ser Trp Val Arg Gln Ala Pro Gly Lys Gly Leu
    50                  55                  60

Glu Trp Val Ser Ala Thr Asn Arg Tyr Gly Tyr Thr Tyr Tyr Ala Asp
65                  70                  75                  80

Ser Val Lys Gly Arg Phe Thr Ile Ser Arg Asp Asn Ser Lys Asn Thr
                85                  90                  95

Leu Tyr Leu Gln Met Asn Ser Leu Arg Ala Glu Asp Thr Ala Val Tyr
            100                 105                 110

Tyr Cys Ala Arg Asp Thr Tyr Leu His Phe Asp Tyr Trp Gly Gln Gly
        115                 120                 125

Thr Leu Val Thr Val Ser Ser Ala Lys Thr Thr Ala Pro Ser Val Tyr
    130                 135                 140

Pro Leu Ala Pro Val Cys Gly Asp Thr Thr Gly Ser Ser Val Thr Leu
145                 150                 155                 160

Gly Cys Leu Val Lys Gly Tyr Phe Pro Glu Pro Val Thr Leu Thr Trp
                165                 170                 175

Asn Ser Gly Ser Leu Ser Ser Gly Val His Thr Phe Pro Ala Val Leu
            180                 185                 190

Gln Ser Asp Leu Tyr Thr Leu Ser Ser Ser Val Thr Val Thr Ser Ser
        195                 200                 205

Thr Trp Pro Ser Gln Ser Ile Thr Cys Asn Val Ala His Pro Ala Ser
    210                 215                 220

Ser Thr Lys Val Asp Lys Lys Ile Glu Pro Arg Gly Pro Thr Ile Lys
225                 230                 235                 240

Pro Cys Pro Pro Cys Lys Cys Pro Ala Pro Asn Leu Leu Gly Gly Pro
                245                 250                 255

Ser Val Phe Ile Phe Pro Pro Lys Ile Lys Asp Val Leu Met Ile Ser
            260                 265                 270

Leu Ser Pro Ile Val Thr Cys Val Val Val Asp Val Ser Glu Asp Asp
        275                 280                 285

Pro Asp Val Gln Ile Ser Trp Phe Val Asn Asn Val Glu Val His Thr
    290                 295                 300

Ala Gln Thr Gln Thr His Arg Glu Asp Tyr Asn Ser Thr Leu Arg Val
305                 310                 315                 320

Val Ser Ala Leu Pro Ile Gln His Gln Asp Trp Met Ser Gly Lys Glu
                325                 330                 335

Phe Lys Cys Lys Val Asn Asn Lys Asp Leu Pro Ala Pro Ile Glu Arg
            340                 345                 350

Thr Ile Ser Lys Pro Lys Gly Ser Val Arg Ala Pro Gln Val Tyr Val
        355                 360                 365
```

```
Leu Pro Pro Glu Glu Met Thr Lys Lys Gln Val Thr Leu Thr
    370             375             380

Cys Met Val Thr Asp Phe Met Pro Glu Asp Ile Tyr Val Glu Trp Thr
385             390             395             400

Asn Asn Gly Lys Thr Glu Leu Asn Tyr Lys Asn Thr Glu Pro Val Leu
            405             410             415

Asp Ser Asp Gly Ser Tyr Phe Met Tyr Ser Lys Leu Arg Val Glu Lys
        420             425             430

Lys Asn Trp Val Glu Arg Asn Ser Tyr Ser Cys Ser Val Val His Glu
    435             440             445

Gly Leu His Asn His His Thr Thr Lys Ser Phe Ser Arg Thr Pro Gly
    450             455             460

Lys
465

<210> SEQ ID NO 119
<211> LENGTH: 462
<212> TYPE: PRT
<213> ORGANISM: Homo sapiens

<400> SEQUENCE: 119

Met Ala Trp Val Trp Thr Leu Pro Phe Leu Met Ala Ala Ala Gln Ser
1               5                   10                  15

Val Gln Ala Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Arg Ser His Trp Leu Ser Trp Val Arg Gln Ala Pro Gly Lys Gly Leu
    50                  55                  60

Glu Trp Val Ser Asn Ile Asn Tyr Asp Gly Ser Ser Thr Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Asp Thr Tyr Leu His Phe Asp Tyr Trp Gly Gln
        115                 120                 125

Gly Thr Leu Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Asn Phe Gly Thr Gln Thr Tyr Thr Cys Asn Val Asp His Lys
    210                 215                 220

Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
                245                 250                 255

Leu Phe Pro Pro Lys Pro Lys Asp Thr Leu Met Ile Ser Arg Thr Pro
            260                 265                 270
```

```
Glu Val Thr Cys Val Val Val Asp Val Ser His Glu Asp Pro Glu Val
            275                 280                 285
Gln Phe Asn Trp Tyr Val Asp Gly Val Glu Val His Asn Ala Lys Thr
        290                 295                 300
Lys Pro Arg Glu Glu Gln Phe Asn Ser Thr Phe Arg Val Val Ser Val
305                 310                 315                 320
Leu Thr Val Val His Gln Asp Trp Leu Asn Gly Lys Glu Tyr Lys Cys
                325                 330                 335
Lys Val Ser Asn Lys Gly Leu Pro Ala Pro Ile Glu Lys Thr Ile Ser
            340                 345                 350
Lys Thr Lys Gly Gln Pro Arg Glu Pro Gln Val Tyr Thr Leu Pro Pro
        355                 360                 365
Ser Arg Glu Glu Met Thr Lys Asn Gln Val Ser Leu Thr Cys Leu Val
370                 375                 380
Lys Gly Phe Tyr Pro Ser Asp Ile Ala Val Glu Trp Glu Ser Asn Gly
385                 390                 395                 400
Gln Pro Glu Asn Asn Tyr Lys Thr Thr Pro Pro Met Leu Asp Ser Asp
                405                 410                 415
Gly Ser Phe Phe Leu Tyr Ser Lys Leu Thr Val Asp Lys Ser Arg Trp
            420                 425                 430
Gln Gln Gly Asn Val Phe Ser Cys Ser Val Met His Glu Ala Leu His
        435                 440                 445
Asn His Tyr Thr Gln Lys Ser Leu Ser Leu Ser Pro Gly Lys
450                 455                 460

<210> SEQ ID NO 120
<211> LENGTH: 461
<212> TYPE: PRT
<213> ORGANISM: Homo sapiens

<400> SEQUENCE: 120

Met Ala Trp Val Trp Thr Leu Pro Phe Leu Met Ala Ala Ala Gln Ser
1               5                   10                  15
Val Gln Ala Gln Val Gln Leu Val Glu Ser Gly Gly Gly Leu Val Gln
            20                  25                  30
Pro Gly Gly Ser Leu Arg Leu Ser Cys Ala Ala Ser Gly Phe Thr Phe
        35                  40                  45
Arg Ser His Trp Leu Ser Trp Val Arg Gln Ala Pro Gly Lys Gly Leu
50                  55                  60
Glu Trp Val Ser Val Ile Thr Pro Tyr Gly Asp Thr Tyr Tyr Ala Asp
65                  70                  75                  80
Ser Val Lys Gly Arg Phe Thr Ile Ser Arg Asp Asn Ser Lys Asn Thr
                85                  90                  95
Leu Tyr Leu Gln Met Asn Ser Leu Arg Ala Glu Asp Thr Ala Val Tyr
            100                 105                 110
Tyr Cys Ala Arg Asp Thr Tyr Leu His Phe Asp Tyr Trp Gly Gln Gly
        115                 120                 125
Thr Leu Val Thr Val Ser Ser Ala Ser Thr Lys Gly Pro Ser Val Phe
130                 135                 140
Pro Leu Ala Pro Cys Ser Arg Ser Thr Ser Glu Ser Thr Ala Ala Leu
145                 150                 155                 160
Gly Cys Leu Val Lys Asp Tyr Phe Pro Glu Pro Val Thr Val Ser Trp
                165                 170                 175
Asn Ser Gly Ala Leu Thr Ser Gly Val His Thr Phe Pro Ala Val Leu
```

```
            180                 185                 190
Gln Ser Ser Gly Leu Tyr Ser Leu Ser Ser Val Val Thr Val Pro Ser
            195                 200                 205

Ser Asn Phe Gly Thr Gln Thr Tyr Thr Cys Asn Val Asp His Lys Pro
            210                 215                 220

Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
                245                 250                 255

Phe Pro Pro Lys Pro Lys Asp Thr Leu Met Ile Ser Arg Thr Pro Glu
                260                 265                 270

Val Thr Cys Val Val Val Asp Val Ser His Glu Asp Pro Glu Val Gln
            275                 280                 285

Phe Asn Trp Tyr Val Asp Gly Val Glu Val His Asn Ala Lys Thr Lys
            290                 295                 300

Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
                325                 330                 335

Val Ser Asn Lys Gly Leu Pro Ala Pro Ile Glu Lys Thr Ile Ser Lys
                340                 345                 350

Thr Lys Gly Gln Pro Arg Glu Pro Gln Val Tyr Thr Leu Pro Pro Ser
            355                 360                 365

Arg Glu Glu Met Thr Lys Asn Gln Val Ser Leu Thr Cys Leu Val Lys
            370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Met Leu Asp Ser Asp Gly
                405                 410                 415

Ser Phe Phe Leu Tyr Ser Lys Leu Thr Val Asp Lys Ser Arg Trp Gln
                420                 425                 430

Gln Gly Asn Val Phe Ser Cys Ser Val Met His Glu Ala Leu His Asn
            435                 440                 445

His Tyr Thr Gln Lys Ser Leu Ser Leu Ser Pro Gly Lys
            450                 455                 460

<210> SEQ ID NO 121
<211> LENGTH: 461
<212> TYPE: PRT
<213> ORGANISM: Homo sapiens

<400> SEQUENCE: 121

Met Ala Trp Val Trp Thr Leu Pro Phe Leu Met Ala Ala Ala Gln Ser
1               5                   10                  15

Val Gln Ala Gln Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Arg Ser His Trp Leu Ser Trp Val Arg Gln Ala Pro Gly Lys Gly Leu
    50                  55                  60

Glu Trp Val Ser Val Ile Thr Pro Tyr Gly Asp Thr Tyr Tyr Ala Asp
65                  70                  75                  80

Ser Val Lys Gly Arg Phe Thr Ile Ser Arg Asp Asn Ser Lys Asn Thr
                85                  90                  95
```

```
Leu Tyr Leu Gln Met Asn Ser Leu Arg Ala Glu Asp Thr Ala Val Tyr
                100                 105                 110

Tyr Cys Ala Arg Asp Thr Tyr Leu His Phe Asp Tyr Trp Gly Gln Gly
            115                 120                 125

Thr Leu Val Thr Val Ser Ser Ala Ser Thr Lys Gly Pro Ser Val Phe
        130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
210                 215                 220

Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Asp Val Ser His Glu Asp Pro Glu Val Gln
        275                 280                 285

Phe Asn Trp Tyr Val Asp Gly Val Glu Val His Asn Ala Lys Thr Lys
            290                 295                 300

Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
                325                 330                 335

Val Ser Asn Lys Gly Leu Pro Ala Pro Ile Glu Lys Thr Ile Ser Lys
            340                 345                 350

Thr Lys Gly Gln Pro Arg Glu Pro Gln Val Tyr Thr Leu Pro Pro Ser
        355                 360                 365

Arg Glu Glu Met Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Met Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460

<210> SEQ ID NO 122
<211> LENGTH: 130
<212> TYPE: PRT
<213> ORGANISM: Homo sapiens

<400> SEQUENCE: 122

Met Ser Val Leu Thr Gln Val Leu Ala Leu Leu Leu Leu Trp Leu Thr
1               5                   10                  15
```

Gly Thr Arg Cys Asp Ile Glu Leu Thr Gln Pro Ser Val Ser Val
            20                  25                  30

Ala Pro Gly Gln Thr Ala Arg Ile Ser Cys Ser Gly Asp Asn Ile Gly
        35                  40                  45

Ser Phe Tyr Val His Trp Tyr Gln Gln Lys Pro Gly Gln Ala Pro Val
    50                  55                  60

Leu Val Ile Tyr Asp Asp Asn Arg Pro Ser Gly Ile Pro Glu Arg
65                  70                  75                  80

Phe Ser Gly Ser Asn Ser Gly Asn Thr Ala Thr Leu Thr Ile Ser Gly
                85                  90                  95

Thr Gln Ala Glu Asp Glu Ala Asp Tyr Tyr Cys Gly Ser Trp Ala Gly
            100                 105                 110

Ser Ser Gly Ser Tyr Val Phe Gly Gly Arg Thr Lys Leu Thr Val Leu
        115                 120                 125

Gly Gln
    130

<210> SEQ ID NO 123
<211> LENGTH: 237
<212> TYPE: PRT
<213> ORGANISM: Homo sapiens

<400> SEQUENCE: 123

Met Ser Val Leu Thr Gln Val Leu Ala Leu Leu Leu Leu Trp Leu Thr
1               5                   10                  15

Gly Thr Arg Cys Asp Ile Ala Leu Thr Gln Pro Ala Ser Val Ser Gly
            20                  25                  30

Ser Pro Gly Gln Ser Ile Thr Ile Ser Cys Thr Gly Thr Ser Ser Asp
        35                  40                  45

Val Gly Asp Ile Asn Asp Val Ser Trp Tyr Gln Gln His Pro Gly Lys
    50                  55                  60

Ala Pro Lys Leu Met Ile Tyr Asp Val Asn Asn Arg Pro Ser Gly Val
65                  70                  75                  80

Ser Asn Arg Phe Ser Gly Ser Lys Ser Gly Asn Thr Ala Ser Leu Thr
                85                  90                  95

Ile Ser Gly Leu Gln Ala Glu Asp Glu Ala Asp Tyr Tyr Cys Ser Ser
            100                 105                 110

Tyr Gly Glu Ser Leu Thr Ser Tyr Val Phe Gly Gly Thr Lys Leu
        115                 120                 125

Thr Val Leu Gly Gln Pro Lys Ala Ala Pro Ser Val Thr Leu Phe Pro
    130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
            180                 185                 190

Ser Asn Asn Lys Tyr Ala Ala Ser Ser Tyr Leu Ser Leu Thr Pro Glu
        195                 200                 205

Gln Trp Lys Ser His Arg Ser Tyr Ser Cys Gln Val Thr His Glu Gly
    210                 215                 220

Ser Thr Val Glu Lys Thr Val Ala Pro Thr Glu Cys Ser
225                 230                 235

<210> SEQ ID NO 124
<211> LENGTH: 234
<212> TYPE: PRT
<213> ORGANISM: Homo sapiens

<400> SEQUENCE: 124

Met Ser Val Leu Thr Gln Val Leu Ala Leu Leu Leu Trp Leu Thr
1               5                   10                  15

Gly Thr Arg Cys Asp Ile Glu Leu Thr Gln Pro Pro Ser Val Ser Val
                20                  25                  30

Ala Pro Gly Gln Thr Ala Arg Ile Ser Cys Ser Gly Asp Asn Ile Gly
                35                  40                  45

Ser Phe Tyr Val His Trp Tyr Gln Gln Lys Pro Gly Gln Ala Pro Val
    50                  55                  60

Leu Val Ile Tyr Asp Asp Asn Asn Arg Pro Ser Gly Ile Pro Glu Arg
65                  70                  75                  80

Phe Ser Gly Ser Asn Ser Gly Asn Thr Ala Thr Leu Thr Ile Ser Gly
                85                  90                  95

Thr Gln Ala Glu Asp Glu Ala Asp Tyr Tyr Cys Ala Ser Trp Thr Gly
                100                 105                 110

Val Glu Pro Asp Tyr Val Phe Gly Gly Gly Thr Lys Leu Thr Val Leu
                115                 120                 125

Gly Gln Pro Lys Ala Ala Pro Ser Val Thr Leu Phe Pro Pro Ser Ser
130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
                180                 185                 190

Lys Tyr Ala Ala Ser Ser Tyr Leu Ser Leu Thr Pro Glu Gln Trp Lys
                195                 200                 205

Ser His Arg Ser Tyr Ser Cys Gln Val Thr His Glu Gly Ser Thr Val
                210                 215                 220

Glu Lys Thr Val Ala Pro Thr Glu Cys Ser
225                 230

<210> SEQ ID NO 125
<211> LENGTH: 237
<212> TYPE: PRT
<213> ORGANISM: Homo sapiens

<400> SEQUENCE: 125

Met Ser Val Leu Thr Gln Val Leu Ala Leu Leu Leu Trp Leu Thr
1               5                   10                  15

Gly Thr Arg Cys Asp Ile Ala Leu Thr Gln Pro Ala Ser Val Ser Gly
                20                  25                  30

Ser Pro Gly Gln Ser Ile Thr Ile Ser Cys Thr Gly Thr Ser Ser Asp
                35                  40                  45

Val Gly Asp Ile Asn Asp Val Ser Trp Tyr Gln Gln His Pro Gly Lys
    50                  55                  60

Ala Pro Lys Leu Met Ile Tyr Asp Val Asn Asn Arg Pro Ser Gly Val
65                  70                  75                  80

Ser Asn Arg Phe Ser Gly Ser Lys Ser Gly Asn Thr Ala Ser Leu Thr
                85                  90                  95

Ile Ser Gly Leu Gln Ala Glu Asp Glu Ala Asp Tyr Tyr Cys Gln Ser

```
              100                 105                 110
Tyr Ala Gly Ser Tyr Leu Ser Glu Val Phe Gly Gly Thr Lys Leu
            115                 120                 125
Thr Val Leu Gly Gln Pro Lys Ala Ala Pro Ser Val Thr Leu Phe Pro
130                 135                 140
Pro Ser Ser Glu Glu Leu Gln Ala Asn Lys Ala Thr Leu Val Cys Leu
145                 150                 155                 160
Ile Ser Asp Phe Tyr Pro Gly Ala Val Thr Val Ala Trp Lys Ala Asp
                165                 170                 175
Ser Ser Pro Val Lys Ala Gly Val Glu Thr Thr Thr Pro Ser Lys Gln
            180                 185                 190
Ser Asn Asn Lys Tyr Ala Ala Ser Ser Tyr Leu Ser Leu Thr Pro Glu
            195                 200                 205
Gln Trp Lys Ser His Arg Ser Tyr Ser Cys Gln Val Thr His Glu Gly
            210                 215                 220
Ser Thr Val Glu Lys Thr Val Ala Pro Thr Glu Cys Ser
225                 230                 235

<210> SEQ ID NO 126
<211> LENGTH: 237
<212> TYPE: PRT
<213> ORGANISM: Homo sapiens

<400> SEQUENCE: 126

Met Ser Val Leu Thr Gln Val Leu Ala Leu Leu Leu Trp Leu Thr
1               5                   10                  15
Gly Thr Arg Cys Asp Ile Ala Leu Thr Gln Pro Ala Ser Val Ser Gly
            20                  25                  30
Ser Pro Gly Gln Ser Ile Thr Ile Ser Cys Thr Gly Thr Ser Ser Asp
            35                  40                  45
Val Gly Asp Ile Asn Asp Val Ser Trp Tyr Gln Gln His Pro Gly Lys
        50                  55                  60
Ala Pro Lys Leu Met Ile Tyr Asp Val Asn Asn Arg Pro Ser Gly Val
65                  70                  75                  80
Ser Asn Arg Phe Ser Gly Ser Lys Ser Gly Asn Thr Ala Ser Leu Thr
                85                  90                  95
Ile Ser Gly Leu Gln Ala Glu Asp Glu Ala Asp Tyr Tyr Cys Ser Ser
            100                 105                 110
Tyr Gly Glu Ser Leu Thr Ser Tyr Val Phe Gly Gly Thr Lys Leu
            115                 120                 125
Thr Val Leu Gly Gln Pro Lys Ala Ala Pro Ser Val Thr Leu Phe Pro
130                 135                 140
Pro Ser Ser Glu Glu Leu Gln Ala Asn Lys Ala Thr Leu Val Cys Leu
145                 150                 155                 160
Ile Ser Asp Phe Tyr Pro Gly Ala Val Thr Val Ala Trp Lys Ala Asp
                165                 170                 175
Ser Ser Pro Val Lys Ala Gly Val Glu Thr Thr Thr Pro Ser Lys Gln
            180                 185                 190
Ser Asn Asn Lys Tyr Ala Ala Ser Ser Tyr Leu Ser Leu Thr Pro Glu
            195                 200                 205
Gln Trp Lys Ser His Arg Ser Tyr Ser Cys Gln Val Thr His Glu Gly
            210                 215                 220
Ser Thr Val Glu Lys Thr Val Ala Pro Thr Glu Cys Ser
225                 230                 235
```

<210> SEQ ID NO 127
<211> LENGTH: 237
<212> TYPE: PRT
<213> ORGANISM: Homo sapiens

<400> SEQUENCE: 127

```
Met Ser Val Leu Thr Gln Val Leu Ala Leu Leu Leu Trp Leu Thr
1               5                   10                  15

Gly Thr Arg Cys Asp Ile Ala Leu Thr Gln Pro Ala Ser Val Ser Gly
            20                  25                  30

Ser Pro Gly Gln Ser Ile Thr Ile Ser Cys Thr Gly Thr Ser Ser Asp
        35                  40                  45

Val Gly Asp Ile Asn Asp Val Ser Trp Tyr Gln Gln His Pro Gly Lys
50                  55                  60

Ala Pro Lys Leu Met Ile Tyr Asp Val Asn Asn Arg Pro Ser Gly Val
65                  70                  75                  80

Ser Asn Arg Phe Ser Gly Ser Lys Ser Gly Asn Thr Ala Ser Leu Thr
                85                  90                  95

Ile Ser Gly Leu Gln Ala Glu Asp Glu Ala Asp Tyr Tyr Cys Ser Ser
            100                 105                 110

Tyr Gly Glu Ser Leu Thr Ser Tyr Val Phe Gly Gly Gly Thr Lys Leu
        115                 120                 125

Thr Val Leu Gly Gln Pro Lys Ala Ala Pro Ser Val Thr Leu Phe Pro
130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
            180                 185                 190

Ser Asn Asn Lys Tyr Ala Ala Ser Ser Tyr Leu Ser Leu Thr Pro Glu
        195                 200                 205

Gln Trp Lys Ser His Arg Ser Tyr Ser Cys Gln Val Thr His Glu Gly
    210                 215                 220

Ser Thr Val Glu Lys Thr Val Ala Pro Thr Glu Cys Ser
225                 230                 235
```

<210> SEQ ID NO 128
<211> LENGTH: 237
<212> TYPE: PRT
<213> ORGANISM: Homo sapiens

<400> SEQUENCE: 128

```
Met Ser Val Leu Thr Gln Val Leu Ala Leu Leu Leu Trp Leu Thr
1               5                   10                  15

Gly Thr Arg Cys Asp Ile Ala Leu Thr Gln Pro Ala Ser Val Ser Gly
            20                  25                  30

Ser Pro Gly Gln Ser Ile Thr Ile Ser Cys Thr Gly Thr Ser Ser Asp
        35                  40                  45

Val Gly Asp Ile Asn Asp Val Ser Trp Tyr Gln Gln His Pro Gly Lys
50                  55                  60

Ala Pro Lys Leu Met Ile Tyr Asp Val Asn Asn Arg Pro Ser Gly Val
65                  70                  75                  80

Ser Asn Arg Phe Ser Gly Ser Lys Ser Gly Asn Thr Ala Ser Leu Thr
                85                  90                  95
```

```
Ile Ser Gly Leu Gln Ala Glu Asp Glu Ala Asp Tyr Tyr Cys Ser Ser
                100                 105                 110

Tyr Gly Glu Ser Leu Thr Ser Tyr Val Phe Gly Gly Gly Thr Lys Leu
            115                 120                 125

Thr Val Leu Gly Gln Pro Lys Ala Ala Pro Ser Val Thr Leu Phe Pro
        130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
            180                 185                 190

Ser Asn Asn Lys Tyr Ala Ala Ser Ser Tyr Leu Ser Leu Thr Pro Glu
        195                 200                 205

Gln Trp Lys Ser His Arg Ser Tyr Ser Cys Gln Val Thr His Glu Gly
    210                 215                 220

Ser Thr Val Glu Lys Thr Val Ala Pro Thr Glu Cys Ser
225                 230                 235

<210> SEQ ID NO 129
<211> LENGTH: 237
<212> TYPE: PRT
<213> ORGANISM: Homo sapiens

<400> SEQUENCE: 129

Met Ser Val Leu Thr Gln Val Leu Ala Leu Leu Leu Leu Trp Leu Thr
1               5                   10                  15

Gly Thr Arg Cys Asp Ile Ala Leu Thr Gln Pro Ala Ser Val Ser Gly
            20                  25                  30

Ser Pro Gly Gln Ser Ile Thr Ile Ser Cys Thr Gly Thr Ser Ser Asp
        35                  40                  45

Val Gly Asp Ile Asn Asp Val Ser Trp Tyr Gln Gln His Pro Gly Lys
    50                  55                  60

Ala Pro Lys Leu Met Ile Tyr Asp Val Asn Asn Arg Pro Ser Gly Val
65                  70                  75                  80

Ser Asn Arg Phe Ser Gly Ser Lys Ser Gly Asn Thr Ala Ser Leu Thr
                85                  90                  95

Ile Ser Gly Leu Gln Ala Glu Asp Glu Ala Asp Tyr Tyr Cys Ser Ser
                100                 105                 110

Tyr Gly Glu Ser Leu Thr Ser Tyr Val Phe Gly Gly Gly Thr Lys Leu
            115                 120                 125

Thr Val Leu Gly Gln Pro Lys Ala Ala Pro Ser Val Thr Leu Phe Pro
        130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
            180                 185                 190

Ser Asn Asn Lys Tyr Ala Ala Ser Ser Tyr Leu Ser Leu Thr Pro Glu
        195                 200                 205

Gln Trp Lys Ser His Arg Ser Tyr Ser Cys Gln Val Thr His Glu Gly
    210                 215                 220

Ser Thr Val Glu Lys Thr Val Ala Pro Thr Glu Cys Ser
225                 230                 235
```

<210> SEQ ID NO 130
<211> LENGTH: 237
<212> TYPE: PRT
<213> ORGANISM: Homo sapiens

<400> SEQUENCE: 130

Met Ser Val Leu Thr Gln Val Leu Ala Leu Leu Leu Trp Leu Thr
1               5                   10                  15

Gly Thr Arg Cys Asp Ile Ala Leu Thr Gln Pro Ala Ser Val Ser Gly
            20                  25                  30

Ser Pro Gly Gln Ser Ile Thr Ile Ser Cys Thr Gly Thr Ser Ser Asp
            35                  40                  45

Val Gly Asp Ile Asn Asp Val Ser Trp Tyr Gln Gln His Pro Gly Lys
50                  55                  60

Ala Pro Lys Leu Met Ile Tyr Asp Val Asn Asn Arg Pro Ser Gly Val
65                  70                  75                  80

Ser Asn Arg Phe Ser Gly Ser Lys Ser Gly Asn Thr Ala Ser Leu Thr
                85                  90                  95

Ile Ser Gly Leu Gln Ala Glu Asp Glu Ala Asp Tyr Tyr Cys Ser Thr
            100                 105                 110

Tyr Asp Gly Pro Gly Leu Ser Glu Val Phe Gly Gly Thr Lys Leu
            115                 120                 125

Thr Val Leu Gly Gln Pro Lys Ala Ala Pro Ser Val Thr Leu Phe Pro
130                 135                 140

Pro Ser Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
            180                 185                 190

Ser Asn Asn Lys Tyr Ala Ala Ser Ser Tyr Leu Ser Leu Thr Pro Glu
            195                 200                 205

Gln Trp Lys Ser His Arg Ser Tyr Ser Cys Gln Val Thr His Glu Gly
210                 215                 220

Ser Thr Val Glu Lys Thr Val Ala Pro Thr Glu Cys Ser
225                 230                 235

<210> SEQ ID NO 131
<211> LENGTH: 237
<212> TYPE: PRT
<213> ORGANISM: Homo sapiens

<400> SEQUENCE: 131

Met Ser Val Leu Thr Gln Val Leu Ala Leu Leu Leu Trp Leu Thr
1               5                   10                  15

Gly Thr Arg Cys Asp Ile Ala Leu Thr Gln Pro Ala Ser Val Ser Gly
            20                  25                  30

Ser Pro Gly Gln Ser Ile Thr Ile Ser Cys Thr Gly Thr Ser Ser Asp
            35                  40                  45

Val Gly Asp Ile Asn Asp Val Ser Trp Tyr Gln Gln His Pro Gly Lys
50                  55                  60

Ala Pro Lys Leu Met Ile Tyr Asp Val Asn Asn Arg Pro Ser Gly Val
65                  70                  75                  80

Ser Asn Arg Phe Ser Gly Ser Lys Ser Gly Asn Thr Ala Ser Leu Thr
                85                  90                  95

```
Ile Ser Gly Leu Gln Ala Glu Asp Glu Ala Asp Tyr Tyr Cys Ser Ser
                100                 105                 110

Tyr Gly Glu Ser Leu Thr Ser Tyr Val Phe Gly Gly Gly Thr Lys Leu
            115                 120                 125

Thr Val Leu Gly Gln Pro Lys Ala Ala Pro Ser Val Thr Leu Phe Pro
        130                 135                 140

Pro Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
            180                 185                 190

Ser Asn Asn Lys Tyr Ala Ala Ser Ser Tyr Leu Ser Leu Thr Pro Glu
        195                 200                 205

Gln Trp Lys Ser His Arg Ser Tyr Ser Cys Gln Val Thr His Glu Gly
    210                 215                 220

Ser Thr Val Glu Lys Thr Val Ala Pro Thr Glu Cys Ser
225                 230                 235

<210> SEQ ID NO 132
<211> LENGTH: 237
<212> TYPE: PRT
<213> ORGANISM: Homo sapiens

<400> SEQUENCE: 132

Met Ser Val Leu Thr Gln Val Leu Ala Leu Leu Leu Leu Trp Leu Thr
1               5                   10                  15

Gly Thr Arg Cys Asp Ile Ala Leu Thr Gln Pro Ala Ser Val Ser Gly
            20                  25                  30

Ser Pro Gly Gln Ser Ile Thr Ile Ser Cys Thr Gly Thr Ser Ser Asp
        35                  40                  45

Val Gly Asp Ile Asn Asp Val Ser Trp Tyr Gln Gln His Pro Gly Lys
    50                  55                  60

Ala Pro Lys Leu Met Ile Tyr Asp Val Asn Asn Arg Pro Ser Gly Val
65                  70                  75                  80

Ser Asn Arg Phe Ser Gly Ser Lys Ser Gly Asn Thr Ala Ser Leu Thr
                85                  90                  95

Ile Ser Gly Leu Gln Ala Glu Asp Glu Ala Asp Tyr Tyr Cys Ser Thr
            100                 105                 110

Tyr Asp Gly Pro Gly Leu Ser Glu Val Phe Gly Gly Gly Thr Lys Leu
        115                 120                 125

Thr Val Leu Gly Gln Pro Lys Ala Ala Pro Ser Val Thr Leu Phe Pro
    130                 135                 140

Pro Ser Glu Glu Leu Gln Ala Asn Lys Ala Thr Leu Val Cys Leu
145                 150                 155                 160

Ile Ser Asp Phe Tyr Pro Gly Ala Val Thr Val Ala Trp Lys Ala Asp
                165                 170                 175

Ser Ser Pro Val Lys Ala Gly Val Glu Thr Thr Thr Pro Ser Lys Gln
            180                 185                 190

Ser Asn Asn Lys Tyr Ala Ala Ser Ser Tyr Leu Ser Leu Thr Pro Glu
        195                 200                 205

Gln Trp Lys Ser His Arg Ser Tyr Ser Cys Gln Val Thr His Glu Gly
    210                 215                 220

Ser Thr Val Glu Lys Thr Val Ala Pro Thr Glu Cys Ser
```

<210> SEQ ID NO 133
<211> LENGTH: 1410
<212> TYPE: DNA
<213> ORGANISM: Homo sapiens

<400> SEQUENCE: 133

| | | | | | |
|---|---|---|---|---|---|
| atggcttggg | tgtggacctt | gccattcctg | atggcagctg | cccaaagcgt | gcaggcccag | 60 |
| gtgcagctgg | tcgagtctgg | cggcggactg | gtgcagcctg | gcggcagcct | gagactgagc | 120 |
| tgcgccgcca | gcggcttcac | cttcagcagc | tacgtgatga | ctgggtgcg | gcaggcccct | 180 |
| ggcaagggcc | tggagtgggt | gtccttcatc | agcggcgaca | gcagcaacac | ctactacgcc | 240 |
| gacagcgtga | agggccggtt | caccatcagc | cgggacaaca | gcaagaacac | cctgtacctg | 300 |
| cagatgaaca | gcctgcgggc | cgaggacacc | gccgtgtact | actgcgcccg | gaccttcatg | 360 |
| cacggccacc | tgggcggagg | actgagcatg | gatttctggg | gccagggcac | cctggtcacc | 420 |
| gtctcctcag | cttccaccaa | gggcccatcc | gtcttccccc | tggcgccctg | ctccaggagc | 480 |
| acctccgaga | gcacagcggc | cctgggctgc | ctggtcaagg | actacttccc | cgaaccggtg | 540 |
| acggtgtcgt | ggaactcagg | cgctctgacc | agcggcgtgc | acaccttccc | agctgtccta | 600 |
| cagtcctcag | gactctactc | cctcagcagc | gtggtgacag | tgccctccag | caacttcggc | 660 |
| acccagacct | acacctgcaa | cgtagatcac | aagcccagca | acaccaaggt | ggacaagaca | 720 |
| gttgagcgca | aatgttgtgt | cgagtgccca | ccgtgcccag | caccacctgt | ggcaggaccg | 780 |
| tcagtcttcc | tcttcccccc | aaaacccaag | gacaccctca | tgatctcccg | gacccctgag | 840 |
| gtcacgtgcg | tggtggtgga | cgtgagccac | gaagacccg | aggtccagtt | caactggtac | 900 |
| gtggacggcg | tggaggtgca | taatgccaag | acaaagccac | gggaggagca | gttcaacagc | 960 |
| acgttccgtg | tggtcagcgt | cctcaccgtt | gtgcaccagg | actggctgaa | cggcaaggag | 1020 |
| tacaagtgca | aggtctccaa | caaaggcctc | ccagccccca | tcgagaaaac | catctccaaa | 1080 |
| accaaagggc | agccccgaga | accacaggtg | tacaccctgc | ccccatcccg | ggaggagatg | 1140 |
| accaagaacc | aggtcagcct | gacctgcctg | gtcaaaggct | tctaccccag | cgacatcgcc | 1200 |
| gtggagtggg | agagcaatgg | gcagccggag | aacaactaca | agaccacacc | tcccatgctg | 1260 |
| gactccgacg | gctccttctt | cctctacagc | aagctcaccg | tggacaagag | caggtggcag | 1320 |
| caggggaacg | tcttctcatg | ctccgtgatg | catgaggctc | tgcacaacca | ctacacgcag | 1380 |
| aagagcctct | ccctgtctcc | gggtaaatga | | | | 1410 |

<210> SEQ ID NO 134
<211> LENGTH: 1389
<212> TYPE: DNA
<213> ORGANISM: Homo sapiens

<400> SEQUENCE: 134

| | | | | | |
|---|---|---|---|---|---|
| atggcttggg | tgtggacctt | gccattcctg | atggcagctg | cccaaggtgt | ccaggcccag | 60 |
| gtgcagctgg | tcgagagcgg | cggagggctg | gtgcagcctg | gcggcagcct | gagactgagc | 120 |
| tgcgccgcca | gcggcttcac | cttcagaagc | cactggctgt | cctgggtgcg | gcaggcccct | 180 |
| ggcaagggcc | tggaatgggt | gtccaacatc | aactacgacg | gcagcagcac | ctactacgcc | 240 |
| gacagcgtga | agggccggtt | caccatcagc | cgggacaaca | gcaagaacac | cctgtacctg | 300 |
| cagatgaaca | gcctgcgggc | cgaggacacc | gccgtgtact | actgcgccag | ggacacctac | 360 |
| ctgcacttcg | actactgggg | ccagggcacc | ctggtcaccg | tctcctcagc | ttccaccaag | 420 |

```
ggcccatccg tcttcccct ggcgccctgc tccaggagca cctccgagag cacagcggcc      480
ctgggctgcc tggtcaagga ctacttcccc gaaccggtga cggtgtcgtg gaactcaggc      540
gctctgacca gcggcgtgca caccttccca gctgtcctac agtcctcagg actctactcc      600
ctcagcagcg tggtgacagt gccctccagc aacttcggca cccagaccta cacctgcaac      660
gtagatcaca agcccagcaa caccaaggtg gacaagacag ttgagcgcaa atgttgtgtc      720
gagtgcccac cgtgcccagc accacctgtg gcaggaccgt cagtcttcct cttccccca      780 aaacccaagg acaccctcat gatctcccgg acccctgagg tcacgtgcgt ggtggtggac      840
gtgagccacg aagaccccga ggtccagttc aactggtacg tggacggcgt ggaggtgcat      900
aatgccaaga caaagccacg ggaggagcag ttcaacagca cgttccgtgt ggtcagcgtc      960
ctcaccgttg tgcaccagga ctggctgaac ggcaaggagt acaagtgcaa ggtctccaac     1020
aaaggcctcc cagcccccat cgagaaaacc atctccaaaa ccaaagggca gccccgagaa     1080
ccacaggtgt acaccctgcc cccatcccgg gaggagatga ccaagaacca ggtcagcctg     1140
acctgcctgg tcaaaggctt ctaccccagc gacatcgccg tggagtggga gagcaatggg     1200
cagccggaga caactacaa gaccacacct cccatgctgg actccgacgg ctccttcttc     1260
ctctacagca agctcaccgt ggacaagagc aggtggcagc aggggaacgt cttctcatgc     1320
tccgtgatgc atgaggctct gcacaaccac tacacgcaga gagcctctc cctgtctccg     1380 ggtaaatga                                                              1389

<210> SEQ ID NO 135
<211> LENGTH: 1410
<212> TYPE: DNA
<213> ORGANISM: Homo sapiens

<400> SEQUENCE: 135
atggcttggg tgtggacctt gccattcctg atggcagctg cccaaagcgt gcaggcccag       60
gtgcagctgg tcgagtctgg cggcggactg gtgcagcctg gcggcagcct gagactgagc      120
tgcgccgcca gcggcttcac cttcagcagc tacgtgatga actgggtgcg gcaggccct      180 ggcaagggcc tggagtgggt gtccttcatc agcggcgaca gcagcaacac ctactacgcc      240
gacagcgtga agggccggtt caccatcagc cgggacaaca gcaagaacac cctgtacctg      300
cagatgaaca gcctgcgggc cgaggacacc gccgtgtact actgcgcccg gaccttcatg      360
cacggccacc tggcggagg actgagcatg gatttctggg gccagggcac cctggtcacc      420
gtctcctcag cttccaccaa gggcccatcc gtcttccccc tggcgccctg ctccaggagc      480
acctccgaga gcacagcggc cctgggctgc ctggtcaagg actacttccc gaaccggtg      540 acggtgtcgt ggaactcagg cgctctgacc agcggcgtgc acaccttccc agctgtccta     600
cagtcctcag gactctactc cctcagcagc gtggtgacag tgccctccag caacttcggc      660
acccagacct acacctgcaa cgtagatcac aagcccagca acaccaaggt ggacaagaca      720
gttgagcgca atgttgtgt cgagtgccca ccgtgcccag caccacctgt ggcaggaccg      780
tcagtcttcc tcttccccc aaaacccaag gacaccctca tgatctcccg gacccctgag      840
gtcacgtgcg tggtggtgga cgtgagccac gaagaccccg aggtccagtt caactggtac      900
gtggacggcg tggaggtgca ataatgccaag acaaagccac gggaggagca gttcaacagc      960
acgttccgtg tggtcagcgt cctcaccgtt gtgcaccagg actggctgaa cggcaaggag     1020
tacaagtgca aggtctccaa caaaggcctc ccagcccca tcgagaaaac catctccaaa     1080
```

| | |
|---|---|
| accaaagggc agccccgaga accacaggtg tacaccctgc ccccatcccg ggaggagatg | 1140 |
| accaagaacc aggtcagcct gacctgcctg gtcaaaggct tctacccag cgacatcgcc | 1200 |
| gtggagtggg agagcaatgg gcagccggag aacaactaca agaccacacc tcccatgctg | 1260 |
| gactccgacg gctccttctt cctctacagc aagctcaccg tggacaagag caggtggcag | 1320 |
| caggggaacg tcttctcatg ctccgtgatg catgaggctc tgcacaacca ctacacgcag | 1380 |
| aagagcctct ccctgtctcc gggtaaatga | 1410 |

<210> SEQ ID NO 136
<211> LENGTH: 1389
<212> TYPE: DNA
<213> ORGANISM: Homo sapiens

<400> SEQUENCE: 136

| | |
|---|---|
| atggcttggg tgtggacctt gccattcctg atggcagctg cccaaggtgt ccaggcccag | 60 |
| gtgcagctgg tcgagagcgg cggagggctg gtgcagcctg gcggcagcct gagactgagc | 120 |
| tgcgccgcca gcggcttcac cttcagaagc cactggctgt cctgggtgcg gcaggcccct | 180 |
| ggcaagggcc tggaatgggt gtccaacatc aactacgacg gcagcagcac ctactacgcc | 240 |
| gacagcgtga agggccggtt caccatcagc cgggacaaca gcaagaacac cctgtacctg | 300 |
| cagatgaaca gcctgcgggc cgaggacacc gccgtgtact actgcgccag ggacacctac | 360 |
| ctgcacttcg actactgggg ccagggcacc ctggtcaccg tctcctcagc ttccaccaag | 420 |
| ggcccatccg tcttccccct ggcgccctgc tccaggagca cctccgagag cacagcggcc | 480 |
| ctgggctgcc tggtcaagga ctacttcccc gaaccggtga cggtgtcgtg gaactcaggc | 540 |
| gctctgacca gcggcgtgca caccttccca gctgtcctac agtcctcagg actctactcc | 600 |
| ctcagcagcg tggtgacagt gccctccagc aacttcggca cccagaccta cacctgcaac | 660 |
| gtagatcaca agcccagcaa caccaaggtg gacaagacag ttgagcgcaa atgttgtgtc | 720 |
| gagtgcccac cgtgcccagc accacctgtg gcaggaccgt cagtcttcct cttcccccca | 780 |
| aaacccaagg acaccctcat gatctcccgg acccctgagg tcacgtgcgt ggtggtggac | 840 |
| gtgagccacg aagaccccga ggtccagttc aactggtacg tggacggcgt ggaggtgcat | 900 |
| aatgccaaga caaagccacg ggaggagcag ttcaacagca cgttccgtgt ggtcagcgtc | 960 |
| ctcaccgttg tgcaccagga ctggctgaac ggcaaggagt acaagtgcaa ggtctccaac | 1020 |
| aaaggcctcc cagcccccat cgagaaaacc atctccaaaa ccaaagggca gccccgagaa | 1080 |
| ccacaggtgt acaccctgcc cccatcccgg gaggagatga ccaagaacca ggtcagcctg | 1140 |
| acctgcctgg tcaaaggctt ctaccccagc gacatcgccg tggagtggga gagcaatggg | 1200 |
| cagccggaga acaactacaa gaccacacct cccatgctgg actccgacgg ctccttcttc | 1260 |
| ctctacagca agctcaccgt ggacaagagc aggtggcagc aggggaacgt cttctcatgc | 1320 |
| tccgtgatgc atgaggctct gcacaaccac tacacgcaga agagcctctc cctgtctccg | 1380 |
| ggtaaatga | 1389 |

<210> SEQ ID NO 137
<211> LENGTH: 1386
<212> TYPE: DNA
<213> ORGANISM: Homo sapiens

<400> SEQUENCE: 137

| | |
|---|---|
| atggcttggg tgtggacctt gccattcctg atggcagctg cccaaagtgt ccaggcccag | 60 |
| gtgcagctgg tcgagagcgg cggagggctg gtgcagcctg gcggcagcct gagactgagc | 120 |

```
tgcgccgcca gcggcttcac cttcagaagc cactggctgt cctgggtgcg gcaggcccct    180
ggcaagggcc tggaatgggt gtccgtgacc ggcgtgcacg gcgacaccta ctacgccgac    240
agcgtgaagg gccggttcac catcagccgg gacaacagca gaacaccct gtacctgcag     300 atgaacagct gcgggccga ggacaccgcc gtgtactact gcgccaggga cacctacctg     360
cacttcgact actggggcca gggcaccctg gtcaccgtct cctcagcttc accaagggc     420 ccatccgtct tccccctggc gccctgctcc aggagcacct ccgagagcac agcggccctg    480
ggctgcctgg tcaaggacta cttccccgaa ccggtgacgg tgtcgtggaa ctcaggcgct    540
ctgaccagcg gcgtgcacac cttcccagct gtcctacagt cctcaggact ctactccctc    600
agcagcgtgg tgacagtgcc ctccagcaac ttcggcaccc agacctacac ctgcaacgta    660
gatcacaagc ccagcaacac caaggtggac aagacagttg agcgcaaatg ttgtgtcgag    720
tgcccaccgt gcccagcacc acctgtggca ggaccgtcag tcttcctctt ccccccaaaa    780
cccaaggaca ccctcatgat ctcccggacc cctgaggtca cgtgcgtggt ggtggacgtg    840
agccacgaag accccgaggt ccagttcaac tggtacgtgg acggcgtgga ggtgcataat    900
gccaagacaa agccacggga ggagcagttc aacagcacgt tccgtgtggt cagcgtcctc    960
accgttgtgc accaggactg gctgaacggc aaggagtaca agtgcaaggt ctccaacaaa   1020
ggcctcccag cccccatcga gaaaaccatc tccaaaacca agggcagcc ccgagaacca    1080 caggtgtaca ccctgccccc atcccgggag gagatgacca agaaccaggt cagcctgacc   1140
tgcctggtca aaggcttcta ccccagcgac atcgccgtgg agtgggagag caatgggcag   1200
ccggagaaca actacaagac cacacctccc atgctggact ccgacggctc cttcttcctc   1260
tacagcaagc tcaccgtgga caagagcagg tggcagcagg ggaacgtctt ctcatgctcc   1320
gtgatgcatg aggctctgca caaccactac acgcagaaga gcctctccct gtctccgggt   1380
aaatga                                                              1386
```

<210> SEQ ID NO 138
<211> LENGTH: 1386
<212> TYPE: DNA
<213> ORGANISM: Homo sapiens

<400> SEQUENCE: 138

```
atggcttggg tgtggacctt gccattcctg atggcagctg cccaaagtgt ccaggcccag     60
gtgcagctgg tcgagagcgg cggagggctg gtgcagcctg gcggcagcct gagactgagc    120
tgcgccgcca gcggcttcac cttcagaagc cactggctgt cctgggtgcg gcaggcccct    180
ggcaagggcc tggaatgggt gtccgtgatc ggcaactggg gcgacaccta ctacgccgac    240
agcgtgaagg gccggttcac catcagccgg gacaacagca gaacaccct gtacctgcag     300 atgaacagcc tgcgggccga ggacaccgcc gtgtactact gcgccaggga cacctacctg    360
cacttcgact actggggcca gggcaccctg gtcaccgtct cctcagcttc accaagggc     420 ccatccgtct tccccctggc gccctgctcc aggagcacct ccgagagcac agcggccctg    480
ggctgcctgg tcaaggacta cttccccgaa ccggtgacgg tgtcgtggaa ctcaggcgct    540
ctgaccagcg gcgtgcacac cttcccagct gtcctacagt cctcaggact ctactccctc    600
agcagcgtgg tgacagtgcc ctccagcaac ttcggcaccc agacctacac ctgcaacgta    660
gatcacaagc ccagcaacac caaggtggac aagacagttg agcgcaaatg ttgtgtcgag    720
tgcccaccgt gcccagcacc acctgtggca ggaccgtcag tcttcctctt ccccccaaaa    780
```

```
cccaaggaca ccctcatgat ctcccggacc cctgaggtca cgtgcgtggt ggtggacgtg      840
agccacgaag accccgaggt ccagttcaac tggtacgtgg acggcgtgga ggtgcataat      900
gccaagacaa agccacggga ggagcagttc aacagcacgt tccgtgtggt cagcgtcctc      960
accgttgtgc accaggactg gctgaacggc aaggagtaca agtgcaaggt ctccaacaaa     1020
ggcctcccag cccccatcga aaaaccatc tccaaaacca agggcagcc ccgagaacca      1080 caggtgtaca ccctgccccc atcccgggag gagatgacca agaaccaggt cagcctgacc     1140
tgcctggtca aaggcttcta ccccagcgac atcgccgtgg agtgggagag caatgggcag     1200
ccggagaaca actacaagac cacacctccc atgctggact ccgacggctc cttcttcctc     1260
tacagcaagc tcaccgtgga caagagcagg tggcagcagg ggaacgtctt ctcatgctcc     1320
gtgatgcatg aggctctgca caaccactac acgcagaaga gcctctccct gtctccgggt     1380
aaatga                                                                1386

<210> SEQ ID NO 139
<211> LENGTH: 1386
<212> TYPE: DNA
<213> ORGANISM: Homo sapiens

<400> SEQUENCE: 139
atggcttggg tgtggacctt gccattcctg atggcagctg cccaaagtgt ccaggcccag       60
gtgcagctgg tcgagagcgg cggagggctg gtgcagcctg gcggcagcct gagactgagc      120
tgcgccgcca gcggcttcac cttcagaagc cactggctgt cctgggtgcg gcaggcccct      180
ggcaagggcc tggaatgggt gtccgtgacc acccaccagg gctacaccta ctacgccgac      240
agcgtgaagg gccggttcac catcagccgg gacaacagca gaacaccct gtacctgcag      300 atgaacagcc tgcgggccga ggacaccgcc gtgtactact gcgccaggga cacctacctg      360
cacttcgact actggggcca gggcaccctg gtcaccgtct cctcagcttc caccaagggc      420
ccatccgtct tccccctggc gccctgctcc aggagcacct ccgagagcac agcggccctg      480
ggctgcctgg tcaaggacta cttccccgaa ccggtgacgg tgtcgtggaa ctcaggcgct      540
ctgaccagcg gcgtgcacac cttcccagct gtcctacagt cctcaggact ctactccctc      600
agcagcgtgg tgacagtgcc ctccagcaac ttcggcaccc agacctacac ctgcaacgta      660
gatcacaagc ccagcaacac caaggtggac aagacagttg agcgcaaatg ttgtgtcgag      720
tgcccaccgt gcccagcacc acctgtggca ggaccgtcag tcttcctctt ccccccaaaa      780
cccaaggaca ccctcatgat ctcccggacc cctgaggtca cgtgcgtggt ggtggacgtg      840
agccacgaag accccgaggt ccagttcaac tggtacgtgg acggcgtgga ggtgcataat      900
gccaagacaa agccacggga ggagcagttc aacagcacgt tccgtgtggt cagcgtcctc      960
accgttgtgc accaggactg gctgaacggc aaggagtaca agtgcaaggt ctccaacaaa     1020
ggcctcccag cccccatcga aaaaccatc tccaaaacca agggcagcc ccgagaacca      1080 caggtgtaca ccctgccccc atcccgggag gagatgacca agaaccaggt cagcctgacc     1140
tgcctggtca aaggcttcta ccccagcgac atcgccgtgg agtgggagag caatgggcag     1200
ccggagaaca actacaagac cacacctccc atgctggact ccgacggctc cttcttcctc     1260
tacagcaagc tcaccgtgga caagagcagg tggcagcagg ggaacgtctt ctcatgctcc     1320
gtgatgcatg aggctctgca caaccactac acgcagaaga gcctctccct gtctccgggt     1380
aaatga                                                                1386
```

```
<210> SEQ ID NO 140
<211> LENGTH: 1386
<212> TYPE: DNA
<213> ORGANISM: Homo sapiens

<400> SEQUENCE: 140
atggcttggg tgtggacctt gccattcctg atggcagctg cccaaagtgt ccaggcccag     60
gtgcagctgg tcgagagcgg cggagggctg gtgcagcctg gcggcagcct gagactgagc    120
tgcgccgcca gcggcttcac cttcagaagc cactggctgt cctgggtgcg gcaggcccct    180
ggcaagggcc tggaatgggt gtccgccacc aacagatacg gctacaccta ctacgccgac    240
agcgtgaagg gccggttcac catcagccgg gacaacagca gaacacccct gtacctgcag    300
atgaacagcc tgcgggccga ggacaccgcc gtgtactact gcgcaggga cacctacctg    360 cacttcgact actggggcca gggcaccctg gtcaccgtct cctcagcttc caccaagggc    420
ccatccgtct tccccctggc gccctgctcc aggagcacct ccgagagcac agcggccctg    480
ggctgcctgg tcaaggacta cttccccgaa ccggtgacgg tgtcgtggaa ctcaggcgct    540
ctgaccagcg gcgtgcacac cttcccagct gtcctacagt cctcaggact ctactccctc    600
agcagcgtgt gacagtgcc ctccagcaac ttcggcaccc agacctacac ctgcaacgta    660
gatcacaagc ccagcaacac caaggtggac aagacagttg agcgcaaatg ttgtgtcgag    720
tgcccaccgt gcccagcacc acctgtggca ggaccgtcag tcttcctctt ccccccaaaa    780
cccaaggaca cctcatgat ctcccggacc cctgaggtca cgtgcgtggt ggtggacgtg    840
agccacgaag accccgaggt ccagttcaac tggtacgtgg acggcgtgga ggtgcataat    900
gccaagacaa agccacggga ggagcagttc aacagcacgt tccgtgtggt cagcgtcctc    960
accgttgtgc accaggactg gctgaacggc aaggagtaca agtgcaaggt ctccaacaaa   1020
ggcctcccag cccccatcga gaaaaccatc tccaaaacca agggcagcc ccgagaacca   1080 caggtgtaca ccctgccccc atcccgggag gagatgacca agaaccaggt cagcctgacc   1140
tgcctggtca aaggcttcta ccccagcgac atcgccgtgg agtgggagag caatgggcag   1200
ccggagaaca actacaagac cacacctccc atgctggact ccgacggctc cttcttcctc   1260
tacagcaagc tcaccgtgga caagagcagg tggcagcagg gaacgtcttt ctcatgctcc   1320
gtgatgcatg aggctctgca caaccactac acgcagaaga gcctctccct gtctccgggt   1380
aaatga                                                              1386

<210> SEQ ID NO 141
<211> LENGTH: 1389
<212> TYPE: DNA
<213> ORGANISM: Homo sapiens

<400> SEQUENCE: 141
atggcttggg tgtggacctt gccattcctg atggcagctg cccaaggtgt ccaggcccag     60
gtgcagctgg tcgagagcgg cggagggctg gtgcagcctg gcggcagcct gagactgagc    120
tgcgccgcca gcggcttcac cttcagaagc cactggctgt cctgggtgcg gcaggcccct    180
ggcaagggcc tggaatgggt gtccaacatc aactacgacg gcagcagcac ctactacgcc    240
gacagcgtga agggccggtt caccatcagc cgggacaaca gcaagaacac cctgtacctg    300
cagatgaaca gcctgcgggc cgaggacacc gccgtgtact actgcgccag ggacacctac    360
ctgcacttcg actactgggg ccagggcacc ctggtcaccg tctcctcagc ttccaccaag    420
ggcccatccg tcttcccct ggcgccctgc tccaggagca cctccgagag cacagcggcc    480
```

| | |
|---|---|
| ctgggctgcc tggtcaagga ctacttcccc gaaccggtga cggtgtcgtg gaactcaggc | 540 |
| gctctgacca gcggcgtgca caccttccca gctgtcctac agtcctcagg actctactcc | 600 |
| ctcagcagcg tggtgacagt gccctccagc aacttcggca cccagaccta cacctgcaac | 660 |
| gtagatcaca agcccagcaa caccaaggtg gacaagacag ttgagcgcaa atgttgtgtc | 720 |
| gagtgcccac cgtgcccagc accacctgtg gcaggaccgt cagtcttcct cttcccccca | 780 |
| aaacccaagg acaccctcat gatctcccgg acccctgagg tcacgtgcgt ggtggtggac | 840 |
| gtgagccacg aagaccccga ggtccagttc aactggtacg tggacggcgt ggaggtgcat | 900 |
| aatgccaaga caaagccacg gggaggagcag ttcaacagca cgttccgtgt ggtcagcgtc | 960 |
| ctcaccgttg tgcaccagga ctggctgaac ggcaaggagt acaagtgcaa ggtctccaac | 1020 |
| aaaggcctcc cagcccccat cgagaaaacc atctccaaaa ccaaagggca gccccgagaa | 1080 |
| ccacaggtgt acaccctgcc cccatcccgg gaggagatga ccaagaacca ggtcagcctg | 1140 |
| acctgcctgg tcaaaggctt ctaccccagc gacatcgccg tggagtggga gagcaatggg | 1200 |
| cagccggaga acaactacaa gaccacacct cccatgctgg actccgacgg ctccttcttc | 1260 |
| ctctacagca agctcaccgt ggacaagagc aggtggcagc aggggaacgt cttctcatgc | 1320 |
| tccgtgatgc atgaggctct gcacaaccac tacacgcaga agagcctctc cctgtctccg | 1380 |
| ggtaaatga | 1389 |

<210> SEQ ID NO 142
<211> LENGTH: 1386
<212> TYPE: DNA
<213> ORGANISM: Homo sapiens

<400> SEQUENCE: 142

| | |
|---|---|
| atggcttggg tgtggacctt gccattcctg atggcagctg cccaaagtgt ccaggcccag | 60 |
| gtgcagctgg tcgagagcgg cggagggctg gtgcagcctg gcggcagcct gagactgagc | 120 |
| tgcgccgcca gcggcttcac cttcagaagc cactggctgt cctgggtgcg gcaggcccct | 180 |
| ggcaagggcc tggaatgggt gtccgtgatc accccctacg gcgacaccta ctacgccgac | 240 |
| agcgtgaagg gccggttcac catcagccgg gacaacagca gaaccaccct gtacctgcag | 300 |
| atgaacagcc tgcgggccga ggacaccgcc gtgtactact gcgccaggga cacctacctg | 360 |
| cacttcgact actggggcca gggcaccctg gtcaccgtct cctcagcttc caccaagggc | 420 |
| ccatccgtct tccccctggc gccctgctcc aggagcacct ccgagagcac agcggccctg | 480 |
| ggctgcctgg tcaaggacta cttccccgaa ccggtgacgg tgtcgtggaa ctcaggcgct | 540 |
| ctgaccagcg gcgtgcacac cttcccagct gtcctacagt cctcaggact ctactccctc | 600 |
| agcagcgtgg tgacagtgcc ctccagcaac ttcggcaccc agacctacac ctgcaacgta | 660 |
| gatcacaagc ccagcaacac caaggtggac aagacagttg agcgcaaatg ttgtgtcgag | 720 |
| tgcccaccgt gcccagcacc acctgtggca ggaccgtcag tcttcctctt ccccccaaaa | 780 |
| cccaaggaca ccctcatgat ctcccggacc cctgaggtca cgtgcgtggt ggtggacgtg | 840 |
| agccacgaag accccgaggt ccagttcaac tggtacgtgg acggcgtgga ggtgcataat | 900 |
| gccaagacaa agccacggga ggagcagttc aacagcacgt tccgtgtggt cagcgtcctc | 960 |
| accgttgtgc accaggactg gctgaacggc aaggagtaca agtgcaaggt ctccaacaaa | 1020 |
| ggcctcccag cccccatcga gaaaaccatc tccaaaacca agggcagcc cgagaaccac | 1080 |
| caggtgtaca ccctgccccc atcccgggag gagatgacca agaaccaggt cagcctgacc | 1140 |
| tgcctggtca aaggcttcta ccccagcgac atcgccgtgg agtgggagag caatgggcag | 1200 |

```
ccggagaaca actacaagac cacacctccc atgctggact ccgacggctc cttcttcctc    1260
tacagcaagc tcaccgtgga caagagcagg tggcagcagg ggaacgtctt ctcatgctcc    1320
gtgatgcatg aggctctgca caaccactac acgcagaaga gcctctccct gtctccgggt    1380
aaatga                                                              1386

<210> SEQ ID NO 143
<211> LENGTH: 1386
<212> TYPE: DNA
<213> ORGANISM: Homo sapiens

<400> SEQUENCE: 143
atggcttggg tgtggacctt gccattcctg atggcagctg cccaaagtgt ccaggcccag      60
gtgcagctgg tcgagagcgg cggagggctg gtgcagcctg gcggcagcct gagactgagc     120
tgcgccgcca gcggcttcac cttcagaagc cactggctgt cctgggtgcg gcaggcccct     180
ggcaagggcc tggaatgggt gtccgtgatc acccctacg gcgacaccta ctacgccgac      240
agcgtgaagg gccggttcac catcagccgg acaacagca gaacacccct gtacctgcag      300
atgaacagcc tgcgggccga ggacaccgcc gtgtactact gcgccaggga cacctacctg     360
cacttcgact actggggcca gggcaccctg gtcaccgtct cctcagcttc caccaagggc     420
ccatccgtct tccccctggc gccctgctcc aggagcacct ccgagagcac agcggccctg     480
ggctgcctgg tcaaggacta cttccccgaa ccggtgacgg tgtcgtggaa ctcaggcgct     540
ctgaccagcg gcgtgcacac cttcccagct gtcctacagt cctcaggact ctactccctc     600
agcagcgtgg tgacagtgcc ctccagcaac ttcggcaccc agacctacac ctgcaacgta     660
gatcacaagc ccagcaacac caaggtggac aagacagttg agcgcaaatg ttgtgtcgag     720
tgcccaccgt gcccagcacc acctgtggca ggaccgtcag tcttcctctt cccccaaaa     780 cccaaggaca cctctcatgat ctcccggacc cctgaggtca cgtgcgtggt ggtggacgtg    840
agccacgaag accccgaggt ccagttcaac tggtacgtgg acggcgtgga ggtgcataat     900
gccaagacaa agccacggga ggagcagttc aacagcacgt tccgtgtggt cagcgtcctc     960
accgttgtgc accaggactg gctgaacggc aaggagtaca agtgcaaggt ctccaacaaa    1020
ggcctcccag cccccatcga gaaaaccatc tccaaaacca agggcagcc ccgagaacca    1080 caggtgtaca ccctgccccc atcccgggag gagatgacca agaaccaggt cagcctgacc    1140
tgcctggtca aaggcttcta ccccagcgac atcgccgtgg agtgggagag caatgggcag    1200
ccggagaaca actacaagac cacacctccc atgctggact ccgacggctc cttcttcctc    1260
tacagcaagc tcaccgtgga caagagcagg tggcagcagg ggaacgtctt ctcatgctcc    1320
gtgatgcatg aggctctgca caaccactac acgcagaaga gcctctccct gtctccgggt    1380
aaatga                                                              1386

<210> SEQ ID NO 144
<211> LENGTH: 393
<212> TYPE: DNA
<213> ORGANISM: Homo sapiens

<400> SEQUENCE: 144
atgaaaaaga cagctatcgc gattgcagtg gcactggctg tttcgctac cgtagcgcag       60 gccgatatcg aactgaccca gccgccttca gtgagcgttg caccaggtca gaccgcgcgt     120
atctcgtgta gcggcgataa tattggttct ttttatgttc attggtacca gcagaaaccc    180
```

| | |
|---|---|
| gggcaggcgc cagttcttgt gatttatgat gataataatc gtccctcagg catcccggaa | 240 |
| cgctttagcg gatccaacag cggcaacacc gcgaccctga ccattagcgg cactcaggcg | 300 |
| gaagacgaag cggattatta ttgcggttct tgggctggtt cttctggttc ttatgtgttt | 360 |
| ggcggccgca cgaagttaac cgttcttggc cag | 393 |

<210> SEQ ID NO 145
<211> LENGTH: 714
<212> TYPE: DNA
<213> ORGANISM: Homo sapiens

<400> SEQUENCE: 145

| | |
|---|---|
| atgagtgtgc tcactcaggt cctggcgttg ctgctgctgt ggcttacagg tacgcgttgc | 60 |
| gacatcgccc tgacccagcc cgccagcgtg agcggcagcc ctggccagag catcaccatc | 120 |
| agctgcaccg gcaccagcag cgacgtgggc gacatcaacg acgtgagctg gtatcagcag | 180 |
| caccccggca aggcccccaa gctgatgatc tacgacgtga acaaccggcc cagcggcgtg | 240 |
| agcaaccggt tcagcggcag caagagcggc aacaccgcca cctgaccat cagcggcctc | 300 |
| caggccgagg acgaggccga ctactactgc agcagctacg cgagagcct gaccagctac | 360 |
| gtgtttggcg gcggaaccaa gcttaccgtc ctaggtcagc ccaaggctgc ccctcggtc | 420 |
| actctgttcc cgccctcctc tgaggagctt caagccaaca aggccacact ggtgtgtctc | 480 |
| ataagtgact tctacccggg agccgtgaca gtggcctgga aggcagatag cagcccgtc | 540 |
| aaggcgggag tggagacaac cacaccctcc aaacaaagca acaacaagta cgcggccagc | 600 |
| agctatctga gcctgacgcc tgagcagtgg aagtcccaca aagctacag ctgccaggtc | 660 |
| acgcatgaag ggagcaccgt ggaaaagaca gtggcccca cagaatgttc atag | 714 |

<210> SEQ ID NO 146
<211> LENGTH: 705
<212> TYPE: DNA
<213> ORGANISM: Homo sapiens

<400> SEQUENCE: 146

| | |
|---|---|
| atgagtgtgc tcactcaggt cctggcgttg ctgctgctgt ggcttacagg tacgcgttgc | 60 |
| gacatcgagc tgacccagcc ccccagcgtg agcgtggccc ctggcagac cgcccggatc | 120 |
| agctgcagcg gcgacaacat cggcagcttc tacgtgcact ggtatcagca gaagcccggc | 180 |
| caggcccccg tgctggtgat ctacgacgac aacaaccggc ccagcggcat ccccgagcgg | 240 |
| ttcagcggca gcaacagcgg caacaccgcc accctgacca tcagcggcac ccaggccgag | 300 |
| gacgaggccg actactactg cgccagctgg accggcgtgg agcccgacta cgtgtttggc | 360 |
| ggcggaacaa agcttaccgt cctaggtcag cccaaggctg cccctcggt cactctgttc | 420 |
| ccgccctcct ctgaggagct tcaagccaac aaggccacac tggtgtgtct cataagtgac | 480 |
| ttctacccgg gagccgtgac agtggcctgg aaggcagata gcagccccgt caaggcggga | 540 |
| gtggagacaa ccacaccctc caaacaaagc aacaacaagt acgcggccag cagctatctg | 600 |
| agcctgacgc ctgagcagtg gaagtcccac agaagctaca gctgccaggt cacgcatgaa | 660 |
| gggagcaccg tggaaaagac agtggccct acagaatgtt catag | 705 |

<210> SEQ ID NO 147
<211> LENGTH: 714
<212> TYPE: DNA
<213> ORGANISM: Homo sapiens

<400> SEQUENCE: 147

```
atgagtgtgc tcactcaggt cctggcgttg ctgctgctgt ggcttacagg tacgcgttgc    60
gacatcgccc tgacccagcc cgccagcgtg agcggcagcc ctggccagag catcaccatc   120
agctgcaccg gcaccagcag cgacgtgggc gacatcaacg acgtgagctg gtatcagcag   180 cacccoggca aggcccccaa gctgatgatc tacgacgtga caaccggcc cagcggcgtg    240 agcaaccggt tcagcggcag caagagcggc aacaccgcca gcctgaccat cagcggcctc   300
caggccgagg acgaggccga ctactactgc cagagctacg ccggcagcta cctgagcgag   360
gtgttcggcg agggaccaa gcttaccgtc ctaggtcagc ccaaggctgc cccctcggtc    420
actctgttcc cgcccctcct ctgaggagctt caagccaaca aggccacact ggtgtgtctc   480
ataagtgact tctacccggg agccgtgaca gtggcctgga aggcagatag cagccccgtc   540
aaggcgggag tggagacaac cacaccctcc aaacaaagca caacaagta cgcggccagc    600 agctatctga gcctgacgcc tgagcagtgg aagtcccaca aagctacag ctgccaggtc    660 acgcatgaag ggagcaccgt ggaaaagaca gtggccccta cagaatgttc atag          714
```

<210> SEQ ID NO 148
<211> LENGTH: 714
<212> TYPE: DNA
<213> ORGANISM: Homo sapiens

<400> SEQUENCE: 148

```
atgagtgtgc tcactcaggt cctggcgttg ctgctgctgt ggcttacagg tacgcgttgc    60
gacatcgccc tgacccagcc cgccagcgtg agcggcagcc ctggccagag catcaccatc   120
agctgcaccg gcaccagcag cgacgtgggc gacatcaacg acgtgagctg gtatcagcag   180 cacccoggca aggcccccaa gctgatgatc tacgacgtga caaccggcc cagcggcgtg    240 agcaaccggt tcagcggcag caagagcggc aacaccgcca gcctgaccat cagcggcctc   300
caggccgagg acgaggccga ctactactgc agcagctacg cgagagcct gaccagctac   360 gtgtttggcg gcggaaccaa gcttaccgtc ctaggtcagc ccaaggctgc cccctcggtc    420
actctgttcc cgcccctcct ctgaggagctt caagccaaca aggccacact ggtgtgtctc   480
ataagtgact tctacccggg agccgtgaca gtggcctgga aggcagatag cagccccgtc   540
aaggcgggag tggagacaac cacaccctcc aaacaaagca caacaagta cgcggccagc    600 agctatctga gcctgacgcc tgagcagtgg aagtcccaca aagctacag ctgccaggtc    660 acgcatgaag ggagcaccgt ggaaaagaca gtggccccta cagaatgttc atag          714
```

<210> SEQ ID NO 149
<211> LENGTH: 714
<212> TYPE: DNA
<213> ORGANISM: Homo sapiens

<400> SEQUENCE: 149

```
atgagtgtgc tcactcaggt cctggcgttg ctgctgctgt ggcttacagg tacgcgttgc    60
gacatcgccc tgacccagcc cgccagcgtg agcggcagcc ctggccagag catcaccatc   120
agctgcaccg gcaccagcag cgacgtgggc gacatcaacg acgtgagctg gtatcagcag   180 cacccoggca aggcccccaa gctgatgatc tacgacgtga caaccggcc cagcggcgtg    240 agcaaccggt tcagcggcag caagagcggc aacaccgcca gcctgaccat cagcggcctc   300
caggccgagg acgaggccga ctactactgc agcagctacg cgagagcct gaccagctac   360 gtgtttggcg gcggaaccaa gcttaccgtc ctaggtcagc ccaaggctgc cccctcggtc    420
```

| | |
|---|---|
| actctgttcc cgccctcctc tgaggagctt caagccaaca aggccacact ggtgtgtctc | 480 |
| ataagtgact tctacccggg agccgtgaca gtggcctgga aggcagatag cagcccgtc | 540 |
| aaggcgggag tggagacaac cacaccctcc aaacaaagca acaacaagta cgcggccagc | 600 |
| agctatctga gcctgacgcc tgagcagtgg aagtcccaca gaagctacag ctgccaggtc | 660 |
| acgcatgaag ggagcaccgt ggaaaagaca gtggccccta cagaatgttc atag | 714 |

<210> SEQ ID NO 150
<211> LENGTH: 714
<212> TYPE: DNA
<213> ORGANISM: Homo sapiens

<400> SEQUENCE: 150

| | |
|---|---|
| atgagtgtgc tcactcaggt cctggcgttg ctgctgctgt ggcttacagg tacgcgttgc | 60 |
| gacatcgccc tgacccagcc cgccagcgtg agcggcagcc tggccagag catcaccatc | 120 |
| agctgcaccg gcaccagcag cgacgtgggc gacatcaacg acgtgagctg gtatcagcag | 180 |
| caccccggca aggcccccaa gctgatgatc tacgacgtga caaccggcc cagcggcgtg | 240 |
| agcaaccggt tcagcggcag caagagcggc aacaccgcca gcctgaccat cagcggcctc | 300 |
| caggccgagg acgaggccga ctactactgc agcagctacg cgagagcct gaccagctac | 360 |
| gtgtttggcg gcggaaccaa gcttaccgtc ctaggtcagc ccaaggctgc ccctcggtc | 420 |
| actctgttcc cgccctcctc tgaggagctt caagccaaca aggccacact ggtgtgtctc | 480 |
| ataagtgact tctacccggg agccgtgaca gtggcctgga aggcagatag cagcccgtc | 540 |
| aaggcgggag tggagacaac cacaccctcc aaacaaagca acaacaagta cgcggccagc | 600 |
| agctatctga gcctgacgcc tgagcagtgg aagtcccaca gaagctacag ctgccaggtc | 660 |
| acgcatgaag ggagcaccgt ggaaaagaca gtggccccta cagaatgttc atag | 714 |

<210> SEQ ID NO 151
<211> LENGTH: 714
<212> TYPE: DNA
<213> ORGANISM: Homo sapiens

<400> SEQUENCE: 151

| | |
|---|---|
| atgagtgtgc tcactcaggt cctggcgttg ctgctgctgt ggcttacagg tacgcgttgc | 60 |
| gacatcgccc tgacccagcc cgccagcgtg agcggcagcc tggccagag catcaccatc | 120 |
| agctgcaccg gcaccagcag cgacgtgggc gacatcaacg acgtgagctg gtatcagcag | 180 |
| caccccggca aggcccccaa gctgatgatc tacgacgtga caaccggcc cagcggcgtg | 240 |
| agcaaccggt tcagcggcag caagagcggc aacaccgcca gcctgaccat cagcggcctc | 300 |
| caggccgagg acgaggccga ctactactgc agcagctacg cgagagcct gaccagctac | 360 |
| gtgtttggcg gcggaaccaa gcttaccgtc ctaggtcagc ccaaggctgc ccctcggtc | 420 |
| actctgttcc cgccctcctc tgaggagctt caagccaaca aggccacact ggtgtgtctc | 480 |
| ataagtgact tctacccggg agccgtgaca gtggcctgga aggcagatag cagcccgtc | 540 |
| aaggcgggag tggagacaac cacaccctcc aaacaaagca acaacaagta cgcggccagc | 600 |
| agctatctga gcctgacgcc tgagcagtgg aagtcccaca gaagctacag ctgccaggtc | 660 |
| acgcatgaag ggagcaccgt ggaaaagaca gtggccccta cagaatgttc atag | 714 |

<210> SEQ ID NO 152
<211> LENGTH: 714
<212> TYPE: DNA
<213> ORGANISM: Homo sapiens

<400> SEQUENCE: 152

```
atgagtgtgc tcactcaggt cctggcgttg ctgctgctgt ggcttacagg tacgcgttgc    60
gacatcgccc tgacccagcc cgccagcgtg agcggcagcc ctggccagag catcaccatc   120
agctgcaccg gcaccagcag cgacgtgggc gacatcaacg acgtgagctg gtatcagcag   180
caccccggca aggcccccaa gctgatgatc tacgacgtga acaaccggcc cagcggcgtg   240
agcaaccggt tcagcggcag caagagcggc aacaccgcca gcctgaccat cagcggcctc   300
caggccgagg acgaggccga ctactactgc agcacctacg acggccctgg cctgagcgag   360
gtgttcggcg agggaccaa gcttaccgtc ctaggtcagc ccaaggctgc ccctcggtc   420
actctgttcc cgccctcctc tgaggagctt caagccaaca aggccacact ggtgtgtctc   480
ataagtgact tctacccggg agccgtgaca gtggcctgga aggcagatag cagccccgtc   540
aaggcgggag tggagacaac cacaccctcc aaacaaagca caacaagta cgcggccagc   600
agctatctga gcctgacgcc tgagcagtgg aagtcccaca aagctacag ctgccaggtc   660
acgcatgaag ggagcaccgt ggaaaagaca gtggccccta cagaatgttc atag        714
```

<210> SEQ ID NO 153
<211> LENGTH: 714
<212> TYPE: DNA
<213> ORGANISM: Homo sapiens

<400> SEQUENCE: 153

```
atgagtgtgc tcactcaggt cctggcgttg ctgctgctgt ggcttacagg tacgcgttgc    60
gacatcgccc tgacccagcc cgccagcgtg agcggcagcc ctggccagag catcaccatc   120
agctgcaccg gcaccagcag cgacgtgggc gacatcaacg acgtgagctg gtatcagcag   180
caccccggca aggcccccaa gctgatgatc tacgacgtga acaaccggcc cagcggcgtg   240
agcaaccggt tcagcggcag caagagcggc aacaccgcca gcctgaccat cagcggcctc   300
caggccgagg acgaggccga ctactactgc agcacctacg acggccctgg cctgagcgag   360
gtgttcggcg agggaccaa gcttaccgtc ctaggtcagc ccaaggctgc ccctcggtc   420
actctgttcc cgccctcctc tgaggagctt caagccaaca aggccacact ggtgtgtctc   480
ataagtgact tctacccggg agccgtgaca gtggcctgga aggcagatag cagccccgtc   540
aaggcgggag tggagacaac cacaccctcc aaacaaagca caacaagta cgcggccagc   600
agctatctga gcctgacgcc tgagcagtgg aagtcccaca aagctacag ctgccaggtc   660
acgcatgaag ggagcaccgt ggaaaagaca gtggccccta cagaatgttc atag        714
```

<210> SEQ ID NO 154
<211> LENGTH: 714
<212> TYPE: DNA
<213> ORGANISM: Homo sapiens

<400> SEQUENCE: 154

```
atgagtgtgc tcactcaggt cctggcgttg ctgctgctgt ggcttacagg tacgcgttgc    60
gacatcgccc tgacccagcc cgccagcgtg agcggcagcc ctggccagag catcaccatc   120
agctgcaccg gcaccagcag cgacgtgggc gacatcaacg acgtgagctg gtatcagcag   180
caccccggca aggcccccaa gctgatgatc tacgacgtga acaaccggcc cagcggcgtg   240
agcaaccggt tcagcggcag caagagcggc aacaccgcca gcctgaccat cagcggcctc   300
caggccgagg acgaggccga ctactactgc agcacctacg acggccctgg cctgagcgag   360
```

```
gtgttcggcg agggaccaa gcttaccgtc ctaggtcagc ccaaggctgc ccctcggtc    420 actctgttcc cgcctcctc tgaggagctt caagccaaca aggccacact ggtgtgtctc   480
ataagtgact tctacccggg agccgtgaca gtggcctgga aggcagatag cagccccgtc   540
aaggcgggag tggagacaac cacaccctcc aaacaaagca acaacaagta cgcggccagc   600
agctatctga gcctgacgcc tgagcagtgg aagtcccaca gaagctacag ctgccaggtc   660
acgcatgaag ggagcaccgt ggaaaagaca gtggccccta cagaatgttc atag         714
```

<210> SEQ ID NO 155
<211> LENGTH: 213
<212> TYPE: PRT
<213> ORGANISM: Homo sapiens

<400> SEQUENCE: 155

```
Met Gln Leu Pro Leu Ala Leu Cys Leu Val Cys Leu Leu Val His Thr
1               5                   10                  15

Ala Phe Arg Val Val Glu Gly Gln Gly Trp Gln Ala Phe Lys Asn Asp
                20                  25                  30

Ala Thr Glu Ile Ile Pro Glu Leu Gly Glu Tyr Pro Glu Pro Pro
            35                  40                  45

Glu Leu Glu Asn Asn Lys Thr Met Asn Arg Ala Glu Asn Gly Gly Arg
    50                  55                  60

Pro Pro His His Pro Phe Glu Thr Lys Asp Val Ser Glu Tyr Ser Cys
65                  70                  75                  80

Arg Glu Leu His Phe Thr Arg Tyr Val Thr Asp Gly Pro Cys Arg Ser
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Gly Lys Trp Trp Arg Pro Ser
        115                 120                 125

Gly Pro Asp Phe Arg Cys Ile Pro Asp Arg Tyr Arg Ala Gln Arg Val
    130                 135                 140

Gln Leu Leu Cys Pro Gly Gly Glu Ala Pro Arg Ala Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Thr Glu Ala Ala Arg Pro Gln Lys Gly
            180                 185                 190

Arg Lys Pro Arg Pro Arg Ala Arg Ser Ala Lys Ala Asn Gln Ala Glu
        195                 200                 205

Leu Glu Asn Ala Tyr
    210
```

<210> SEQ ID NO 156
<211> LENGTH: 14
<212> TYPE: PRT
<213> ORGANISM: Homo sapiens

<400> SEQUENCE: 156

```
Ala Arg Leu Leu Asn Ala Ile Gly Arg Gly Lys Trp Trp Arg
1               5                   10
```

<210> SEQ ID NO 157
<211> LENGTH: 15
<212> TYPE: PRT
<213> ORGANISM: Homo sapiens

```
<400> SEQUENCE: 157

Arg Leu Val Ala Ser Cys Lys Cys Lys Arg Leu Thr Arg Phe His
1               5                   10                  15

<210> SEQ ID NO 158
<211> LENGTH: 13
<212> TYPE: PRT
<213> ORGANISM: Artificial Sequence
<220> FEATURE:
<223> OTHER INFORMATION: Artificial sequence

<400> SEQUENCE: 158

Gly Gly Gly Ser Gly Gly Gly Ser Gly Gly Gly Gly
1               5                   10

<210> SEQ ID NO 159
<211> LENGTH: 19
<212> TYPE: PRT
<213> ORGANISM: Artificial Sequence
<220> FEATURE:
<223> OTHER INFORMATION: Artificial sequence

<400> SEQUENCE: 159

Gly Gly Gly Gly Ser Gly Gly Gly Gly Ser Gly Gly Gly Gly Ser Gly
1               5                   10                  15

Gly Gly Gly

<210> SEQ ID NO 160
<211> LENGTH: 21
<212> TYPE: DNA
<213> ORGANISM: Artificial Sequence
<220> FEATURE:
<223> OTHER INFORMATION: Artificial sequence

<400> SEQUENCE: 160
taaattatca taaagtccta a                                         21

<210> SEQ ID NO 161
<211> LENGTH: 21
<212> TYPE: DNA
<213> ORGANISM: Artificial Sequence
<220> FEATURE:
<223> OTHER INFORMATION: Artificial sequence

<400> SEQUENCE: 161
aggactttat gataatttat t                                         21

<210> SEQ ID NO 162
<211> LENGTH: 21
<212> TYPE: DNA
<213> ORGANISM: Artificial Sequence
<220> FEATURE:
<223> OTHER INFORMATION: Artificial sequence

<400> SEQUENCE: 162
atagtggtta ataactccca g                                         21

<210> SEQ ID NO 163
<211> LENGTH: 21
<212> TYPE: DNA
<213> ORGANISM: Artificial Sequence
<220> FEATURE:
<223> OTHER INFORMATION: Artificial sequence

<400> SEQUENCE: 163
```

```
ggagttattt aaccactatt t                                              21

<210> SEQ ID NO 164
<211> LENGTH: 21
<212> TYPE: DNA
<213> ORGANISM: Artificial Sequence
<220> FEATURE:
<223> OTHER INFORMATION: Artificial sequence

<400> SEQUENCE: 164
taaattctcg tgatgtgcca t                                              21

<210> SEQ ID NO 165
<211> LENGTH: 21
<212> TYPE: DNA
<213> ORGANISM: Artificial Sequence
<220> FEATURE:
<223> OTHER INFORMATION: Artificial sequence

<400> SEQUENCE: 165
ggcacatcac gagaatttat t                                              21

<210> SEQ ID NO 166
<211> LENGTH: 21
<212> TYPE: DNA
<213> ORGANISM: Artificial Sequence
<220> FEATURE:
<223> OTHER INFORMATION: Artificial sequence

<400> SEQUENCE: 166
tttcttatag cacagctggt t                                              21

<210> SEQ ID NO 167
<211> LENGTH: 21
<212> TYPE: DNA
<213> ORGANISM: Artificial Sequence
<220> FEATURE:
<223> OTHER INFORMATION: Artificial sequence

<400> SEQUENCE: 167
ccagctgtgc tataagaaat t                                              21

<210> SEQ ID NO 168
<211> LENGTH: 21
<212> TYPE: DNA
<213> ORGANISM: Artificial Sequence
<220> FEATURE:
<223> OTHER INFORMATION: Artificial sequence

<400> SEQUENCE: 168 tagaccttc catccacgct g                                               21

<210> SEQ ID NO 169
<211> LENGTH: 21
<212> TYPE: DNA
<213> ORGANISM: Artificial Sequence
<220> FEATURE:
<223> OTHER INFORMATION: Artificial sequence

<400> SEQUENCE: 169
gcgtggatgg aaaggtctat t                                              21

<210> SEQ ID NO 170
<211> LENGTH: 29
<212> TYPE: DNA
<213> ORGANISM: Artificial Sequence
```

```
<220> FEATURE:
<223> OTHER INFORMATION: Artificial sequence

<400> SEQUENCE: 170
atgcagctcc cactggccct gtgtcttgt                                              29

<210> SEQ ID NO 171
<211> LENGTH: 30
<212> TYPE: DNA
<213> ORGANISM: Artificial Sequence
<220> FEATURE:
<223> OTHER INFORMATION: Artificial sequence

<400> SEQUENCE: 171
aatcaggccg agctggagaa cgcctactag                                             30

<210> SEQ ID NO 172
<211> LENGTH: 443
<212> TYPE: PRT
<213> ORGANISM: Homo sapiens

<400> SEQUENCE: 172
```

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Ser His
            20                  25                  30

Trp Leu Ser Trp Val Arg Gln Ala Pro Gly Lys Gly Leu Glu Trp Val
        35                  40                  45

Ser Asn Ile Asn Tyr Asp Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Tyr Leu His Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg

```
                275                 280                 285
Glu Glu Gln Phe Asn Ser Thr Phe Arg Val Val Ser Val Leu Thr Val
    290                 295                 300
Val His Gln Asp Trp Leu Asn Gly Lys Glu Tyr Lys Cys Lys Val Ser
305                 310                 315                 320
Asn Lys Gly Leu Pro Ala Pro Ile Glu Lys Thr Ile Ser Lys Thr Lys
                325                 330                 335
Gly Gln Pro Arg Glu Pro Gln Val Tyr Thr Leu Pro Pro Ser Arg Glu
            340                 345                 350
Glu Met Thr Lys Asn Gln Val Ser Leu Thr Cys Leu Val Lys Gly Phe
        355                 360                 365
Tyr Pro Ser Asp Ile Ala Val Glu Trp Glu Ser Asn Gly Gln Pro Glu
    370                 375                 380
Asn Asn Tyr Lys Thr Thr Pro Pro Met Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
            420                 425                 430
Thr Gln Lys Ser Leu Ser Leu Ser Pro Gly Lys
        435                 440

<210> SEQ ID NO 173
<211> LENGTH: 217
<212> TYPE: PRT
<213> ORGANISM: Artificial Sequence
<220> FEATURE:
<223> OTHER INFORMATION: Homo sapiens

<400> SEQUENCE: 173

Asp Ile Ala Leu Thr Gln Pro Ala Ser Val Ser Gly Ser Pro Gly Gln
1               5                   10                  15
Ser Ile Thr Ile Ser Cys Thr Gly Thr Ser Ser Asp Val Gly Asp Ile
                20                  25                  30
Asn Asp Val Ser Trp Tyr Gln Gln His Pro Gly Lys Ala Pro Lys Leu
            35                  40                  45
Met Ile Tyr Asp Val Asn Asn Arg Pro Ser Gly Val Ser Asn Arg Phe
        50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Gln Ser Tyr Ala Gly Ser
                85                  90                  95
Tyr Leu Ser Glu Val Phe Gly Gly Gly Thr Lys Leu Thr Val Leu Gly
            100                 105                 110
Gln Pro Lys Ala Ala Pro Ser Val Thr Leu Phe Pro Pro Ser Ser Glu
        115                 120                 125
Glu Leu Gln Ala Asn Lys Ala Thr Leu Val Cys Leu Ile Ser Asp Phe
    130                 135                 140
Tyr Pro Gly Ala Val Thr Val Ala Trp Lys Ala Asp Ser Ser Pro Val
145                 150                 155                 160
Lys Ala Gly Val Glu Thr Thr Thr Pro Ser Lys Gln Ser Asn Asn Lys
                165                 170                 175
Tyr Ala Ala Ser Ser Tyr Leu Ser Leu Thr Pro Glu Gln Trp Lys Ser
            180                 185                 190
His Arg Ser Tyr Ser Cys Gln Val Thr His Glu Gly Ser Thr Val Glu
```

```
                195                 200                 205
Lys Thr Val Ala Pro Thr Glu Cys Ser
    210                 215

<210> SEQ ID NO 174
<211> LENGTH: 26
<212> TYPE: PRT
<213> ORGANISM: Homo sapiens

<400> SEQUENCE: 174

Cys Gly Pro Ala Arg Leu Leu Pro Asn Ala Ile Gly Arg Gly Lys Trp
1               5                   10                  15

Trp Arg Pro Ser Gly Pro Asp Phe Arg Cys
            20                  25

<210> SEQ ID NO 175
<211> LENGTH: 60
<212> TYPE: PRT
<213> ORGANISM: Homo sapiens

<400> SEQUENCE: 175

Asp Val Ser Glu Tyr Cys Arg Glu Leu His Phe Thr Arg Ser Ala Lys
1               5                   10                  15

Pro Val Thr Glu Leu Val Cys Ser Gly Gln Cys Gly Pro Ala Arg Trp
            20                  25                  30

Trp Arg Pro Ser Gly Pro Asp Phe Arg Cys Ile Pro Asp Arg Tyr Arg
        35                  40                  45

Leu Val Ala Ser Cys Lys Cys Lys Arg Leu Thr Arg
    50                  55                  60

<210> SEQ ID NO 176
<211> LENGTH: 133
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 176

Met Asp Thr Arg Ala Pro Thr Gln Leu Leu Gly Leu Leu Leu Leu Trp
1               5                   10                  15

Leu Pro Gly Ala Thr Phe Ala Gln Val Leu Thr Gln Ser Pro Ser Ser
            20                  25                  30

Leu Ser Ala Ser Val Gly Asp Arg Val Thr Ile Thr Cys Gln Ser Ser
        35                  40                  45

Gln Ser Val Tyr Asp Asn Asn Trp Leu Ala Trp Tyr Gln Gln Lys Pro
    50                  55                  60

Gly Lys Ala Pro Lys Leu Leu Ile Tyr Asp Ala Ser Asp Leu Ala Ser
65                  70                  75                  80

Gly Val Pro Ser Arg Phe Ser Gly Ser Gly Ser Gly Thr Asp Phe Thr
                85                  90                  95

Leu Thr Ile Ser Ser Leu Gln Pro Glu Asp Phe Ala Thr Tyr Tyr Cys
            100                 105                 110

Gln Gly Ala Tyr Asn Asp Val Ile Tyr Ala Phe Gly Gln Gly Thr Lys
        115                 120                 125

Val Glu Ile Lys Arg
    130
```

```
<210> SEQ ID NO 177
<211> LENGTH: 131
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<223> OTHER INFORMATION: Humanized Antibody Sequence

<400> SEQUENCE: 177

Met Glu Thr Gly Leu Arg Trp Leu Leu Leu Val Ala Val Leu Lys Gly
1               5                   10                  15

Val His Cys Glu Val Gln Leu Leu Glu Ser Gly Gly Gly Leu Val Gln
                20                  25                  30

Pro Gly Gly Ser Leu Arg Leu Ser Cys Ala Ala Ser Gly Phe Ser Leu
            35                  40                  45

Ser Ser Tyr Trp Met Asn Trp Val Arg Gln Ala Pro Gly Lys Gly Leu
        50                  55                  60

Glu Trp Val Gly Thr Ile Asp Ser Gly Gly Arg Thr Asp Tyr Ala Ser
65                  70                  75                  80

Trp Ala Lys Gly Arg Phe Thr Ile Ser Arg Asp Asn Ser Lys Asn Thr
                85                  90                  95

Met Tyr Leu Gln Met Asn Ser Leu Arg Ala Glu Asp Thr Ala Arg Tyr
                100                 105                 110

Tyr Cys Ala Arg Asn Trp Asn Leu Trp Gly Gln Gly Thr Leu Val Thr
            115                 120                 125

Val Ser Ser
        130
```